(12) United States Patent
Forster et al.

(10) Patent No.: US 8,128,692 B2
(45) Date of Patent: Mar. 6, 2012

(54) PROSTHETIC HEART VALVES, SCAFFOLDING STRUCTURES, AND SYSTEMS AND METHODS FOR IMPLANTATION OF SAME

(75) Inventors: David C. Forster, Menlo Park, CA (US); Scott Heneveld, Whitmore, CA (US); Brandon Walsh, Syracuse, UT (US); Richard Ginn, Gilroy, CA (US)

(73) Assignee: AorTx, Inc., Redwood City, CA (US)

( * ) Notice: Subject to any disclaimer, the term of this patent is extended or adjusted under 35 U.S.C. 154(b) by 227 days.

(21) Appl. No.: 11/067,330

(22) Filed: Feb. 25, 2005

(65) Prior Publication Data

US 2005/0203615 A1 Sep. 15, 2005

Related U.S. Application Data

(60) Provisional application No. 60/548,731, filed on Feb. 27, 2004, provisional application No. 60/559,199, filed on Apr. 1, 2004.

(51) Int. Cl.
*A61F 2/24* (2006.01)

(52) U.S. Cl. ........................ 623/2.41; 606/153

(58) Field of Classification Search ......... 623/2.11–2.42
See application file for complete search history.

(56) References Cited

U.S. PATENT DOCUMENTS

| | | |
|---|---|---|
| 376,531 A | 1/1888 | Byrnes |
| 1,314,601 A | 9/1919 | McCaskey |
| 3,579,642 A | 5/1971 | Hefferman |
| 3,587,115 A * | 6/1971 | Shiley ........................... 23/2.38 |
| 3,657,744 A | 4/1972 | Ersek |
| 3,671,979 A * | 6/1972 | Moulopoulos .............. 623/2.11 |
| 3,755,823 A | 9/1973 | Hancock |
| 3,867,728 A | 2/1975 | Stubstad et al. |
| 4,056,854 A | 11/1977 | Boretos et al. |
| 4,106,129 A | 8/1978 | Carpentier et al. |
| 4,328,839 A | 5/1982 | Lyons et al. |
| 4,339,831 A | 7/1982 | Johnson |
| 4,340,091 A | 7/1982 | Skelton et al. |
| 4,624,822 A | 11/1986 | Arru et al. |
| 4,683,883 A * | 8/1987 | Martin ............................ 606/1 |
| 4,692,165 A | 9/1987 | Bokros |
| 4,758,151 A | 7/1988 | Arru et al. |
| 4,822,345 A | 4/1989 | Danforth |
| 4,822,353 A | 4/1989 | Bokros |
| 4,856,516 A | 8/1989 | Hillstead |

(Continued)

FOREIGN PATENT DOCUMENTS

WO    WO 91/17730    11/1991

(Continued)

OTHER PUBLICATIONS

U.S. Appl. No. 11/066,126—Office Action, Oct. 16, 2008.

(Continued)

*Primary Examiner* — David Isabella
*Assistant Examiner* — Ann Schillinger
(74) *Attorney, Agent, or Firm* — Dickstein Shapiro LLP; Mark Stirrat

(57) ABSTRACT

Prosthetic valves and their component parts are described, as are prosthetic valve delivery devices and methods for their use. The prosthetic valves are particularly adapted for use in percutaneous aortic valve replacement procedures. The delivery devices are particularly adapted for use in minimally invasive surgical procedures.

40 Claims, 31 Drawing Sheets

U.S. PATENT DOCUMENTS

| | | |
|---|---|---|
| 4,878,495 A | 11/1989 | Grayzel |
| 4,878,906 A | 11/1989 | Lindemann et al. |
| 4,960,424 A | 10/1990 | Grooters |
| 4,994,077 A | 2/1991 | Dobben |
| 5,002,567 A | 3/1991 | Bona et al. |
| 5,037,434 A | 8/1991 | Lane |
| 5,078,737 A | 1/1992 | Bona et al. |
| 5,098,374 A | 3/1992 | Othel-Jacobsen et al. |
| 5,123,919 A | 6/1992 | Sauter et al. |
| 5,163,953 A | 11/1992 | Vince |
| 5,163,954 A | 11/1992 | Curcio et al. |
| 5,213,580 A | 5/1993 | Slepian et al. |
| 5,238,454 A | 8/1993 | Schmidt |
| 5,326,371 A | 7/1994 | Love et al. |
| 5,328,471 A | 7/1994 | Slepian |
| 5,370,685 A * | 12/1994 | Stevens .................. 623/2.11 |
| 5,397,348 A | 3/1995 | Campbell et al. |
| 5,397,351 A | 3/1995 | Pavcnik et al. |
| 5,403,305 A | 4/1995 | Sauter et al. |
| 5,411,552 A | 5/1995 | Andersen et al. |
| 5,423,886 A | 6/1995 | Arru et al. |
| 5,443,474 A | 8/1995 | Sfakianos et al. |
| 5,454,838 A | 10/1995 | Vallana et al. |
| 5,522,885 A * | 6/1996 | Love et al. .................. 623/2.11 |
| 5,531,094 A | 7/1996 | More et al. |
| 5,545,214 A | 8/1996 | Stevens |
| 5,554,185 A | 9/1996 | Block et al. |
| 5,560,487 A | 10/1996 | Starr |
| 5,582,607 A | 12/1996 | Lackman |
| 5,607,442 A | 3/1997 | Fischell et al. |
| 5,620,456 A | 4/1997 | Sauer et al. |
| 5,668,425 A | 9/1997 | Marioni et al. |
| 5,695,515 A * | 12/1997 | Orejola .................. 606/191 |
| 5,713,860 A | 2/1998 | Kaplan et al. |
| 5,713,953 A | 2/1998 | Vallana et al. |
| 5,716,370 A * | 2/1998 | Williamson et al. .......... 606/153 |
| 5,724,705 A | 3/1998 | Hauser et al. |
| 5,772,672 A | 6/1998 | Toy et al. |
| 5,814,097 A | 9/1998 | Sterman et al. |
| 5,823,342 A | 10/1998 | Caudillo et al. |
| 5,840,081 A | 11/1998 | Andersen et al. |
| 5,855,601 A * | 1/1999 | Bessler et al. ............... 623/2.38 |
| 5,868,708 A | 2/1999 | Hart et al. |
| 5,891,195 A | 4/1999 | Klostermeyer et al. |
| 5,919,225 A | 7/1999 | Lau et al. |
| 5,921,993 A | 7/1999 | Yoon |
| 5,925,063 A | 7/1999 | Khosravi |
| 5,957,949 A | 9/1999 | Leonhardt et al. |
| 5,980,570 A | 11/1999 | Simpson |
| 5,984,959 A | 11/1999 | Robertson et al. |
| 6,027,779 A | 2/2000 | Campbell et al. |
| 6,042,607 A * | 3/2000 | Williamson et al. ......... 623/2.11 |
| 6,051,014 A | 4/2000 | Jang |
| 6,053,922 A | 4/2000 | Krause et al. |
| 6,090,138 A | 7/2000 | Chasak et al. |
| 6,092,529 A | 7/2000 | Cox |
| 6,093,530 A | 7/2000 | McIlroy et al. |
| 6,102,944 A | 8/2000 | Huynh et al. |
| 6,102,945 A | 8/2000 | Campbell |
| 6,117,169 A | 9/2000 | Moe |
| 6,132,986 A | 10/2000 | Pathak et al. |
| 6,143,024 A | 11/2000 | Campbell et al. |
| 6,143,025 A | 11/2000 | Stobie et al. |
| 6,162,172 A | 12/2000 | Cosgrove et al. |
| 6,168,614 B1 | 1/2001 | Andersen et al. |
| 6,174,331 B1 | 1/2001 | Moe et al. |
| 6,182,664 B1 | 2/2001 | Cosgrove |
| 6,197,053 B1 | 3/2001 | Cosgrove et al. |
| 6,199,696 B1 | 3/2001 | Lytle et al. |
| 6,206,918 B1 | 3/2001 | Campbell et al. |
| 6,217,610 B1 | 4/2001 | Carpentier et al. |
| 6,231,578 B1 | 5/2001 | Rajhansa |
| 6,231,602 B1 | 5/2001 | Carpentier et al. |
| 6,241,765 B1 | 6/2001 | Griffin et al. |
| 6,245,102 B1 | 6/2001 | Jayaraman |
| 6,270,526 B1 | 8/2001 | Cox |
| 6,283,995 B1 | 9/2001 | Moe et al. |
| 6,287,339 B1 | 9/2001 | Vazquez et al. |
| 6,299,637 B1 | 10/2001 | Shaolian et al. |
| 6,299,638 B1 | 10/2001 | Sauter |
| 6,338,740 B1 | 1/2002 | Carpentier |
| 6,342,070 B1 | 1/2002 | Nguyen-Thien-Nhon |
| 6,348,068 B1 | 2/2002 | Campbell et al. |
| 6,350,281 B1 | 2/2002 | Rhee |
| 6,350,732 B1 | 2/2002 | Moore et al. |
| 6,364,905 B1 | 4/2002 | Simpson et al. |
| 6,371,983 B1 | 4/2002 | Lane |
| 6,383,147 B1 | 5/2002 | Stobie |
| 6,391,054 B2 | 5/2002 | Carpentier et al. |
| 6,402,780 B2 * | 6/2002 | Williamson et al. ......... 623/2.11 |
| 6,405,084 B2 | 6/2002 | Plicchi et al. |
| 6,409,758 B2 * | 6/2002 | Stobie et al. ................. 623/2.11 |
| 6,425,916 B1 * | 7/2002 | Garrison et al. ............. 623/2.11 |
| 6,453,062 B1 | 9/2002 | MacNutt et al. |
| 6,454,799 B1 * | 9/2002 | Schreck ...................... 623/2.18 |
| 6,458,155 B1 | 10/2002 | Van Nguyen et al. |
| 6,461,382 B1 | 10/2002 | Cao |
| 6,475,239 B1 | 11/2002 | Campbell et al. |
| 6,479,079 B1 | 11/2002 | Pathak et al. |
| 6,482,228 B1 | 11/2002 | Norred |
| 6,485,512 B1 | 11/2002 | Cheng |
| 6,493,585 B2 | 12/2002 | Plicchi et al. |
| 6,530,952 B2 * | 3/2003 | Vesely .......................... 623/2.18 |
| 6,544,279 B1 | 4/2003 | Hopkins et al. |
| 6,558,418 B2 | 5/2003 | Carpentier et al. |
| 6,565,602 B2 | 5/2003 | Rolando et al. |
| 6,569,196 B1 | 5/2003 | Vesely |
| 6,572,642 B2 | 6/2003 | Rinaldi et al. |
| 6,582,462 B1 | 6/2003 | Andersen et al. |
| 6,585,632 B2 | 7/2003 | Vallana et al. |
| 6,585,766 B1 | 7/2003 | Huynh et al. |
| 6,596,471 B2 | 7/2003 | Pathak et al. |
| 6,602,288 B1 | 8/2003 | Cosgrove et al. |
| 6,613,085 B1 | 9/2003 | Anderson et al. |
| 6,616,690 B2 | 9/2003 | Rolando et al. |
| 6,635,085 B1 | 10/2003 | Caffey et al. |
| 6,638,303 B1 | 10/2003 | Campbell |
| 6,652,578 B2 | 11/2003 | Bailey et al. |
| 6,663,667 B2 | 12/2003 | Dehdashtian et al. |
| 6,673,109 B2 | 1/2004 | Cox |
| 6,679,871 B2 | 1/2004 | Hahnen |
| 6,682,543 B2 | 1/2004 | Barbut et al. |
| 6,682,558 B2 | 1/2004 | Tu et al. |
| 6,682,559 B2 * | 1/2004 | Myers et al. ................. 623/2.13 |
| 6,689,149 B2 | 2/2004 | Maahs |
| 6,692,512 B2 | 2/2004 | Jang |
| 6,706,033 B1 | 3/2004 | Martinez et al. |
| 6,719,787 B2 | 4/2004 | Cox |
| 6,719,788 B2 | 4/2004 | Cox |
| 6,719,789 B2 | 4/2004 | Cox |
| 6,723,122 B2 | 4/2004 | Yang et al. |
| 6,730,118 B2 | 5/2004 | Spenser et al. |
| 6,733,513 B2 | 5/2004 | Boyle et al. |
| 6,733,525 B2 * | 5/2004 | Yang et al. ................... 623/2.18 |
| 6,736,845 B2 | 5/2004 | Marquez et al. |
| 6,736,846 B2 | 5/2004 | Cox |
| 6,767,362 B2 * | 7/2004 | Schreck ...................... 623/2.11 |
| 6,770,083 B2 | 8/2004 | Seguin |
| 6,783,988 B1 | 8/2004 | Dinh et al. |
| 6,790,219 B1 | 9/2004 | Murphy |
| 6,796,972 B1 | 9/2004 | Sinofsky et al. |
| 6,797,000 B2 | 9/2004 | Simpson et al. |
| 6,805,710 B2 | 10/2004 | Bolling et al. |
| 6,821,279 B2 | 11/2004 | Di Emidio |
| 6,821,297 B2 | 11/2004 | Snyders |
| 6,846,324 B2 | 1/2005 | Stobie |
| 6,849,088 B2 | 2/2005 | Dehdashtian et al. |
| 6,858,039 B2 | 2/2005 | McCarthy |
| 6,875,231 B2 | 4/2005 | Anduiza et al. |
| 6,878,168 B2 | 4/2005 | Carpentier et al. |
| 6,893,460 B2 | 5/2005 | Spenser et al. |
| 6,896,698 B2 | 5/2005 | Rolando et al. |
| 6,908,481 B2 | 6/2005 | Cribier |
| 6,939,365 B1 | 9/2005 | Fogarty et al. |
| 6,945,997 B2 | 9/2005 | Huynh et al. |
| 6,951,571 B1 | 10/2005 | Srivastava |
| 6,962,605 B2 | 11/2005 | Cosgrove et al. |

| | | |
|---|---|---|
| 6,986,775 B2 | 1/2006 | Morales et al. |
| 6,988,881 B2 | 1/2006 | Motsenbocker et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,681 B2 | 3/2006 | Vesely |
| 7,011,682 B2 | 3/2006 | Lashinski et al. |
| 7,014,648 B2 | 3/2006 | Ambrisco et al. |
| 7,018,406 B2 | 3/2006 | Seguin et al. |
| 7,044,966 B2 * | 5/2006 | Svanidze et al. ............... 623/2.1 |
| 7,060,092 B2 | 6/2006 | Kuribayashi et al. |
| 7,252,682 B2 | 8/2007 | Seguin |
| 7,374,571 B2 * | 5/2008 | Pease et al. ................ 623/2.12 |
| 7,429,270 B2 | 9/2008 | Baumgartner et al. |
| 2001/0016758 A1 | 8/2001 | Plicchi et al. |
| 2001/0018600 A1 | 8/2001 | Plicchi et al. |
| 2001/0039450 A1 | 11/2001 | Pavcnik et al. |
| 2001/0049541 A1 | 12/2001 | Plicchi et al. |
| 2002/0032482 A1 | 3/2002 | Cox |
| 2002/0038128 A1 * | 3/2002 | Turovkiy et al. ............... 606/164 |
| 2002/0042651 A1 * | 4/2002 | Liddicoat et al. ............ 623/2.11 |
| 2002/0052647 A1 | 5/2002 | Rolando et al. |
| 2002/0055775 A1 | 5/2002 | Carpentier et al. |
| 2002/0058994 A1 * | 5/2002 | Hill et al. .................... 623/2.11 |
| 2002/0072793 A1 | 6/2002 | Rolando et al. |
| 2002/0095173 A1 | 7/2002 | Mazzocchi et al. |
| 2002/0099441 A1 | 7/2002 | Dehdashtian |
| 2002/0117264 A1 | 8/2002 | Rinaldi et al. |
| 2002/0133226 A1 * | 9/2002 | Marquez et al. ............. 623/2.11 |
| 2002/0138138 A1 | 9/2002 | Yang |
| 2002/0161431 A1 * | 10/2002 | Stobie et al. ................ 623/2.11 |
| 2002/0163104 A1 | 11/2002 | Motsenbocker et al. |
| 2002/0183766 A1 | 12/2002 | Seguin |
| 2002/0183831 A1 | 12/2002 | Rolando et al. |
| 2003/0009076 A1 | 1/2003 | Vallana et al. |
| 2003/0023262 A1 | 1/2003 | Welch |
| 2003/0027332 A1 | 2/2003 | Lafrance et al. |
| 2003/0033002 A1 | 2/2003 | Dehdashtian et al. |
| 2003/0036795 A1 | 2/2003 | Andersen et al. |
| 2003/0050694 A1 | 3/2003 | Yang et al. |
| 2003/0055495 A1 | 3/2003 | Pease et al. |
| 2003/0065356 A1 | 4/2003 | Tsugita et al. |
| 2003/0114913 A1 | 6/2003 | Spenser et al. |
| 2003/0114917 A1 | 6/2003 | Holloway et al. |
| 2003/0130721 A1 | 7/2003 | Martin et al. |
| 2003/0153943 A1 * | 8/2003 | Michael et al. ............... 606/200 |
| 2003/0153946 A1 | 8/2003 | Kimblad |
| 2003/0195613 A1 | 10/2003 | Curcio et al. |
| 2003/0212433 A1 | 11/2003 | Ambrisco et al. |
| 2004/0015224 A1 | 1/2004 | Armstrong et al. |
| 2004/0030382 A1 * | 2/2004 | St. Goar et al. ............. 623/2.36 |
| 2004/0034380 A1 | 2/2004 | Woolfson et al. |
| 2004/0049266 A1 | 3/2004 | Anduiza et al. |
| 2004/0078074 A1 | 4/2004 | Anderson et al. |
| 2004/0092858 A1 | 5/2004 | Wilson et al. |
| 2004/0092989 A1 | 5/2004 | Wilson et al. |
| 2004/0093060 A1 | 5/2004 | Seguin et al. |
| 2004/0093080 A1 | 5/2004 | Helmus et al. |
| 2004/0127979 A1 | 7/2004 | Wilson et al. |
| 2004/0148017 A1 * | 7/2004 | Stobie .......................... 623/2.11 |
| 2004/0148018 A1 * | 7/2004 | Carpentier et al. .......... 623/2.18 |
| 2004/0153140 A1 | 8/2004 | Rolando et al. |
| 2004/0158276 A1 | 8/2004 | Barbut et al. |
| 2004/0172124 A1 | 9/2004 | Vallana et al. |
| 2004/0186563 A1 * | 9/2004 | Lobbi .......................... 623/2.11 |
| 2004/0199245 A1 | 10/2004 | Lauterjung |
| 2004/0210304 A1 | 10/2004 | Seguin et al. |
| 2004/0225352 A1 | 11/2004 | Osborne et al. |
| 2004/0243222 A1 | 12/2004 | Osborne et al. |
| 2004/0249433 A1 | 12/2004 | Freitag |
| 2005/0027337 A1 | 2/2005 | Rudko et al. |
| 2005/0033398 A1 * | 2/2005 | Seguin ......................... 623/1.11 |
| 2005/0038497 A1 | 2/2005 | Neuendorf et al. |
| 2005/0043760 A1 | 2/2005 | Fogarty et al. |
| 2005/0043790 A1 | 2/2005 | Seguin |
| 2005/0043792 A1 | 2/2005 | Solem et al. |
| 2005/0065594 A1 | 3/2005 | DiMatteo et al. |
| 2005/0075584 A1 | 4/2005 | Cali |
| 2005/0075712 A1 | 4/2005 | Biancucci et al. |
| 2005/0075725 A1 | 4/2005 | Rowe |
| 2005/0090888 A1 | 4/2005 | Hines et al. |
| 2005/0096734 A1 | 5/2005 | Majercak et al. |
| 2005/0096740 A1 | 5/2005 | Langberg et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0228485 A1 | 10/2005 | Rolando et al. |
| 2005/0228495 A1 | 10/2005 | Macoviak |
| 2005/0267493 A1 | 12/2005 | Schreck et al. |
| 2005/0277959 A1 | 12/2005 | Cosgrove et al. |
| 2006/0004442 A1 | 1/2006 | Spenser et al. |
| 2006/0015179 A1 | 1/2006 | Bulman-Fleming et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0052867 A1 | 3/2006 | Revuelta |
| 2006/0058871 A1 | 3/2006 | Zakay et al. |
| 2006/0069424 A1 | 3/2006 | Acosta et al. |
| 2006/0095052 A1 | 5/2006 | Chambers |
| 2006/0122633 A1 | 6/2006 | To et al. |
| 2006/0173537 A1 | 8/2006 | Yang et al. |
| 2006/0217764 A1 | 9/2006 | Abbott et al. |
| 2007/0016286 A1 | 1/2007 | Herrmann et al. |
| 2007/0088431 A1 | 4/2007 | Bourang et al. |
| 2008/0140172 A1 | 6/2008 | Carpenter et al. |

FOREIGN PATENT DOCUMENTS

| | | |
|---|---|---|
| WO | WO 99/33414 | 7/1999 |
| WO | WO 01/76510 A2 | 10/2001 |
| WO | WO 03/003949 A2 | 1/2003 |
| WO | WO 03/047468 A1 | 6/2003 |
| WO | WO 03/096932 A1 | 11/2003 |
| WO | WO 03/105670 A2 | 12/2003 |
| WO | WO 2005009285 A2 | 2/2005 |
| WO | WO2005009285 | 3/2005 |
| WO | WO 2005/076973 A2 | 8/2005 |
| WO | WO 2005/087140 A1 | 9/2005 |
| WO | WO 2006/066150 A2 | 6/2006 |

OTHER PUBLICATIONS

U.S. Appl. No. 11/066,126—Office Action, Apr. 3, 2009.
U.S. Appl. No. 11/066,124—Office Action, Mar. 7, 2007.
U.S. Appl. No. 11/066,124—Office Action, Mar. 7, 2008.
U.S. Appl. No. 11/066,124—Office Action, Oct. 2, 2008.
U.S. Appl. No. 11/066,124—Office Action, Jun. 9, 2009.
U.S. Appl. No. 11/067,330—Office Action, Apr. 16, 2007.
U.S. Appl. No. 11/067,330—Office Action, Jun. 11, 2008.
U.S. Appl. No. 11/067,330—Office Action, Jun. 10, 2009.
U.S. Appl. No. 11/364,715—Office Action, Dec. 11, 2006.
U.S. Appl. No. 11/364,715—Office Action, Oct. 18, 2007.
U.S. Appl. No. 11/364,715—Office Action, Jan. 12, 2009.
CN, Ser. No. 200580012735.5—Office Action, Jan. 9, 2009.
CN, Ser. No. 200580012735.5—Office Action, Jul. 10, 2009.
EP Ser. No. 05723873.5—ESR, Nov. 3, 2009.
WO Ser. No. WO2007/101159—ISR, Apr. 24, 2008.
WO Ser. No. WO2007/101160—ISR, Dec. 11, 2007.
WO Ser. No. WO2007/149905—ISR, Aug. 29, 2008.
WO Ser. No. WO2007/149841—ISR, Jul. 30, 2008.
WO Ser. No. WO2007/149933—ISR, Aug. 15, 2008.
WO Ser. No. WO2007/149910—ISR, Jan. 28, 2008.
WO Ser. No. WO2008/030946—ISR, Jan. 11, 2008.
U.S. Appl. No. 11/066,126—Office Action, Dec. 22, 2009.
European Search Report, Appln. No. 07798835.0-2320, Mar. 2, 2010.

European Search Report, Appln. No. 07814708.9-2320, Mar. 3, 2010.

European Search Report, Appln. No. 07798811.2-2320, Mar. 8, 2010.

European Search Report, Appln. No. 07757493.7-2320, Mar. 15, 2010.

* cited by examiner

PROSTHETIC HEART VALVES, SCAFFOLDING STRUCTURES, AND SYSTEMS AND METHODS FOR IMPLANTATION OF SAME

CROSS REFERENCE TO RELATED APPLICATIONS

This application claims the benefit of U.S. Provisional Application Ser. No. 60/548,731, entitled "Foldable Stent for Minimally Invasive Surgery," filed Feb. 27, 2004, and U.S. Provisional Application Ser. No. 60/559,199, entitled "Method and Multiple Balloon for Percutaneous Aortic Valve Implantation," filed Apr. 1, 2004, each of which applications is hereby incorporated by reference in its entirety.

FIELD OF THE INVENTION

The present invention relates generally to medical devices and methods. More particularly, the present invention relates to prosthetic heart valves, structures for providing scaffolding of body lumens, and devices and methods for delivering and deploying these valves and structures.

BACKGROUND OF THE INVENTION

Diseases and other disorders of the heart valve affect the proper flow of blood from the heart. Two categories of heart valve disease are stenosis and incompetence. Stenosis refers to a failure of the valve to open fully, due to stiffened valve tissue. Incompetence refers to valves that cause inefficient blood circulation by permitting backflow of blood in the heart.

Medication may be used to treat some heart valve disorders, but many cases require replacement of the native valve with a prosthetic heart valve. Prosthetic heart valves can be used to replace any of the native heart valves (aortic, mitral, tricuspid or pulmonary), although repair or replacement of the aortic or mitral valves is most common because they reside in the left side of the heart where pressures are the greatest. Two primary types of prosthetic heart valves are commonly used, mechanical heart valves and prosthetic tissue heart valves.

The caged ball design is one of the early mechanical heart valves. The caged ball design uses a small ball that is held in place by a welded metal cage. In the mid-1960s, another prosthetic valve was designed that used a tilting disc to better mimic the natural patterns of blood flow. The tilting-disc valves had a polymer disc held in place by two welded struts. The bileaflet valve was introduced in the late 1970s. It included two semicircular leaflets that pivot on hinges. The leaflets swing open completely, parallel to the direction of the blood flow. They do not close completely, which allows some backflow.

The main advantages of mechanical valves are their high durability. Mechanical heart valves are placed in young patients because they typically last for the lifetime of the patient. The main problem with all mechanical valves is the increased risk of blood clotting.

Prosthetic tissue valves include human tissue valves and animal tissue valves. Both types are often referred to as bioprosthetic valves. The design of bioprosthetic valves are closer to the design of the natural valve. Bioprosthetic valves do not require long-term anticoagulants, have better hemodynamics, do not cause damage to blood cells, and do not suffer from many of the structural problems experienced by the mechanical heart valves.

Human tissue valves include homografts, which are valves that are transplanted from another human being, and autografts, which are valves that are transplanted from one position to another within the same person.

Animal tissue valves are most often heart tissues recovered from animals. The recovered tissues are typically stiffened by a tanning solution, most often glutaraldehyde. The most commonly used animal tissues are porcine, bovine, and equine pericardial tissue.

The animal tissue valves are typically stented valves. Stentless valves are made by removing the entire aortic root and adjacent aorta as a block, usually from a pig. The coronary arteries are tied off, and the entire section is trimmed and then implanted into the patient.

A conventional heart valve replacement surgery involves accessing the heart in the patent's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

A less invasive approach to valve replacement is desired. The percutaneous implantation of a prosthetic valve is a preferred procedure because the operation is performed under local anesthesia, does not require cardiopulmonary bypass, and is less traumatic. Current attempts to provide such a device generally involve stent-like structures, which are very similar to those used in vascular stent procedures with the exception of being larger diameter as required for the aortic anatomy, as well as having leaflets attached to provide one way blood flow. These stent structures are radially contracted for delivery to the intended site, and then expanded/deployed to achieve a tubular structure in the annulus. The stent structure needs to provide two primary functions. First, the structure needs to provide adequate radial stiffness when in the expanded state. Radial stiffness is required to maintain the cylindrical shape of the structure, which assures the leaflets coapt properly. Proper leaflet coaption assures the edges of the leaflets mate properly, which is necessary for proper sealing without leaks. Radial stiffness also assures that there will be no paravalvular leakage, which is leaking between the valve and aorta interface, rather than through the leaflets. An additional need for radial stiffness is to provide sufficient interaction between the valve and native aortic wall that there will be no valve migration as the valve closes and holds full body blood pressure. This is a requirement that other vascular devices are not subjected to. The second primary function of the stent structure is the ability to be crimped to a reduced size for implantation.

Prior devices have utilized traditional stenting designs which are produced from tubing or wire wound structures. Although this type of design can provide for crimpability, it provides little radial stiffness. These devices are subject to "radial recoil" in that when the device is deployed, typically with balloon expansion, the final deployed diameter is smaller than the diameter the balloon and stent structure were expanded to. The recoil is due in part because of the stiffness mismatches between the device and the anatomical environment in which it is placed. These devices also commonly cause crushing, tearing, or other deformation to the valve leaflets during the contraction and expansion procedures. Other stenting designs have included spirally wound metallic sheets. This type of design provides high radial stiffness, yet crimping results in large material strains that can cause stress fractures and extremely large amounts of stored energy in the constrained state. Replacement heart valves are expected to survive for many years when implanted. A heart valve sees approximately 500,000,000 cycles over the course of 15 years. High stress states during crimping can reduce the fatigue life of the device. Still other devices have included tubing, wire wound structures, or spirally wound sheets formed of nitinol or other superelastic or shape memory material. These devices suffer from some of the same deficiencies as those described above. The scaffolding structures and prosthetic valves described herein address both attributes of high radial stiffness along with crimpability, and maximizing fatigue life.

SUMMARY OF THE INVENTION

The present invention provides apparatus and methods for deploying support structures in body lumens. The methods and apparatus are particularly adapted for use in percutaneous aortic valve replacement. The methods and apparatus may also find use in the peripheral vasculature, the abdominal vasculature, and in other ducts such as the biliary duct, the fallopian tubes, and similar lumen structures within the body of a patient. Although particularly adapted for use in lumens found in the human body, the apparatus and methods may also find application in the treatment of animals.

In one aspect of the invention, a prosthetic valve is provided. The prosthetic valve includes a support member and a valvular body attached to the support member. The prosthetic valve has an expanded state in which the support member has a cross-sectional shape that is generally cylindrical or generally oval and which has a first cross-sectional dimension (e.g., diameter), and a contracted state in which the support member has a second cross-sectional dimension (e.g., diameter) smaller than the first. The prosthetic valve is in its contracted state during delivery of the prosthetic valve to a treatment location, and in its expanded state after deployment at the treatment location. Preferably, the cross-sectional dimension of the support member in its expanded state is sufficiently large, and the support member possesses sufficient radial strength, to cause the support member to positively physically engage the internal surface of the body lumen, such as the aortic valve annulus or another biologically acceptable aortic position (e.g., a location in the ascending or descending aorta), thereby providing a strong friction fit.

Specifically, in several preferred embodiments, the support member has a cross-sectional dimension that is slightly larger than the dimension of the treatment location, such as a body lumen. For example, if the treatment location is the root annulus of the aortic valve, the support member may be provided with a cross-sectional dimension that is from about 0 to about 25% larger than the cross-sectional dimension of the valve annulus. Cross-sectional dimensions even larger than 25% greater than that of the body lumen may also be used, depending upon the nature of the treatment location. As described in more detail below, once deployed, the support member extends to its full cross-sectional dimension—i.e., it does not compress radially due to the radial force imparted by the lumen or other tissue. Rather, the support member will expand the cross-sectional dimension of the lumen or other tissue at the treatment location. In this way, the support member reduces the possibility of fluid leakage around the periphery of the device. In addition, due to the strength of the interference fit that results from the construction of the device, the support member will have proper apposition to the lumen or tissue to reduce the likelihood of migration of the device once deployed.

In several embodiments, the support member is a structure having at least two peripheral segments, at least two of which segments are connected to each other by a foldable junction. As used herein, the term "segment" refers to a constituent part into which the support member is divided by foldable junctions or other junctions connecting adjacent segments. In several embodiments, each segment comprises a panel, with two or more connected panels making up the support member. Alternatively, and without intending to otherwise limit the descriptions provided, segments may comprise beams, braces, struts, or other structural members extending between the foldable junctions provided on the support member. Any of these (or any other) alternative structures, or any combinations thereof, may be provided as one or more segments of the support member.

In the above embodiments of the support member, the foldable junction may comprise any structural member that allows two adjacent segments to partially or completely fold one upon another. In several preferred embodiments, the foldable junction comprises a hinge. Suitable hinges include mechanical hinges, membrane hinges, living hinges, or combinations of such hinges.

In addition to the foldable junctions, two adjacent panels may be connectable by a selectively locking junction, such as pairs of opposed tabs and slots. In embodiments that include three or more segments, a combination of foldable junctions and locking junctions may be used.

The support structure may be provided with one or more anchoring members that are adapted to engage the internal wall of the body lumen. Each anchoring member may comprise a barb, a tooth, a hook, or any other member that protrudes from the external surface of the support structure to physically engage the internal wall of the body lumen. Alternatively, the anchoring member may comprise an aperture formed in the support structure that allows tissue to invaginate therethrough, i.e., the outward radial force of the support member against the vessel wall causes the frame portion of the support member to slightly embed into the vessel wall, thereby causing some of the tissue to penetrate through the aperture into the interior of the support member. The tissue invagination acts to anchor the support structure in place. An anchoring member may be selectively engageable, such as by an actuator, or it may be oriented so as to be permanently engaged. Alternatively, the anchoring member may be self-actuating, or it may be deployed automatically during deployment of the support member.

The anchoring member advantageously may perform functions in addition to engaging the internal wall of the body lumen. For example, the anchoring member may ensure proper positioning of the support structure within the body lumen. It may also prevent migration or other movement of the support structure, and it may provide additional or enhanced sealing of the support structure to the body lumen, such as by creating better tissue adherence.

The support structure may also be provided with an optional sealing member, such as a gasket. The sealing member preferably is fixed to the external surface of the support structure around all or a portion of the circumference of the support structure, and serves to decrease or eliminate the flow of fluids between the vessel wall and the support member. The sealing member may comprise a relatively soft biocompatible material, such as a polyurethane or other polymer. Preferably, the sealing member is porous or is otherwise capable of expanding or swelling when exposed to fluids, thereby enhancing the sealing ability of the sealing member. The sealing member may include a functional composition such as an adhesive, a fixative, or therapeutic agents such as drugs or other materials.

As an additional option, a coating may be applied to or created on any of the surfaces of the support member. Coatings may be applied or created to provide any desired function. For example, a coating may be applied to carry an adhesive, a fixative, or therapeutic agents such as drugs or other materials. Coatings may be created on the external surface of the support member to facilitate tissue penetration (e.g., ingrowth) into the support structure. Coatings may also be provided to promote sealing between the support member and the native tissue, or to reduce the possibility that the support member may migrate from its intended location. Other coating functions will be recognized by those skilled in the art.

The valvular body may be of a single or multi-piece construction, and includes a plurality of leaflets. The valvular body may be attached either to the internal or external surface of the support structure. In the case of a single-piece construction, the valvular body includes a base portion that is attachable to the support structure, and a plurality of (and preferably three) leaflets extending from the base portion. In the case of a multi-piece construction, the valvular body includes a plurality of (preferably three) members, each including a base portion that is attachable to the support structure and a leaflet portion. In either case, the base portion(s) of the valvular body are attached to a portion of the internal or external surface of the support structure, and the leaflets extend away from the base portion and generally inwardly toward each other to form the valve.

The valvular body, either single-piece or multi-piece, may comprise a homogeneous material, for example, a polymer such as polyurethane or other suitable elastomeric material. Alternatively, the valvular body may comprise a coated substrate, wherein the substrate comprises a polymer (e.g., polyester) or metallic (e.g., stainless steel) mesh, and the coating comprises a polymer such as polyurethane or other suitable elastomeric material. Other suitable constructions are also possible.

Alternatively, the valvular body may comprise human (including homograft or autograft) or animal (e.g., porcine, bovine, equine, or other) tissue.

The valvular body may be attached to the support structure by any suitable mechanism. For example, an attachment lip formed of a polymer, fabric, or other flexible material may be molded or adhered to the surface of the support member, and the valvular body sewn, adhered, or molded onto the attachment lip. Alternatively, an edge portion of the valvular body may be sandwiched between a pair of elastomeric strips that are attached to the surface of the support member. Other and further attachment mechanisms may also be used.

As described above, each of the foregoing embodiments of the prosthetic valve preferably has a fully expanded state for deployment within a body lumen, and a contracted state for delivery to the lumen in a minimally invasive interventional procedure through the patient's vasculature. In the fully expanded state, each of the segments of the support member is oriented peripherally and adjacent to one another, attached to each adjacent segment by a foldable junction or an locking junction. In the contracted state, the segments are folded together at the foldable junctions and, preferably, then formed into a smaller diameter tubular structure. The contracted state may be achieved in different combinations and manners of folding and rolling the segments and junctions, depending on the particular structure of the prosthetic valve.

For example, in one embodiment, the prosthetic valve comprises a generally cylindrical support member made up of three panels, with each panel connected to its adjacent panel by a hinge. The hinges may be mechanical hinges, membrane hinges, living hinges, or a combination of such hinges. In its fully expanded state, each panel of the prosthetic valve is an arcuate member that occupies approximately 120°, or one third, of the circular cross-section of the cylindrical support member. Alternatively, one or more of the panels may span a smaller portion of the cylindrical support member, while the other panel(s) are relatively larger. For example, a relatively shorter panel may be provided on a side of the valve corresponding to the non-coronary native valve leaflet, which is generally smaller than the other native valve leaflets. A valvular body is attached to the internal surface of each of the three panels. The contracted state is obtained by first inverting each of the panels at its centerline, i.e., changing each panel from a convex shape to a concave shape by bringing the centerline of each panel toward the longitudinal axis running through the center of the generally cylindrical support member. This action causes the foldable junctions to fold, creating a vertex at each foldable junction. For the foregoing three panel support member, a three vertex star-shaped structure results. In the case of a four panel support member, a four vertex star-shaped structure would result. The valvular body, which is formed of generally flexible, resilient materials, generally follows the manipulations of the support member without any substantial crimping, tearing, or permanent deformation.

Inversion of the panels results in a structure having a relatively smaller maximum transverse dimension than that of the fully expanded structure. To further reduce the transverse dimension, each vertex is curled back toward the central axis to create a plurality of lobes equi-spaced about the central axis, i.e., in the three-panel structure, three lobes are formed. The resulting multi-lobe structure has an even further reduced maximum transverse dimension, and represents one embodiment of the contracted state of the prosthetic valve.

In another embodiment, the prosthetic valve comprises a generally cylindrical support member made up of three panels defining three junctions, two of which comprise hinges, and one of which comprises a set of locking tabs and slots. The hinges may be mechanical hinges, membrane hinges, living hinges, other hinge types, or a combination of such hinges. As with the prior embodiment, in its fully expanded state, each panel of the prosthetic valve is an arcuate member that occupies approximately 120°, or one third, of the circular cross-section of the cylindrical support member. A valvular body is attached to the internal surface of each of the three panels, with at least one separation in the valvular body corresponding with the location of the locking junction on the support member. The contracted state in this alternative embodiment is obtained by first disengaging the locking tabs and slots at the non-hinge junction between a first two of the panels. Alternatively, the locking tabs and slots may be simply unlocked to permit relative motion while remaining slidably engaged. The third panel, opposite the non-hinge junction, is then inverted, i.e., changed from convex to concave by bringing the centerline of the panel toward the longitudinal axis running through the center of the generally cylindrical support member. The other two panels are then nested behind the third panel, each retaining its concave shape, by rotating the hinges connecting each panel to the third panel. The resulting structure is a curved-panel shaped member. The valvular body, which is formed of generally flexible, resilient materials, generally follows the manipulations of the support member without any substantial crimping, tearing, or permanent deformation. The structure is then curled into a tubular structure having a relatively small diameter in relation to that of the fully expanded prosthetic valve, and which represents an alternative embodiment of the contracted state of the prosthetic valve.

In still another embodiment, the prosthetic valve comprises a generally oval-shaped support member made up of two panels, with a hinge provided at the two attachment edges between the panels. The hinges may be mechanical hinges, membrane hinges, living hinges, or a combination of such hinges. A valvular body is attached to the internal surface of each of the two panels. The contracted state is obtained by first inverting one of the two panels at its centerline, i.e., changing the panel from a convex shape to a concave shape by bringing the centerline of the panel toward the longitudinal axis running through the center of the generally oval support member. This action causes the foldable junctions to fold, creating a vertex at each foldable junction, and causes the two panels to come to a nested position. The valvular body, which is formed of generally flexible, resilient materials, generally follows the manipulations of the support member without any substantial crimping, tearing, or permanent deformation. The structure is then curled into a tubular structure having a relatively small diameter in relation to that of the fully expanded prosthetic valve, and which represents another alternative embodiment of the contracted state of the prosthetic valve.

Several alternative support members are also provided. In one such alternative embodiment, the support structure is a generally tubular member constructed such that it is capable of transforming from a contracted state having a relatively small diameter and large length, to an expanded state having a relatively large diameter and small length. The transformation from the contracted state to the expanded state entails causing the tubular member to foreshorten in length while expanding radially. The forced foreshortening transformation may be achieved using any of a wide range of structural components and/or methods. In a particularly preferred form, the support structure comprises an axially activated support member. The axially activated support member includes a generally tubular body member formed of a matrix of flexible struts. In one embodiment, struts are arranged in crossing pairs forming an "X" pattern, with the ends of a first crossing pair of struts being connected to the ends of a second crossing pair of struts by a band connector, thereby forming a generally cylindrical member. Additional generally cylindrical members may be incorporated into the structure by interweaving the struts contained in the additional cylindrical member with one or more of the struts included in the first cylindrical member. An axial member is connected to at least two opposed band connectors located on opposite ends of the structure. When the axial member is decreased in length, the support member is expanded to a large diameter state, accompanied by a degree of foreshortening of the support member. When the axial member is increased in length, the support member is contracted to a smaller diameter state, accompanied by a degree of lengthening of the support member. The expanded state may be used when the support member is deployed in a body lumen, and the contracted state may be used for delivery of the device. A valvular body, as described above, may be attached to the internal or external surface of the support member.

In the foregoing embodiment, the axial member may be replaced by a circumferential member, a spirally wound member, or any other structure adapted to cause the tubular member to foreshorten and thereby to transform to the expanded state. The axial or other member may be attached to opposed connectors, to connectors that are not opposed, or connectors may not be used at all. Alternatively, the support member may be formed of a plurality of braided wires or a single wire formed into a tubular shape by wrapping around a mandrel. In either case, the structure is caused to radially expand by inducing foreshortening.

As a further alternative, the support structure (or portions thereof) may be self-expanding, such as by being formed of a resilient or shape memory material that is adapted to transition from a relatively long tubular member having a relatively small cross-sectional dimension to a relatively shorter tubular member having a relatively larger cross-sectional dimension. In yet further alternatives, the support structure may partially self-expand by foreshortening, after which an expansion device may be used to cause further radial expansion and longitudinal foreshortening.

In another alternative embodiment, the support member comprises a multiple panel hinged ring structure. The multiple panel hinged ring structure includes a plurality of (preferably three) circumferential rings interconnected by one or more (preferably three) longitudinal posts. Each ring structure, in turn, is composed of a plurality of segments, such as curved panels, each connected to its adjacent panels by a junction member, such as a polymeric membrane hinge. The hinges are rotated to transform the structure from an expanded state for deployment, to a contracted state for delivery. A valvular body, as described elsewhere herein, is attached to the internal or external surface of the support member.

In still another alternative embodiment, the support member comprises a collapsing hinged structure. The collapsing hinged structure includes a plurality of (preferably about twenty-four) panels arranged peripherally around the generally tubular structure, each panel having a tab on its edge that overlaps and engages a mating tab on the opposed edge of the adjacent panel, interlocking the adjacent panels. An elastic membrane is attached to an external surface of adjacent panels and provides a force biasing the adjacent panels together to assist the tabs in interlocking each adjacent pair of panels. Preferably, the elastic membrane is attached to the main body of each panel, but not at the opposed edges. Thus, the tabs may be disengaged and the panels rotated to form a vertex at each shared edge, thereby defining a multi-vertex "star" shape that corresponds with the contracted state of the support member. The support member is transformed to its expanded state by applying an outward radial force that stretches the elastic membrane and allows the tabs to re-engage. A valvular body, as described elsewhere herein, is attached to the internal or external surface of the support member.

The various support members may be incorporated in a prosthetic valve, as described above, by attaching a valvular body to the external or internal surface of the support member. In the alternative, any of the foregoing support members may be utilized without a valvular body to provide a support or scaffolding function within a body lumen, such as a blood vessel or other organ. For example, the multi-segment, multi-hinged support member may be used as a scaffolding member for the treatment of abdominal aortic aneurysms, either alone, or in combination with another support member, graft, or other therapeutic device. Other similar uses are also contemplated, as will be understood by those skilled in the art.

Each of the foregoing prosthetic valves and support members is adapted to be transformed from its expanded state to its contracted state to be carried by a delivery catheter to a treatment location by way of a minimally invasive interventional procedure, as described more fully elsewhere herein.

In other aspects of the invention, delivery devices for delivering a prosthetic valve to a treatment location in a body lumen are provided, as are methods for their use. The delivery devices are particularly adapted for use in minimally invasive interventional procedures, such as percutaneous aortic valve replacements. The delivery devices include an elongated delivery catheter having proximal and distal ends. A handle is provided at the proximal end of the delivery catheter. The handle may be provided with a knob, an actuator, a slider, other control members, or combinations thereof for controlling and manipulating the catheter to perform the prosthetic valve delivery procedure. A retractable outer sheath may extend over at least a portion of the length of the catheter. Preferably, a guidewire lumen extends proximally from the distal end of the catheter. The guidewire lumen may extend through the entire length of the catheter for over-the-wire applications, or the guidewire lumen may have a proximal exit port closer to the distal end of the catheter than the proximal end for use with rapid-exchange applications.

The distal portion of the catheter includes a carrier adapted to receive and retain a prosthetic valve and to maintain the prosthetic valve in a contracted state, and to deploy the prosthetic valve at a treatment location within a body lumen. In one embodiment, the distal portion of the catheter is provided with a delivery tube having a plurality of longitudinal slots at its distal end, and a gripper having a longitudinal shaft and a plurality of fingers that extend longitudinally from the distal end of the gripper. Preferably, the delivery tube has the same number of longitudinal slots, and the gripper includes the same number of fingers, as there are segments on the prosthetic valve to be delivered. The longitudinal slots on the distal end of the delivery tube are equally spaced around the periphery of the tube. Similarly, as viewed from the distal end of the gripper, the fingers are arranged in a generally circular pattern. For example, in the case of three fingers, all three are spaced apart on an imaginary circle and are separated from each other by approximately 120°. In the case of four fingers, the fingers are separated from each other by approximately 90°, and so on. The spacing and orientation of the longitudinal slots and fingers may vary from these preferred values while still being sufficient to perform the delivery function in the manner described herein. The gripper is slidably and rotatably received within the delivery tube, and the delivery tube is internal of the outer sheath. The outer sheath is retractable to expose at least the longitudinal slots on the distal portion of the delivery tube. The gripper is able to be advanced at least far enough to extend the fingers distally outside the distal end of the delivery tube.

In alternative embodiments of the above delivery device, the gripper fingers may comprise wires, fibers, hooks, sleeves, other structural members extending distally from the distal end of the gripper, or combinations of any of the foregoing. As described below, a primary function of the fingers is to retain a prosthetic valve on the distal end of the gripper, and to restrain segments of the support member of the valve in an inverted state. Accordingly, any of the above (or other) structural members able to perform the above function may be substituted for the fingers described above.

An optional atraumatic tip or nosecone may be provided at the distal end of the device. The tip is preferably formed of a relatively soft, elastomeric material and has a rounded to conical shape. A central lumen is provided in the tip to allow passage of the guidewire. The shape and physical properties of the tip enhance the ability of the delivery device to safely pass through the vasculature of a patient without damaging vessel walls or other portions of the anatomy. In addition, the atraumatic tip may enhance the ability of the distal portion of the device to cross the native heart valve when the leaflets of the native valve are fully or partially closed due to calcification from disease or other disorder.

The delivery device is particularly adapted for use in a minimally invasive surgical procedure to deliver a multi-segment prosthetic valve, such as those described above, to a body lumen. To do so, the prosthetic valve is first loaded into the delivery device. In the case of a prosthetic valve having a three segment support member, the delivery tube will have three longitudinal slots at its distal end, and the gripper will be provided with three fingers. The prosthetic valve is loaded into the delivery device by first inverting the three segments to produce a three vertex structure. Inverting of the prosthetic valve segments may be performed manually, or with the aid of a tool. The prosthetic valve is then placed onto the distal end of the gripper, which has been previously extended outside the distal end of the delivery tube, with each of the three fingers retaining one of the inverted segments in its inverted position. The gripper and fingers, with the prosthetic valve installed thereon, are then retracted back into the delivery tube. During the retraction, the gripper and fingers are rotationally aligned with the delivery tube such that the three vertices of the prosthetic valve align with the three longitudinal slots on the distal end of the delivery tube. When the gripper and fingers are fully retracted, each of the three vertices of the prosthetic valve extends radially outside the delivery tube through the longitudinal slots. The gripper is then rotated relative to the delivery tube (or the delivery tube rotated relative to the gripper), which action causes each of the folded segments of the prosthetic valve to engage an edge of its respective delivery tube slot. Further rotation of the gripper relative to the delivery tube causes the folded segments to curl back toward the longitudinal axis of the prosthetic valve internally of the delivery tube, creating three lobes located fully within the delivery tube. The prosthetic valve is thereby loaded into the delivery device. The outer sheath may then be advanced over the distal portion of the catheter, including the delivery tube, to prepare the delivery device for use.

The prosthetic valve is delivered by first introducing a guidewire into the vascular system and to the treatment location of the patient by any conventional method, preferably by way of the femoral artery. Optionally, a suitable introducer sheath may be advanced to facilitate introduction of the delivery device. The delivery catheter is then advanced over the guidewire to the treatment location. The outer sheath is then retracted to expose the delivery tube. The gripper is then rotated relative to the delivery tube (or the delivery tube rotated relative to the gripper), thereby causing the folded segments of the prosthetic valve to uncurl and to extend radially outward through the longitudinal slots of the delivery tube. The delivery tube is then retracted (or the gripper advanced) to cause the prosthetic valve (restrained by the fingers) to advance distally out of the delivery tube. The gripper is then retracted relative to the prosthetic valve, releasing the prosthetic valve into the treatment location. Preferably, the inverted segments then revert to the expanded state, causing the valve to lodge against the internal surface of the body lumen (e.g., the aortic valve root or another biologically acceptable aortic position). Additional expansion of the prosthetic valve may be provided, if needed, by a suitable expansion member, such as an expansion balloon or an expanding mesh member (described elsewhere herein), carried on the delivery catheter or other carrier.

In another embodiment of the delivery device, the distal portion of the catheter includes a restraining sheath, an orientation sheath, a plurality of grippers, an expander, and a plurality of struts. An optional atraumatic tip or nosecone, as described above, may also be fixed to the distal end of the device. Each of the grippers includes a wire riding within a tube, and a tip at the distal end of the tube. The wire of each gripper is adapted to engage the vertex of a prosthetic valve support member having multiple segments, and to selectively restrain the prosthetic valve in a contracted state. The expander is adapted to selectively cause the grippers to expand radially outwardly when it is actuated by the user by way of an actuator located on the handle.

The prosthetic valve may be loaded into the delivery device by contracting the prosthetic valve (either manually or with a tool) by inverting each panel and then attaching each vertex to a respective gripper on the delivery device. The grippers receive, retain, and restrain the prosthetic valve in its contracted state. The gripper assembly having the prosthetic valve installed is then retracted into each of the orientation sheath and the restraining sheath to prepare the device for insertion into the patient's vasculature. The device is then advanced over a guidewire to a treatment location, such as the base annulus of the native aortic valve or another biologically acceptable aortic position (e.g., a location in the ascending or descending aorta). The restraining sheath is then retracted to allow the prosthetic valve to partially expand (e.g., to about 85% of its full transverse dimension), where it is constrained by the orientation sheath. The prosthetic valve is then finally positioned by manipulation of the grippers, after which the orientation sheath is retracted and the grippers released. The prosthetic valve then is fixedly engaged in the treatment location.

In yet another embodiment of the delivery device, the distal portion of the catheter includes one or more restraining tubes having at least one (and preferably two) adjustable restraining loops. The restraining tube(s) extend distally from a catheter shaft out of the distal end of the delivery device, and each restraining loop is a wire or fiber loop that extends transversely from the restraining tube. Each restraining loop is a flexible loop capable of selectively restraining a contracted prosthetic valve. The restraining loop may be selectively constricted or released by a control member, such as a knob, located on the handle of the device, or by another external actuation member. An optional retractable outer sheath may be provided to cover the distal portion of the catheter. Additionally, an optional atraumatic tip or nosecone, as described above, may be provided at the distal end of the device.

The prosthetic valve may be loaded onto the delivery device by contracting the prosthetic valve (either manually or with a tool) into its contracted state, for example, by inverting each panel and curling each inverted panel into a lobe. The contracted prosthetic valve is then placed onto the restraining tube(s) and through the one or more restraining loops. The loops are constricted around the contracted prosthetic valve, thereby restraining the prosthetic valve in its contracted state. The optional outer sheath may then be advanced over the prosthetic valve and the restraining tube(s) to prepare the delivery device for use. The device is then advanced over a guidewire to a treatment location, such as the base annulus of the native aortic valve or another biologically acceptable aortic position (e.g., a location in the ascending or descending aorta). The restraining sheath is then retracted to expose the contracted prosthetic valve. The restraining loops are released, such as by rotating the control knob, thereby releasing the prosthetic valve and allowing it to self-expand. The prosthetic valve is thereby fixedly engaged in the treatment location. An expansion member may be advanced to the interior of the prosthetic valve (or retracted from distally of the valve) and expanded to provide additional expansion force, if needed or desired.

In each of the foregoing device delivery methods, the user is able to deploy the device in a careful, controlled, and deliberate manner. This allows the user to, among other things, pause the delivery procedure and reposition the device if needed to optimize the delivery location. This added degree of control is a feature that is not available in many of the previous percutaneous device delivery methods.

In another aspect of the invention, an expansion member is provided for performing dilation functions in minimally invasive surgical procedures. For example, the expansion member may be used in procedures such as angioplasty, valvuloplasty, stent or other device placement or expansion, and other similar procedures. In relation to the devices and methods described above and elsewhere herein, the expansion member may be used to provide additional expansion force to the support members used on the prosthetic valves described herein.

In one embodiment, the expansion member comprises a plurality of inflation balloons oriented about a longitudinal axis. Each inflation balloon is connected at its proximal end by a feeder lumen to a central lumen that provides fluid communication between the inflation balloons and a source of inflation media associated with a handle portion of a catheter. The central lumen itself is provided with a guidewire lumen to allow passage of a guidewire through the expansion member. A flexible member is attached to the distal end of each of the inflation balloons, and also includes a guidewire lumen. In a preferred embodiment, the expansion member includes three inflation balloons, although fewer or more balloons are possible. The balloons may each be inflated individually, all together, or in any combination to obtain a desired force distribution. The multiple inflation balloon structure provides a number of advantages, including the ability to provide greater radial forces than a single balloon, and the ability to avoid occluding a vessel undergoing treatment and to allow blood or other fluid to flow through the device.

In an alternative embodiment, the expansion member comprises a flexible, expandable mesh member. The expandable mesh member includes a shaft and a cylindrical woven mesh member disposed longitudinally over the shaft. A distal end of the cylindrical mesh member is attached to the distal end of the shaft. The proximal end of the cylindrical mesh member is slidably engaged to the shaft by a collar proximally of the distal end. As the collar is advanced distally along the shaft, the body of the cylindrical mesh member is caused to expand radially, thereby providing a radially expansion member. Alternatively, the proximal end of the mesh member may be fixed to the shaft and the distal end may have a collar engagement allowing it to advance proximally along the shaft to cause the mesh member to expand radially. Still further, each of the proximal and distal ends of the mesh member may be slidably engaged to the shaft, and each moved toward the other to cause radial expansion.

Other aspects, features, and functions of the inventions described herein will become apparent by reference to the drawings and the detailed description of the preferred embodiments set forth below.

DETAILED DESCRIPTION OF THE PREFERRED EMBODIMENTS

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present inventions.

A. Prosthetic Valves and Related Apparatus

Figure 1A:
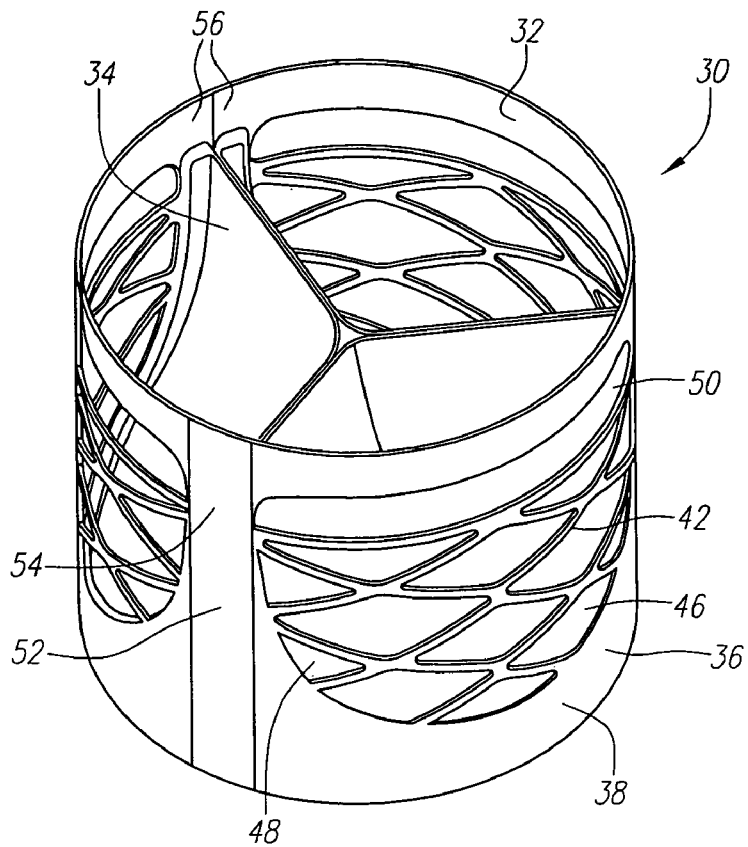
FIG. 1A is a perspective view of a prosthetic valve in accordance with the present invention.

Turning first to FIG. 1A, an embodiment of a prosthetic valve is shown. The prosthetic valve 30 is particularly adapted for use as a replacement aortic valve, but may be used for other indications as well. As shown, the prosthetic valve 30 includes a generally cylindrical support member 32 and a valvular body 34 attached to the internal surface of the support member. Although a generally cylindrical support member is shown, support members having other than circular cross-sectional shapes, such as oval, elliptical, or irregular, may also be provided depending upon the nature of the treatment location and environment in which the prosthetic valve or the support structure are intended to be used.

The support member in the embodiment shown in FIG. 1A is made up of three generally identical curved panels 36, with each panel spanning approximately 120° of the circular cross-section of the support member. (As noted elsewhere herein, the panels need not be generally identical in terms of size, materials, thickness, or other properties.) Each panel 36 includes a frame 38 and a semi-circular aperture 40 extending over a large portion of the central portion of the panel. The aperture 40 includes a number of interconnecting braces 42 extending across the breadth of the aperture, thereby defining a number of sub-apertures 44 between the braces. The braces define several diamond-shaped sub-apertures 46, partial diamond-shaped sub-apertures 48, and an elongated sub-aperture 50. Apertures and sub-apertures of different shapes and sizes than those shown in the FIG. 1A embodiment are also possible. For example, in the alternative support member embodiment shown in FIG. 1B, a single semi-circular aperture 40 is provided, with no braces and no sub-apertures. Alternatively, a panel may comprise a solid member having no apertures or sub-apertures.

The panels of the support member are typically the portion of the structure that engages the internal surface of the lumen at the treatment location. In the case of a prosthetic heart valve, among other functions, the panels physically engage and displace the leaflets of the native valve. The panels are also the primary portion of the structure that is in physical engagement with the body lumen and that is holding the structure in place and preventing migration. Therefore, the materials and structure of the panels are adapted, at least in part, to perform these functions. In some instances, a large aperture may be preferred, in other cases a particular bracing structure may be preferred, while in still other cases it is preferable not to have any apertures or bracing. These features may be varied to provide desired performance, depending upon the anatomical environment.

Each of the panels shown, and those described elsewhere herein, is preferably formed from a sheet of resilient, biocompatible material, such as stainless steel, other metals or metal alloys, resilient polymers such as plastics, or other suitable materials conventionally used for implantable medical devices. In a preferred embodiment, the panels are formed from a super-elastic shape-memory material, such as nitinol or other similar metal alloys. The panels may be molded, extruded, etched, cut, stamped or otherwise fabricated from sheets of material, or manufactured in other ways known to those skilled in the art.

Although the support member embodiment shown in FIG. 1A includes three panels, those skilled in the art will recognize that fewer or more panels may be incorporated into the support member. For example, a two panel structure may be employed, or structures having four, five, or many more panels. Alternatively, a structure may be provided having non-panel segments, such as beams, braces, struts, or other structural members extending between the foldable junctions provided on the support member. Any of these (or any other) alternative structures, or any combinations thereof, may be provided as one or more segments of the support member, provided that the structure is capable of providing the physical and structural characteristics needed to support the prosthetic valve in its intended function.

In addition, although each of the segments making up a support member may be identical to the other segments, it is also possible to provide segments having different physical properties. For example, in a multi-panel support member, the panels may be made up of different materials, or one or more panels may have a different size or thickness than the other panel(s), or the physical properties between the different panels may be altered in some other manner. This may be done, for example, as an accommodation for the treatment location in which the prosthetic valve is to be placed. The wall thickness of the aortic root, for example, varies around its circumference. Thus, desirable results may be obtained by providing a support member having a first panel that provides greater structural strength (or resistance to collapse) than the other panels. Other variations are also possible.

Turning again to FIG. 1A, a hinge 52 is provided at the junction formed between each pair of adjacent panels. In the embodiment shown in FIG. 1A, the hinge is a membrane hinge comprising a thin sheet of elastomeric material 54 attached to the external edge 56 of each of a pair of adjacent panels 36. In the expanded state of the support member, as shown in FIG. 1A, the membrane hinge maintains the side-to-side orientation of each pair of adjacent panels, preventing any significant amount of slipping or sliding between the panels. As described more fully below, the hinge 52 is also foldable so as to allow the panels 36 to invert and the edges 56 to fold together to form a vertex. The ability of the hinge (or other foldable junction member) to allow adjacent panels to invert and fold against each other at adjacent edges is a substantial feature in creating a contracted state for the support member, and the prosthetic valve. In addition, the hinge 52 (or other foldable junction) preferably is adapted to allow the support member 32 to physically conform to the internal surface of the body lumen at the treatment location.

Figure 1B:
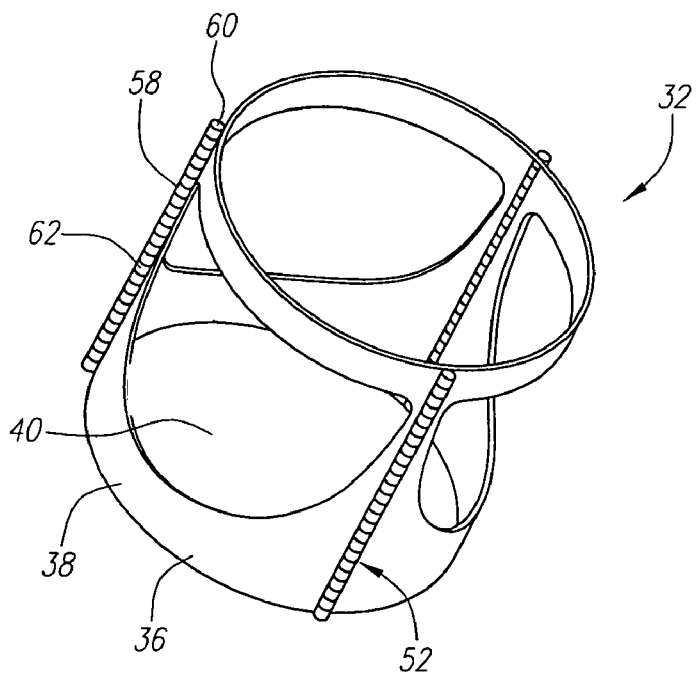
FIG. 1B is a perspective view of a support member in accordance with the present invention.
Figure 4A:
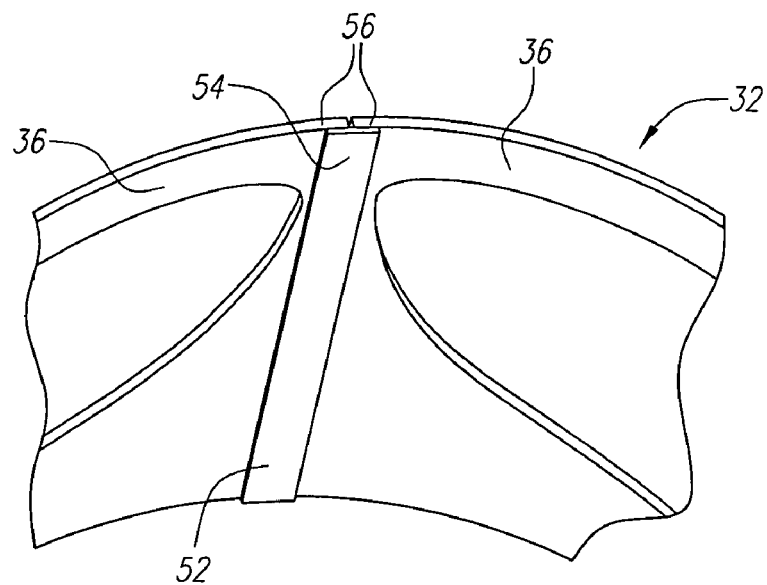
FIG. 4A is a perspective view illustrating a hinge connecting two panels of a support member.
Figure 4B:
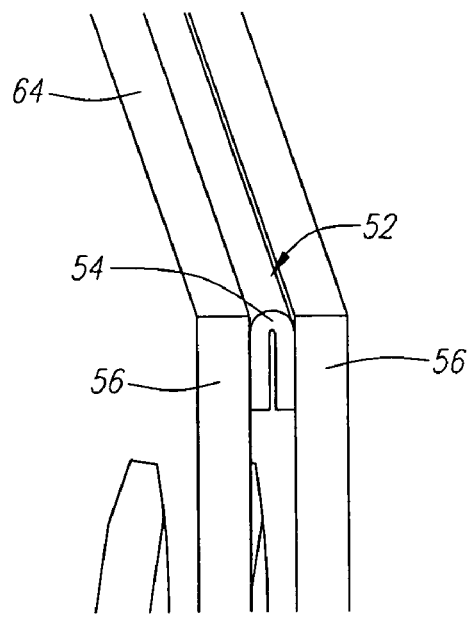
FIG. 4B is a perspective view of the hinge shown in FIG. 4A, illustrating the hinge in is folded state.
Figure 4C:
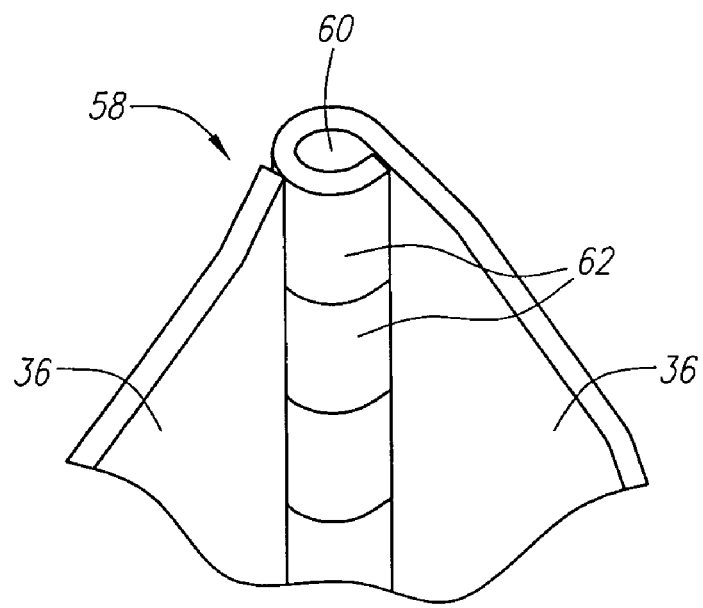
FIG. 4C is a perspective view of another hinge connecting two panels of a support member.
Figure 4D:
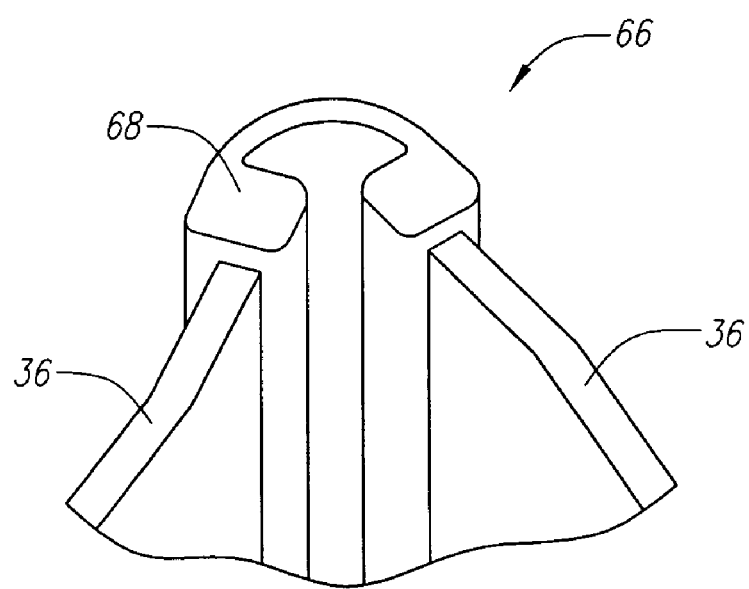
FIG. 4D is a perspective view of another hinge connecting two panels of a support member.
Figure 5A:
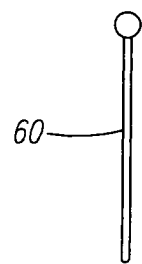
FIG. 5A is a perspective view of a support member having inverted panels, illustrating removable hinge pins.
Figure 5A:
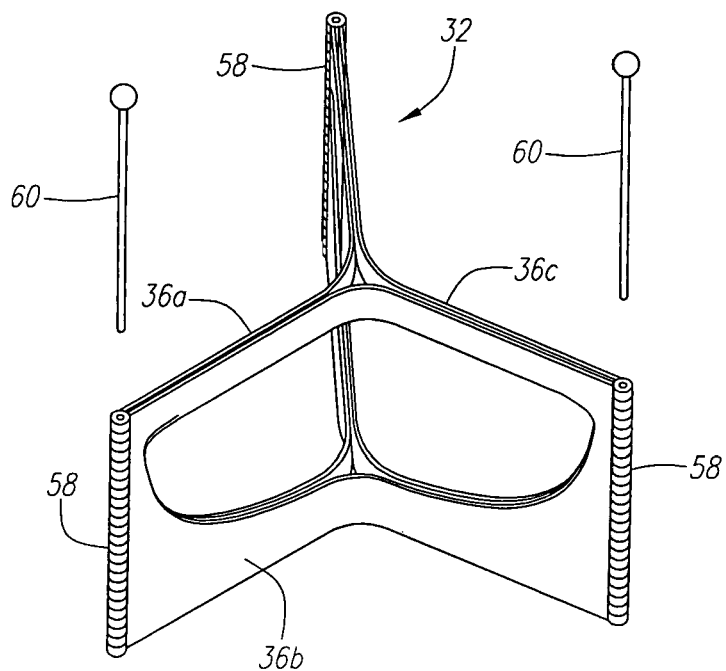

As noted below and elsewhere, various types of hinges and other foldable junctions may be used in alternative embodiments. For example, and without intending to otherwise limit the descriptions contained herein, other types of hinges that may be used include standard piano hinges, living hinges, and other types of mechanical hinges. See, for example, the support member 32 shown in FIG. 1B, in which each pair of adjacent panels 36 is connected by a standard piano hinge 58, i.e., a long, narrow hinge with a pin 60 running the entire length of its joint that interconnects meshed sets of knuckles 62 formed on the edge of each of the pair of adjacent panels 36. Several other alternative hinge structures are shown in FIGS. 4A-D, in which FIGS. 4A-B show another membrane hinge in which the elastomeric strip 54 is attached to each of a pair of adjacent panels 36 on the internal surface of the support member 32. FIG. 4A shows a portion of the support structure 32 in its expanded state, and FIG. 4B shows the portion of the structure after the pair of adjacent panels 36 have been folded against each other at the membrane hinge 52, thereby forming a vertex 64. FIG. 4C shows a close-up view of another standard piano hinge 58 design, similar to that shown in FIG. 1B, showing the pin 60 and the meshing knuckles 62 formed on the edge of each of the pair of adjacent panels 36. FIG. 4D shows a living hinge 66 that includes a flexible (e.g., elastomeric) hinge member 68 that is attached to each of the pair of adjacent panels 36 and that extends the length of the junction between the panels. In addition, FIG. 5A shows another support member (in a partially contracted condition) illustrating removable hinge pins.

Several alternative foldable junctions may also be used instead of hinges. For example, a section of a sheet may be etched, scored, or otherwise thinned relative to the adjacent portions of the device to provide a weakened section that allows inversion and folding of a pair of adjacent segments of the sheet, thereby providing a foldable junction. Other alternative foldable junctions are also contemplated, and will be understood by persons of skill in the art, to be suitable for use in the support members described herein.

Optionally, the foldable junction may be provided with a lock-out feature that allows the foldable junction to fold in a direction that allows adjacent panels to invert, as described herein, but that prevents the foldable junction from folding in the opposite direction. For example, a standard piano hinge may be constructed in a manner that provides only about 180° of rotation in a conventional manner, and attached to a pair of adjacent panels such that inward rotation is allowed, but outward rotation is prevented. Other suitable lock-out mechanisms may be possible, as will be recognized by those of skill in the art.

In addition, although the hinges and other foldable junctions are preferably oriented uniformly vertically (i.e., parallel to the longitudinal axis of the support member) on the periphery of the support member, other orientations are possible. For example, the hinges may be oriented horizontally (i.e., transverse) relative to the longitudinal axis, they may be oriented diagonally relative to the longitudinal axis, they may have a zig-zag or spiral orientation, or they may take on any geometric or irregular pattern.

Returning again to FIG. 1A, the valvular body 34 of the embodiment shown in the figure is a flexible artificial tissue multi-leaflet structure. The artificial tissue includes a unitary polymer material or a composite of polymer overlaid onto a flexible substrate, which may be in the form of a mesh. The polymer material is any suitable flexible, biocompatible material such as those conventionally used in implantable medical devices. Preferably, the polymer material is polyurethane or another thermoplastic elastomer, although it is not limited to such materials. The material comprising the flexible mesh is preferably a flexible, shear-resistant polymeric or metallic material, such as a polyester or very fine metallic (e.g., stainless steel) mesh. The valvular body is described more fully below in relation to FIGS. 8A-B.

In other embodiments, the valvular body may be formed of human tissue, such as homografts or autografts, or animal tissue, such as porcine, bovine, or equine tissue (e.g., pericardial or other suitable tissue). The construction and preparation of prosthetic tissue valvular bodies is beyond the scope of the present application, but is generally known to those of skill in the art and is readily available in the relevant technical literature.

The prosthetic valves described herein have an expanded state that the prosthetic valve takes on when it is in use. The FIG. 1A illustration shows a prosthetic valve 30 in its expanded state. In the expanded state of the prosthetic valve, the support member is fully 32 extended in its cylindrical (or alternative) shape, with each hinge 52 (or other foldable junction) in its extended, or non-folded state. As described previously, in the expanded state, the support member 32 preferably has a cross-sectional dimension (e.g., diameter) that is from about 0 to about 25% larger than that of the body lumen or other treatment location. Once deployed, the support member extends to its full cross-sectional dimension—i.e., it does not compress radially due to the radial force imparted by the lumen or other tissue. Rather, the support member will expand the cross-sectional dimension of the lumen or other tissue at the treatment location. In this way, the support member reduces the possibility of fluid leakage around the periphery of the device. In addition, due to the strength of the interference fit that results from the construction of the device, the support member will have proper apposition to the lumen or tissue to reduce the likelihood of migration of the device once deployed. The present prosthetic valves also have a contracted state that is used in order to deliver the prosthetic valve to a treatment location with the body of a patient. The contracted state generally comprises a state having a smaller transverse dimension (e.g., diameter) relative to that of the expanded state. The contracted states of several of the prosthetic valve embodiments described herein are discussed below.

Figure 2A:
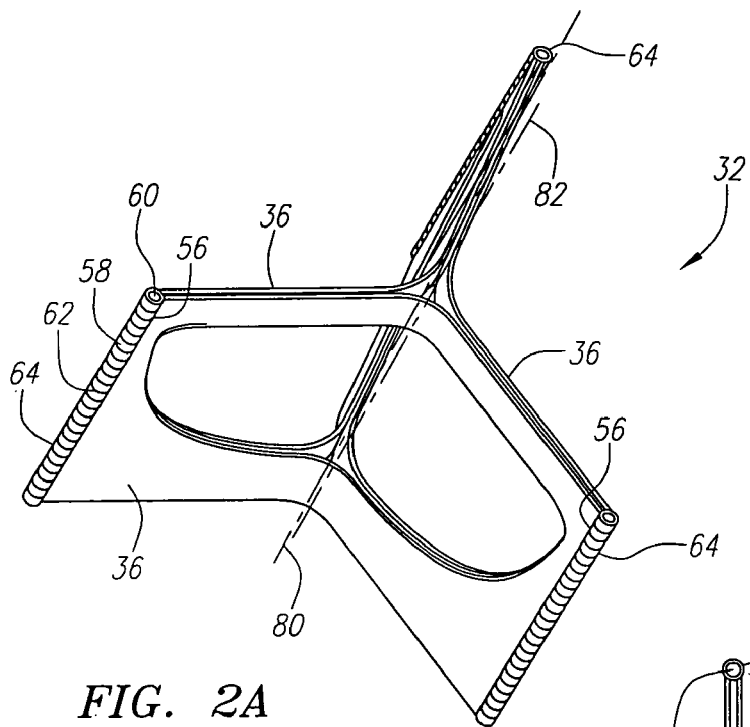
FIG. 2A is a perspective view of a support member having illustrating inverted panels.
Figure 2B:
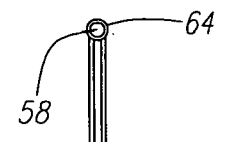
FIG. 2B is a top view of the support member of FIG. 2A.
Figure 2C:
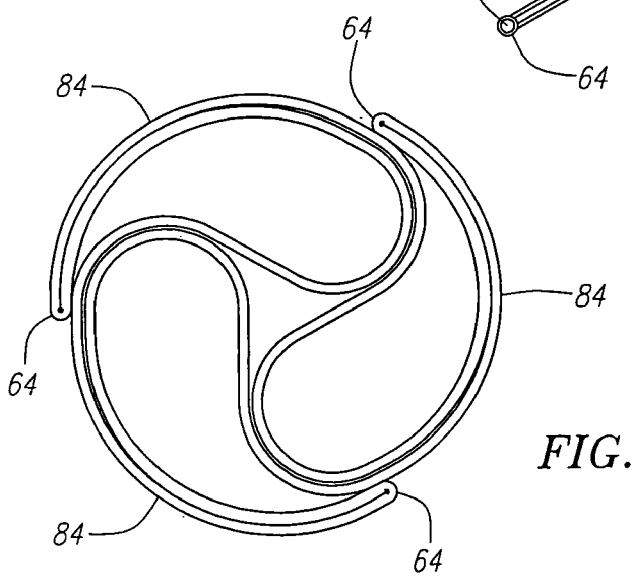
FIG. 2C is a top view of a support member in a contracted state.

Turning to FIGS. 2A-C, a method for transforming a prosthetic valve from its expanded state to its contracted state is illustrated. These Figures show a three-panel support member without a valvular body attached. The method for contracting a full prosthetic valve, including the attached valvular body, is similar to that described herein in relation to the support member alone.

As shown in FIGS. 2A-B, each of the panels 36 is first inverted, by which is meant that a longitudinal centerline 80 of each of the panels is forced radially inward toward the central longitudinal axis 82 of the support member. This action is facilitated by having panels formed of a thin, resilient sheet of material having generally elastic properties, and by the presence of the hinges 58 located at the junction between each pair of adjacent panels 36. During the inversion step, the edges 56 of each of the adjacent pairs of panels fold upon one another at the hinge 58. The resulting structure, shown in FIGS. 2A-B, is a three-vertex 64 star shaped structure. Those skilled in the art will recognize that a similar procedure may be used to invert a four (or more) panel support member, in which case the resulting structure would be a four- (or more) vertex star shaped structure.

The prosthetic valve 30 may be further contracted by curling each of the vertices 64 of the star shaped structure to form a multi-lobe structure, as shown in FIG. 2C. As shown in that Figure, each of the three vertices 64 is rotated toward the center longitudinal axis of the device, causing each of the three folded-upon edges of the adjacent pairs of panels to curl into a lobe 84. The resulting structure, illustrated in FIG. 2C, is a three-lobe structure that represents the fully contracted state of the prosthetic valve. Manipulation and use of the fully contracted device is described more fully below. Those skilled in the art will recognize that a similar procedure may be used to fully contract a four (or more) panel support member, in which case the resulting structure would be a four- (or more) lobed structure.

In the case of a two panel support member, the support member may be contracted by first inverting one of the two panels to cause it to come into close relationship with the other of the two panels to form a nested panel structure. The pair of nested panels is then rolled into a small diameter tubular member, which constitutes the contracted state of the two-panel support member.

Turning to FIGS. 3A-I, another embodiment of a support member suitable for use in a prosthetic valve is shown. This embodiment is structurally similar to the preceding embodiment, but is capable of being transformed to a contracted state in a different manner than that described above. The embodiment includes three panels 36, each having a semi-circular aperture 40. A standard piano hinge 58 is provided at two of the junctions between adjacent pairs of panels. (See FIG. 3B). The third junction does not have a hinge, instead having a locking member 90. In the embodiment shown, the locking member includes a tab 92 attached to each of the top and bottom portions of the edge of the first 36a of a pair of adjacent panels, and a slot 94 provided along both the top and bottom edges of the second 36b of the pair adjacent panels. (See FIG. 3C). The tabs 92 on the first panel 36a are able to extend through and ride in the slots 94 on the second panel 36b, thereby allowing the first panel 36a to slide relative to the second panel 36b while remaining physically engaged to the panel, and then to slide back to the original position. A locking tab 96 may be provided on the second panel 36b to selectively lock the first panel tab 92 in place in the slot 94.

Figure 3A:
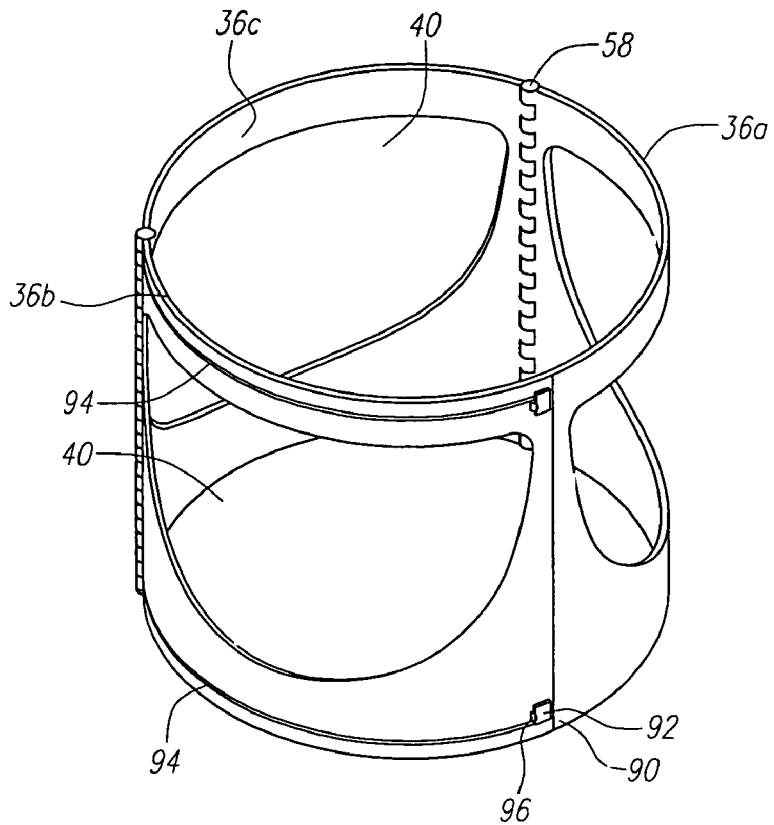
FIG. 3A is a perspective view of another support member in accordance with the present invention.
Figure 3B:
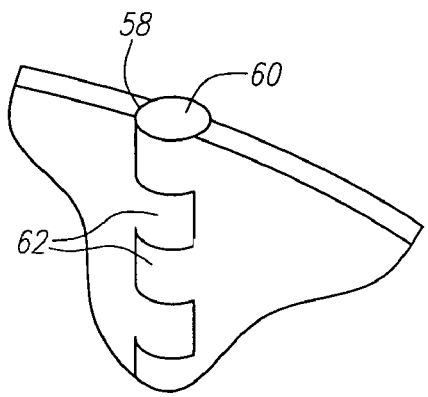
FIG. 3B is a close-up view of a hinge on the support member of FIG. 3A.
Figure 3C:
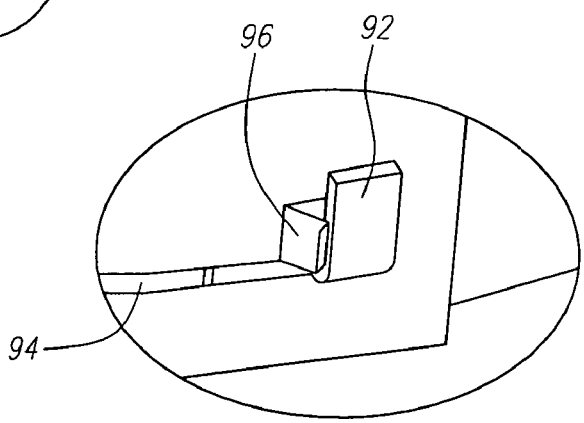
FIG. 3C is a close-up view of an locking tab and slot on the support member of FIG. 3A.
Figure 3D:
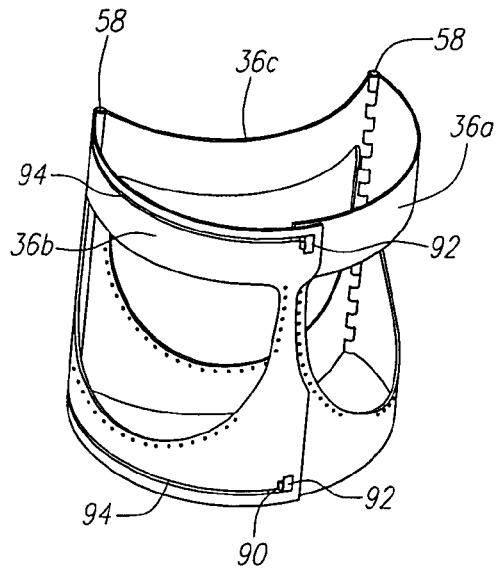
FIG. 3D is a perspective view of the support member shown in FIG. 3A, illustrating inversion of a panel.
Figure 3E:
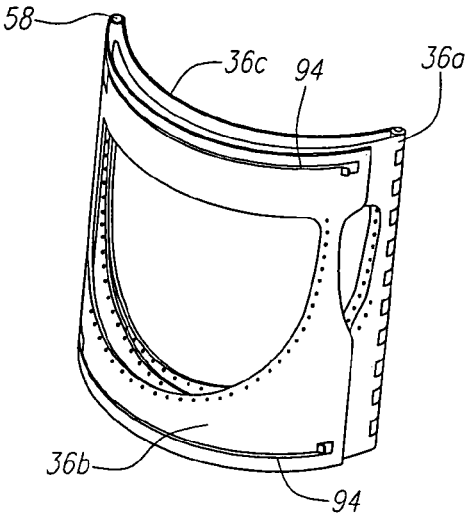
FIG. 3E is a perspective view of the support member shown in FIG. 3A, illustrating a nested arrangement of the three panels.
Figure 3F:
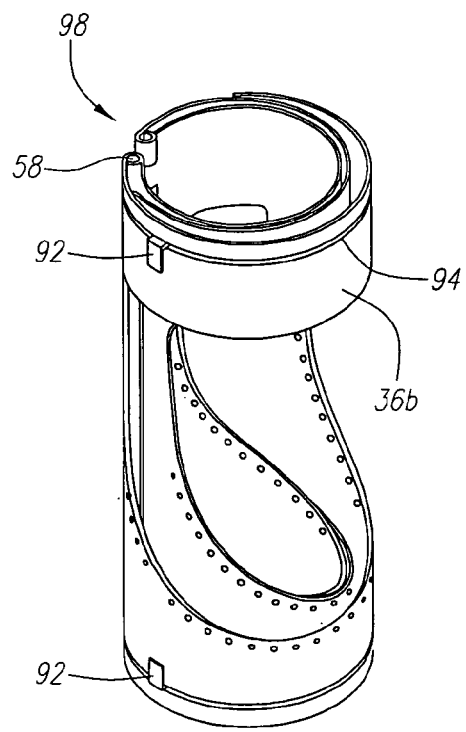
FIG. 3F is a perspective view of the support member shown in FIG. 3A, illustrating a contracted state of the support member.
Figure 3G:
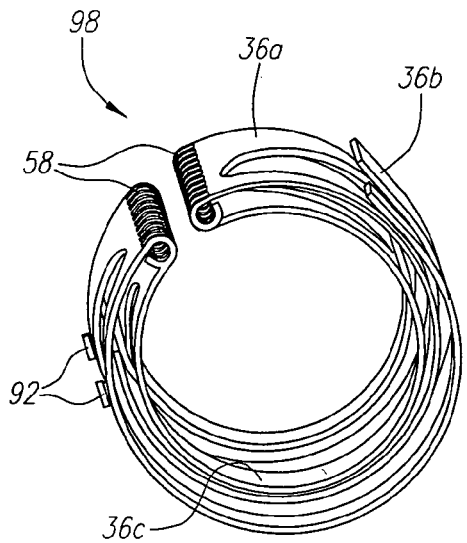
FIG. 3G is an end view of the support member shown in FIG. 3A, illustrating a contracted state of the support member.

FIGS. 3D-G illustrate the manner in which the preceding support member is transformed to its contracted state. As shown in FIG. 3D, the panel 36c situated opposite the locking junction 90 is inverted while leaving the other two panels 36a-b in their uninverted state. The tabs 92 on the first panels 36a are then slid along the slots 94 in the second panel 36b, causing the first and second panels 36a-b to come into a nested arrangement behind the inverted panel 36c, with the first panel 36a nested between the inverted panel 36c and the second panel 36b. (See FIG. 3E). The nested panels are then able to be curled into a relatively small diameter tubular member 98, as shown in FIGS. 3F and 3G, which constitutes the contracted state of the support member.

Figure 3H:
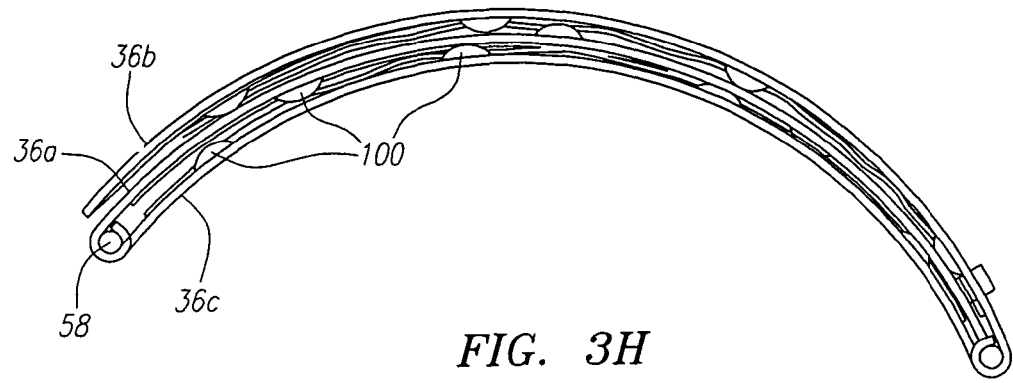
FIG. 3H is a top view of another support member, illustrating a nested arrangement of the three panels.
Figure 3I:
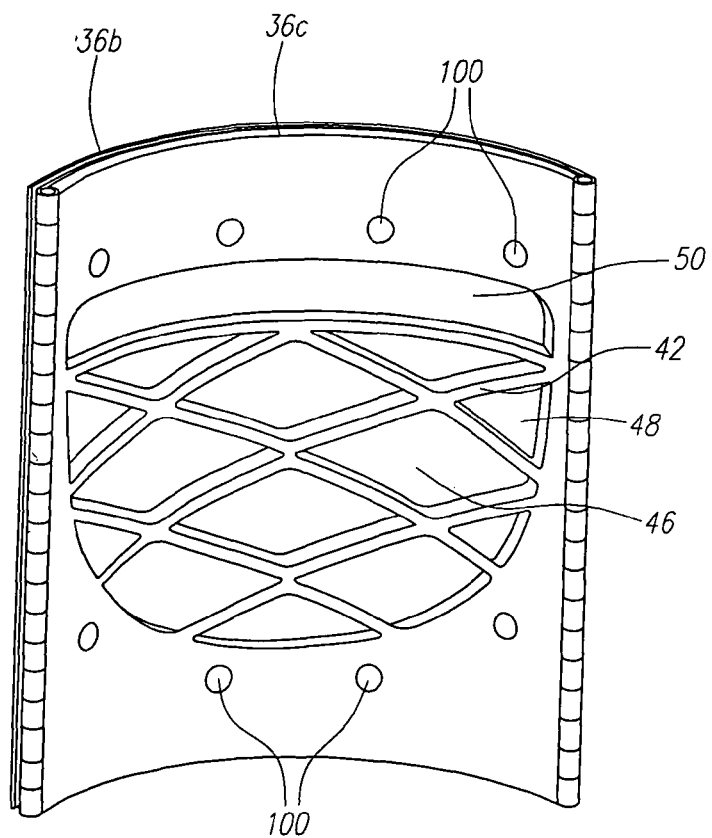
FIG. 3I is a side view of the support member shown in FIG. 3H.

FIGS. 3H-I illustrate a similar support member in its partially contracted state in which the three panels 36a-c are in the nested arrangement. The support member shown in FIGS. 3H-I also include a plurality of brace members 42 extending through the aperture 40, forming diamond-shaped sub-apertures 46, partial diamond-shaped sub-apertures 48, and an elongated sub-aperture 50. A plurality of raised surfaces 100, or bumps, are provided over the surfaces of each of the panels 36a-c to provide positive spacing for the valvular body 34 when the prosthetic valve 30 is placed in the contracted state.

The positive spacing provided by the raised surfaces 100 serve to decrease the possibility of squeezing, crimping, folding, or otherwise damaging the valvular body 34 or its constituent parts when the prosthetic valve is contracted. The raised surfaces 100 (or other spacing member) of the support member may be used on any of the embodiments of the prosthetic valves described herein.

Figure 5B:
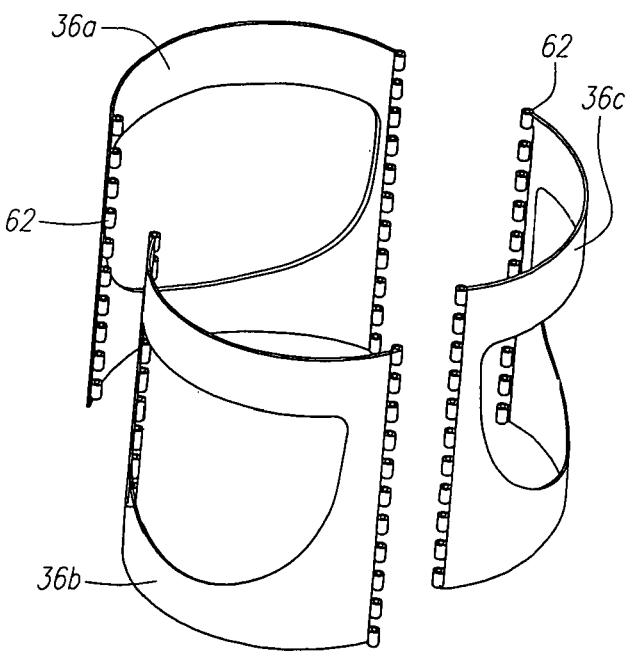
FIG. 5B is a perspective view of a support member after separation of its three panels.

Turning to FIGS. 5A-B, as described above, FIG. 5A illustrates a support member 32 having three panels 36a-c and three standard piano hinges 58 at the junctions between the three panels. The support member is shown with each of its three panels 36a-c in the inverted position. Each of the piano hinges 58 has a removable hinge pin 60. When the hinge pins 60 are removed, the panels 36a-c may be separated from each other, as illustrated in FIG. 5B. The ability to separate the panels may be used to facilitate surgical (or other) removal of the support member, or the prosthetic valve, or the panels may need to be separated for another purpose. Although piano hinges with removable hinge pins are shown in FIGS. 5A-B, alternative removable hinge structures may also be used. For example, a membrane hinge having a tearable membrane strip will facilitate removal of the support member. Further alternatives may include melting or unzipping a hinge. Other removable hinge structures are also contemplated. In each of these cases, provision of a hinge that may be easily defeated by some mechanism creates that ability for the user to more easily remove or otherwise manipulate a prosthetic valve or support member for any desired purpose.

Figure 6:
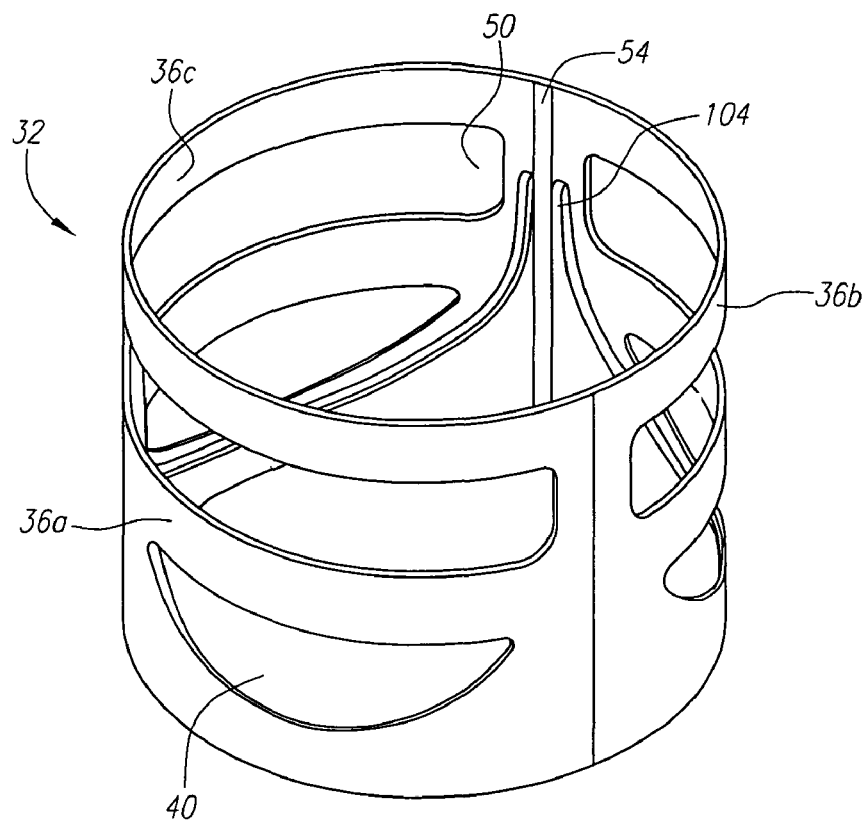
FIG. 6 is a perspective view of another support member.

FIG. 6 shows another embodiment of a support member 32 suitable for use in a prosthetic valve 30. The support member 32 includes three panels 36a-c, each panel having an elongated aperture 50 and a semi-circular aperture 40. The support member includes an elastomeric strip 54 at the foldable junction between each pair of adjacent panels, each of which forms a membrane hinge. A valvular body attachment lip 104 is attached to the interior surface of each of the panels 36a-c to facilitate attachment of the valvular body 34 to the support member 32. The attachment lip 104 may comprise a polymer material suitable for sewing, adhering, or otherwise attaching to the valvular body. The attachment lip 104 is preferably molded or adhered onto the interior surface of each of the panels of the support member. Although the attachment lip 104 facilitates one method for attaching the valvular body to the support member, it is not the only method for doing so, and use of the attachment lip 104 is optional.

Figure 7:
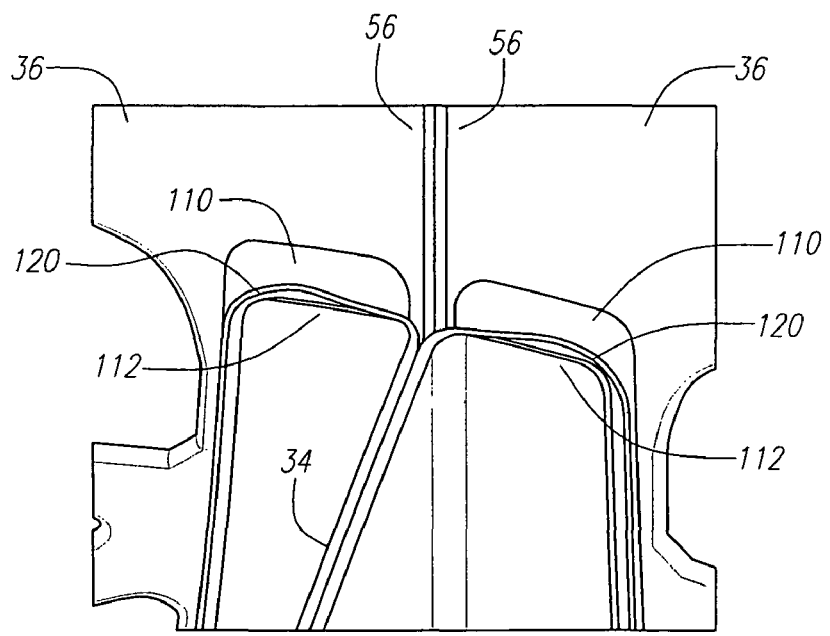
FIG. 7 is a close-up view of an attachment mechanism for attaching a valvular body to a support member.

FIG. 7 illustrates another structure and method used to attach the valvular body to the support member panels. A first strip 110 of polymeric material is adhered to the interior surface of the edge 56 of each panel. The first strip 110 of polymeric material does not need to extend along the entire edge, but generally about half of the length. The first strip 110 is adhered with any suitable adhesive material, or it may be molded directly onto the panel 36. An attachment lip 120 formed on the base portion of the valvular body is then attached to each of the first strips 110 of polymeric material. The attachment lips 120 may be formed on the base portion of the valvular body 34 in any of the embodiments described below, including those having a unitary structure or those having a composite structure. (A composite structure is shown in FIG. 7). The attachment lips 110 may be attached to the strips of polymeric material using any suitable adhesive or any other suitable method. Next, and optionally, a second strip 112 of polymer material may be attached to the exposed surface of the valvular body attachment lip 120, sandwiching the attachment lip 120 between the first 110 and second strips 112 of material.

Figure 8A:
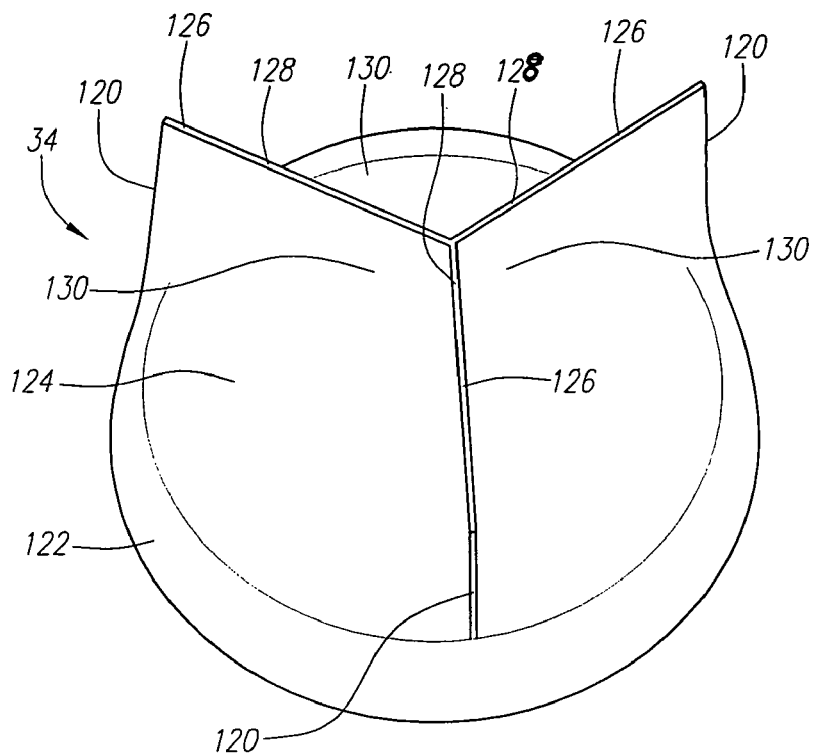
FIG. 8A is a perspective view of a valvular body.
Figure 8B:
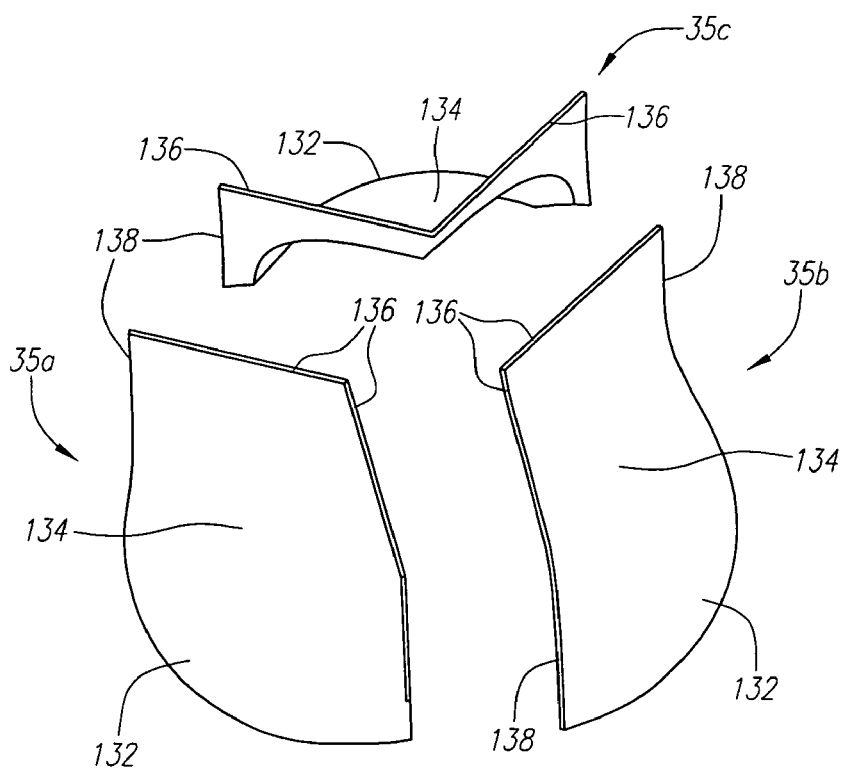
FIG. 8B is a perspective view showing separate leaflets of the valvular body of FIG. 8A.

FIGS. 8A-B show perspective views of valvular bodies suitable for use in the prosthetic valves described herein. The valvular body 34 shown in FIG. 8A is of a unitary construction, while that shown in FIG. 8B is of a composite construction, including three separate leaflets 35a-c. Turning first to the unitary structure embodiment shown in FIG. 8A, the valvular body 34 includes a generally cylindrical base portion 122 that then contracts down into a generally concave portion 124 (as viewed from the interior of the valvular body). The valvular body 34 has three lines of coaptation 126 formed on the bottom of the concave portion 124. A slit 128 is either cut or molded into each of the lines of coaptation 126 to create three valve leaflets 130 that perform the valvular fluid regulation function when the valve is implanted in a patient. An optional attachment lip 120 may be formed on the outward facing lines of coaptation 126, to facilitate attachment of the valvular body 34 to the support member in the manner described above in relation to FIG. 7.

Turning to the composite structure embodiment shown in FIG. 8B, each separate leaflet 35a-c includes a base portion 132 and a generally concave portion 134 extending from the base. Each leaflet 35a-c also includes a pair of top edges 136 and a pair of side edges 138. The top edges and side edges of each leaflet 35a-c are positioned against the top edges and side edges of each adjacent leaflet when the composite structure embodiment is attached to an appropriate support member.

As described above, in either the unitary or composite construction embodiments, the valvular body may be formed solely from a single polymer material or polymer blend, or it may be formed from a substrate having a polymer coating. The materials suitable for use as the polymer, substrate, or coating are described above. Alternatively, the valvular body may comprise human or animal tissue.

The valvular body may be attached to the support member by any suitable method. For example, the valvular body may be attached to the support member by sewing, adhering, or molding the valvular body to an attachment lip, as described above in relation to FIG. 6. Or, the valvular body may be attached to the support member using the attachment strips described above in relation to FIG. 7. Alternatively, the valvular body may be adhered directly to the support member using an adhesive or similar material, or it may be formed integrally with the support member. Other and further suitable attachment methods will be recognized by those skilled in the art.

Figure 9A:
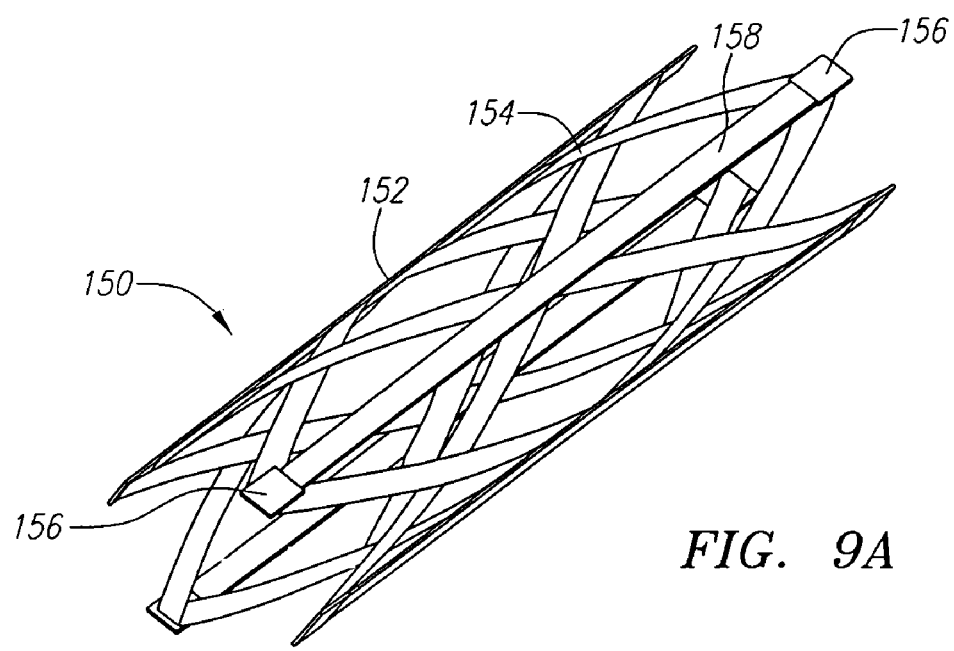
FIG. 9A is a perspective view of an axially activated support member in its contracted state.
Figure 9B:
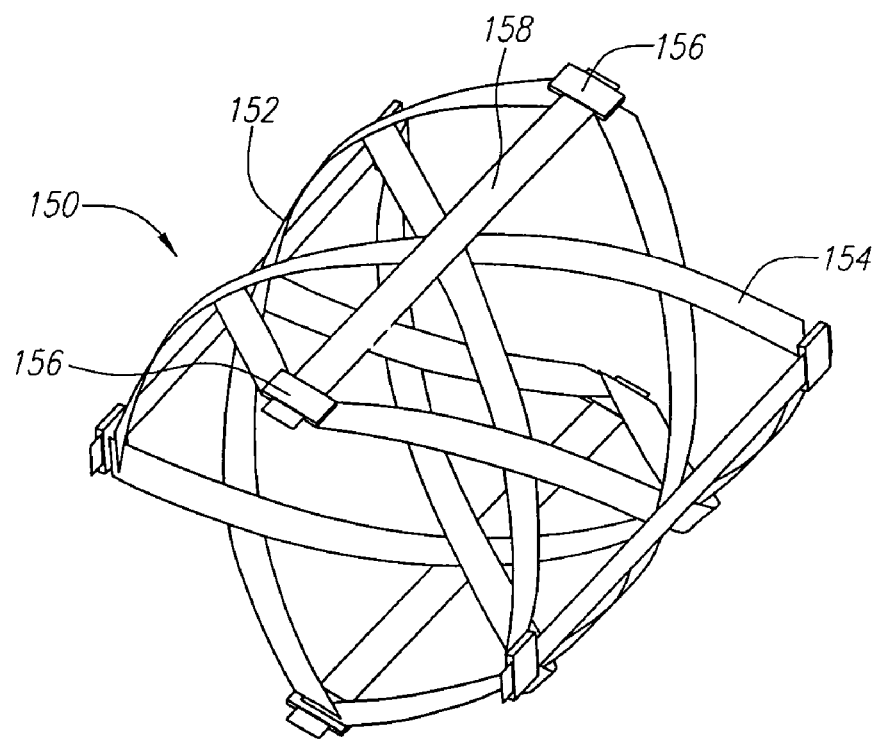
FIG. 9B is a perspective view of the axially activated support member of FIG. 9A, shown in its expanded state.

The multi-segment support member embodiments described above are suitable for use in the prosthetic valves described herein. Additional structures are also possible, and several are described below. For example, in reference to FIGS. 9A-B, an alternative support member is illustrated. The alternative support member is a tubular member that is capable of radial expansion caused by forced foreshortening. As noted earlier herein, several structures and/or methods are available that are capable of this form of transformation, one of which is described in FIGS. 9A-B. An axially activated support member 150 includes a generally tubular body member 152 formed of a matrix of flexible struts 154. In the embodiment shown in the Figures, the struts 154 are arranged in crossing pairs forming an "X" pattern, with the ends of a first crossing pair of struts being connected to the ends of a second crossing pair of struts by a band connector 156, thereby forming a generally cylindrical member. Additional generally cylindrical members are incorporated into the structure by interweaving the struts contained in the additional cylindrical member with the struts included in the first cylindrical member. An axial member 158 is connected to two opposed band connectors 156 located on opposite ends of the structure. When the axial member 158 is decreased in length, as shown in FIG. 9B, the support member 150 is expanded to a large diameter state, accompanied by a degree of lengthwise foreshortening of the support member. When the axial member 158 is increased in length, as shown in FIG. 9A, the support member 150 is contracted to a smaller diameter state, accompanied by a degree of lengthening of the support member. The expanded state may be used when the support member is deployed in a body lumen, and the contracted state may be used for delivery of the device. A valvular body, as described above, may be attached to the internal or external surface of the support member.

Figure 10A:
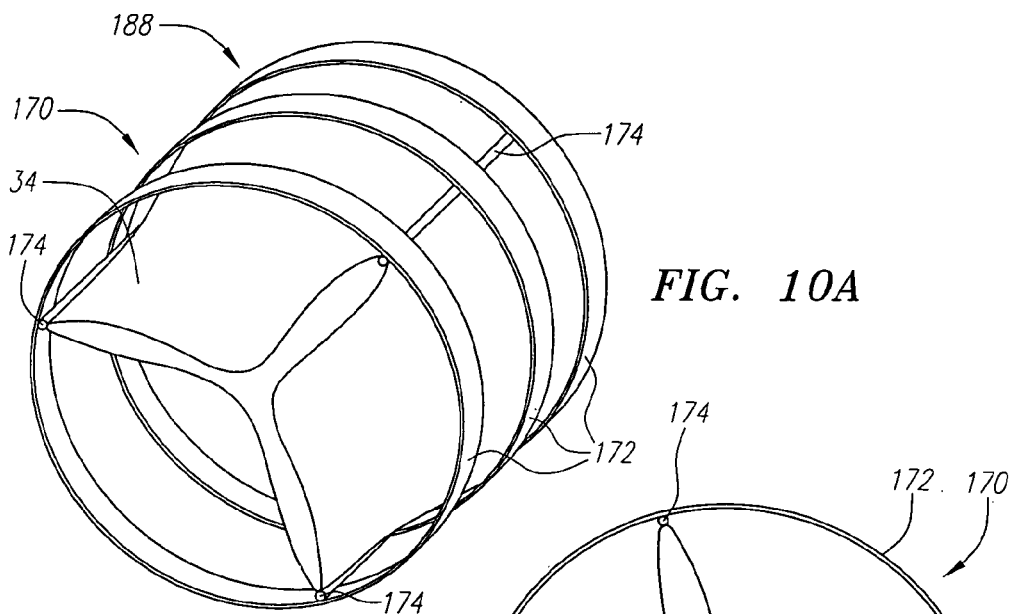
FIG. 10A is a perspective view of a multiple panel hinged ring prosthetic valve.
Figure 10B:
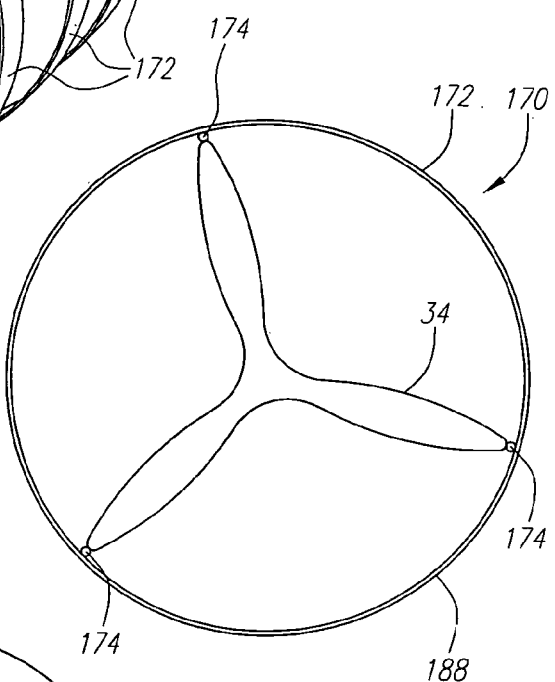
FIG. 10B is an end view of the prosthetic valve shown in FIG. 10A.
Figure 10C:
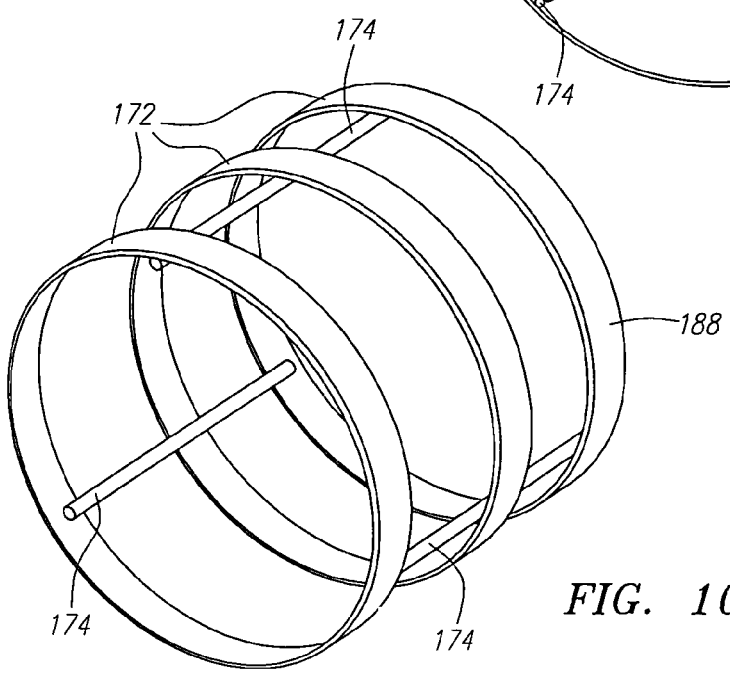
FIG. 10C is a perspective view of a multiple panel hinged ring support member.
Figure 10D:
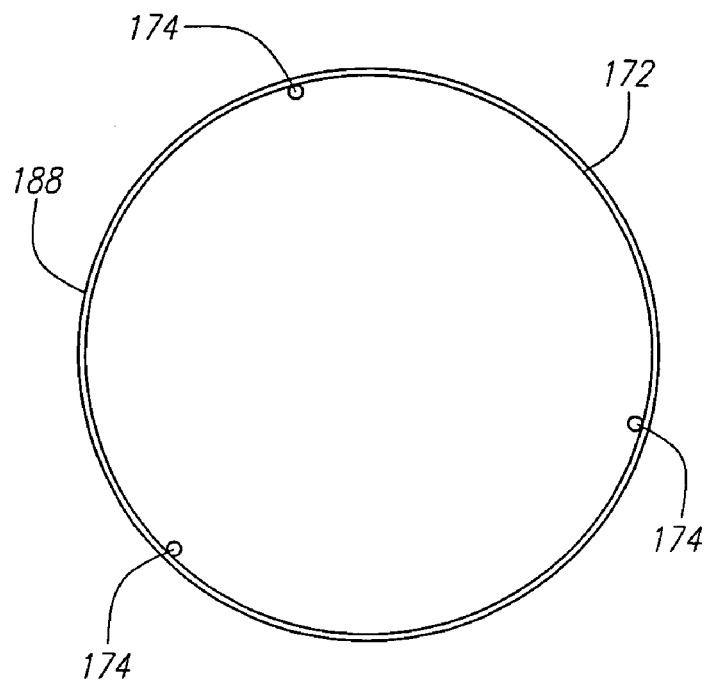
FIG. 10D is an end view of the support member shown in FIG. 10C.
Figure 10E:
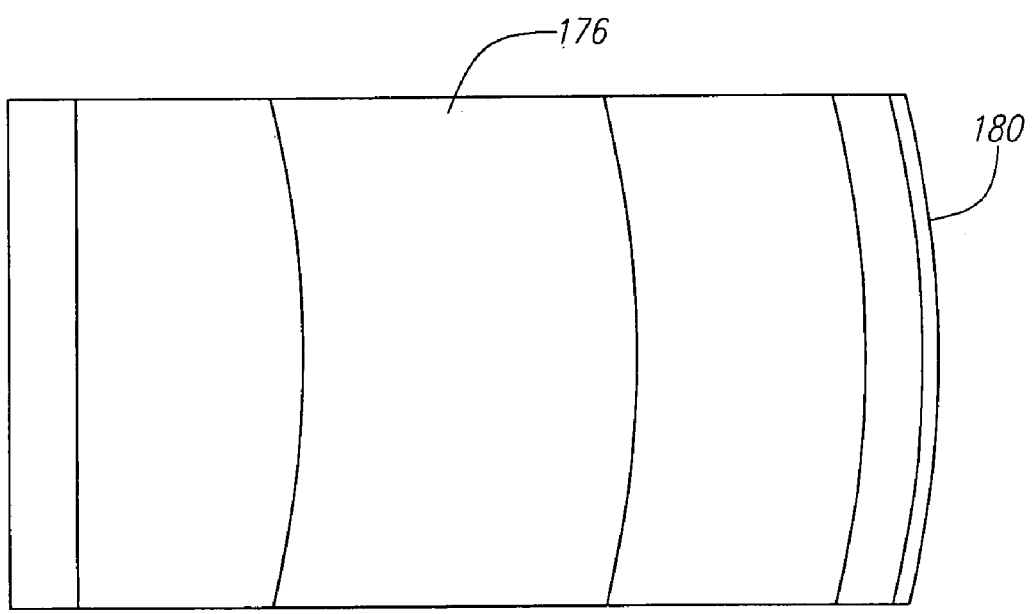
FIG. 10E is a close-up view of a panel contained on the support member shown in FIG. 10c.
Figure 10F:
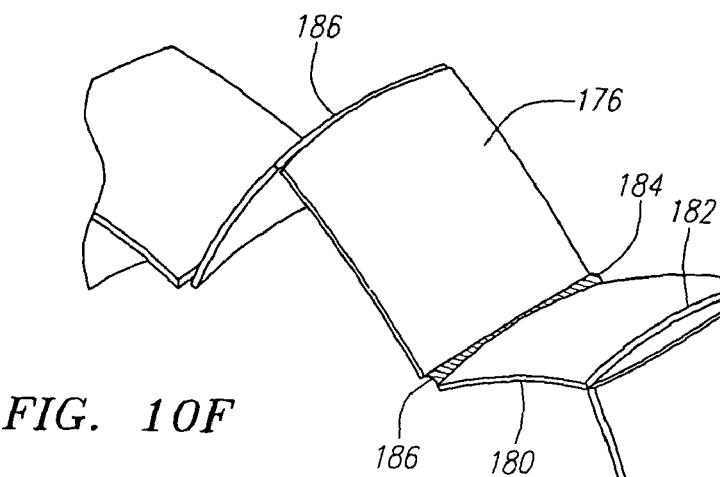
FIG. 10F is a perspective view of a portion of a ring of panels contained on the support member shown in FIG. 10C.
Figure 10G:
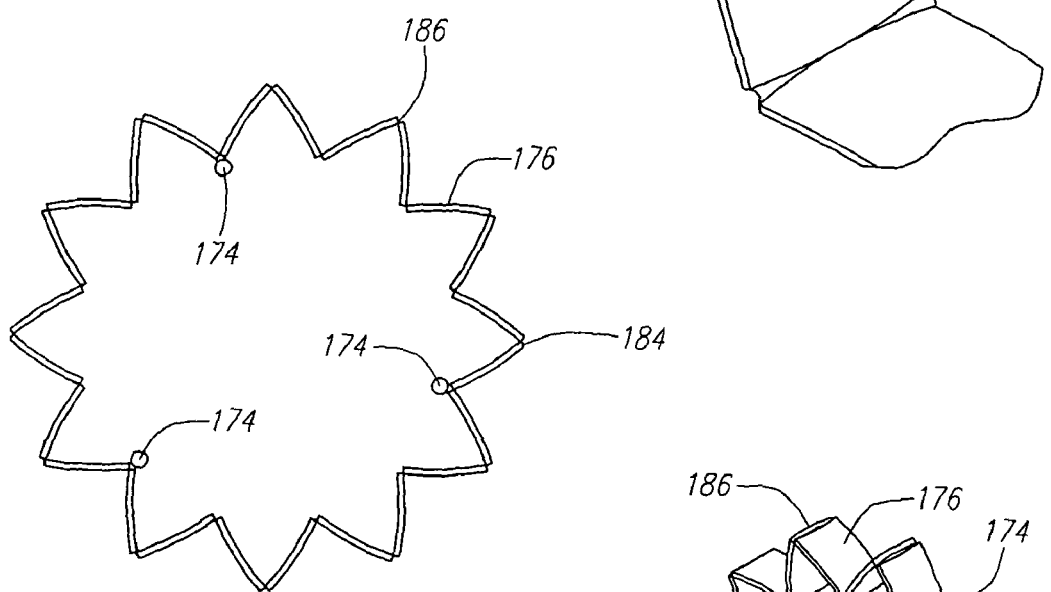
FIG. 10G is a top view of a ring of panels contained on a support member, shown in a contracted state.
Figure 10H:
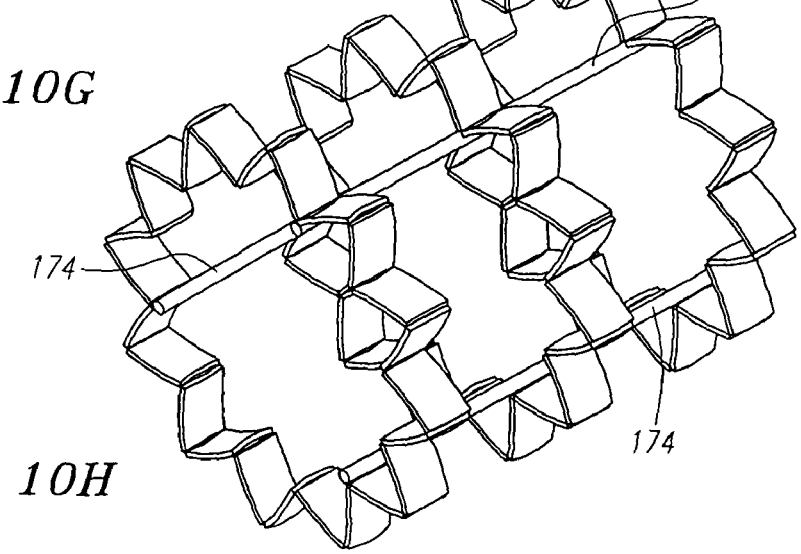
FIG. 10H is a perspective view of the support member shown in FIG. 10C, shown in the contracted state.
Figure 10I:
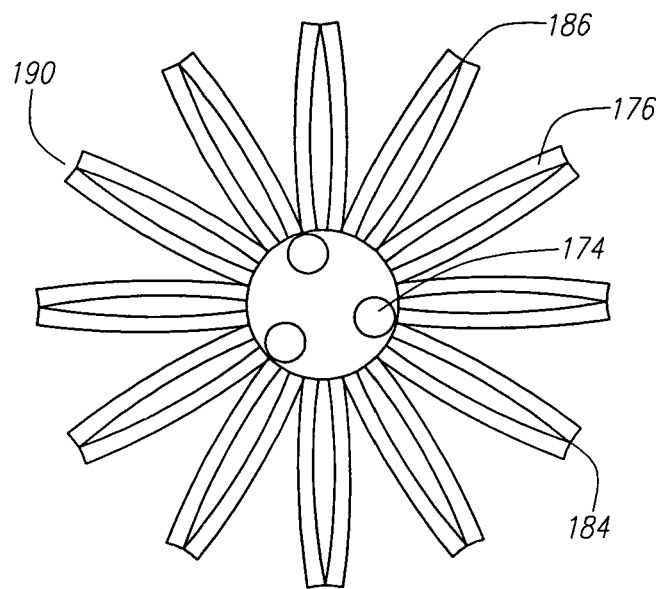
FIG. 10I is a top view of a ring of panels contained on another support member, shown in a contracted state.
Figure 10J:
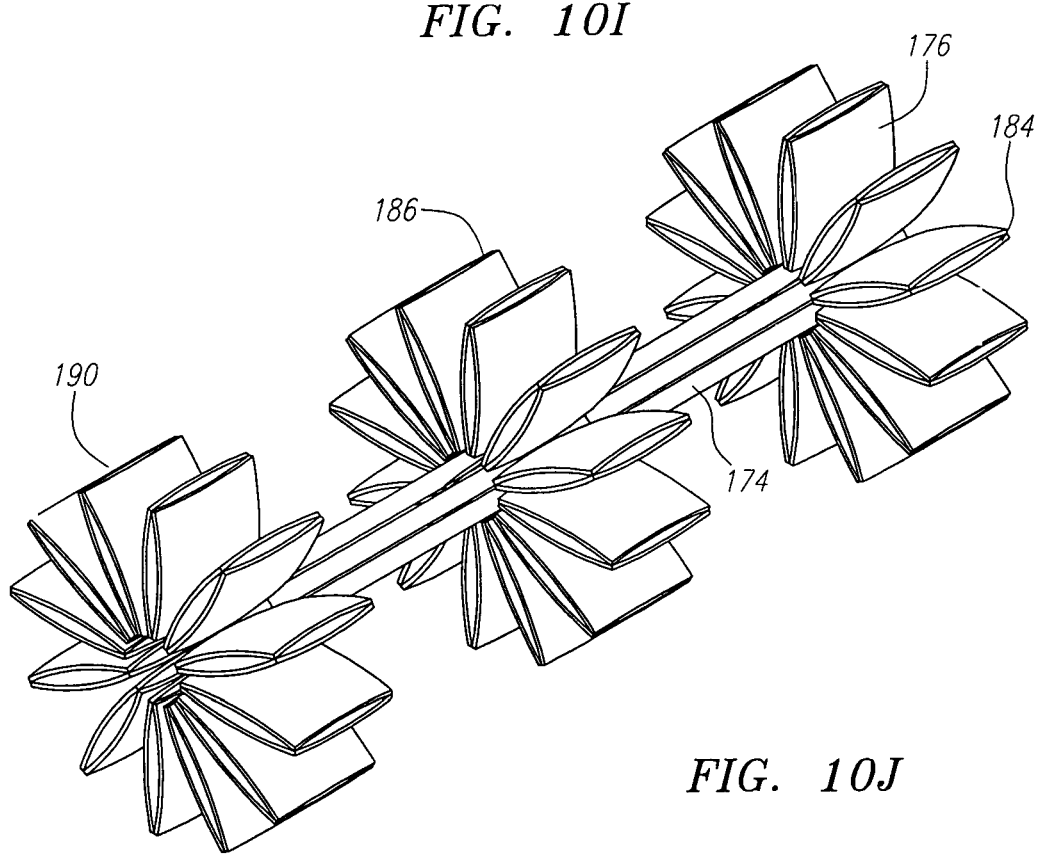
FIG. 10J is a perspective view of the support member shown in FIG. 10I, shown in the contracted state.

Another support member is shown in FIGS. 10A-J. In this alternative embodiment, the support member comprises a multiple panel hinged ring structure 170. The multiple panel hinged ring structure includes three circumferential rings 172 interconnected by three longitudinal posts 174. More or fewer rings and/or posts may be used. Each ring structure, in turn, is composed of a plurality of curved panels 176, each connected to its adjacent panel by a junction member 178, such as a polymeric membrane hinge. The individual panels 176 have a curvature 180 about the axis of the device as well as a curvature 182 in the transverse direction. (See FIG. 10E). A coating material 184 maintains the panels in relation to one another, as well as providing a foldable junction 186. The curvature of the panels in conjunction with the coating 184 maintains the ring structure in the expanded condition, as shown in FIGS. 10A, 10C, and 10D. The foldable junctions 186 are rotated to transform the structure from an expanded state 188 for deployment, to a contracted state 190 for delivery. (See FIG. 10F-J). A valvular body, as described elsewhere herein, may be attached to the internal or external surface of the support member.

Figure 11A:
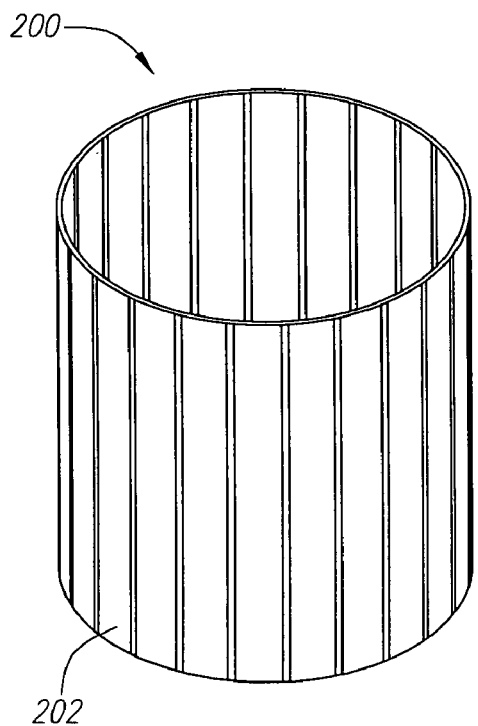
FIG. 11A is a perspective view of a collapsing hinged support member, shown in its expanded state.
Figure 11B:
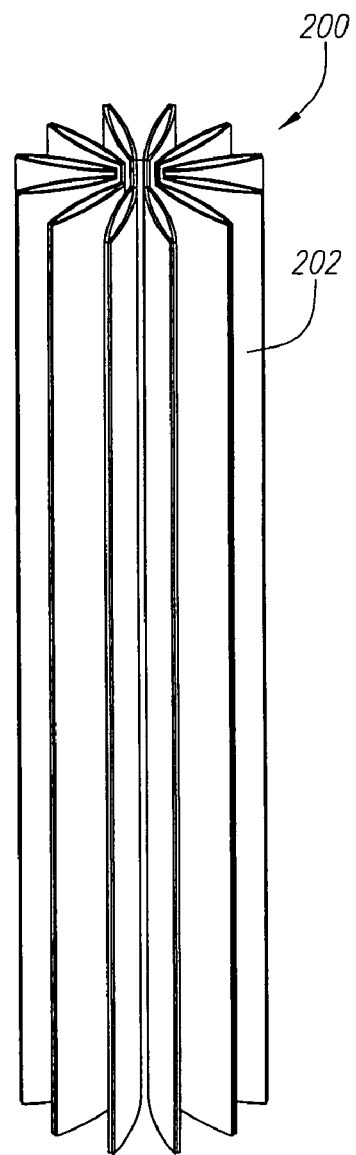
FIG. 11B is a perspective view of the collapsing hinged support member, shown in its contracted state.
Figure 11C:
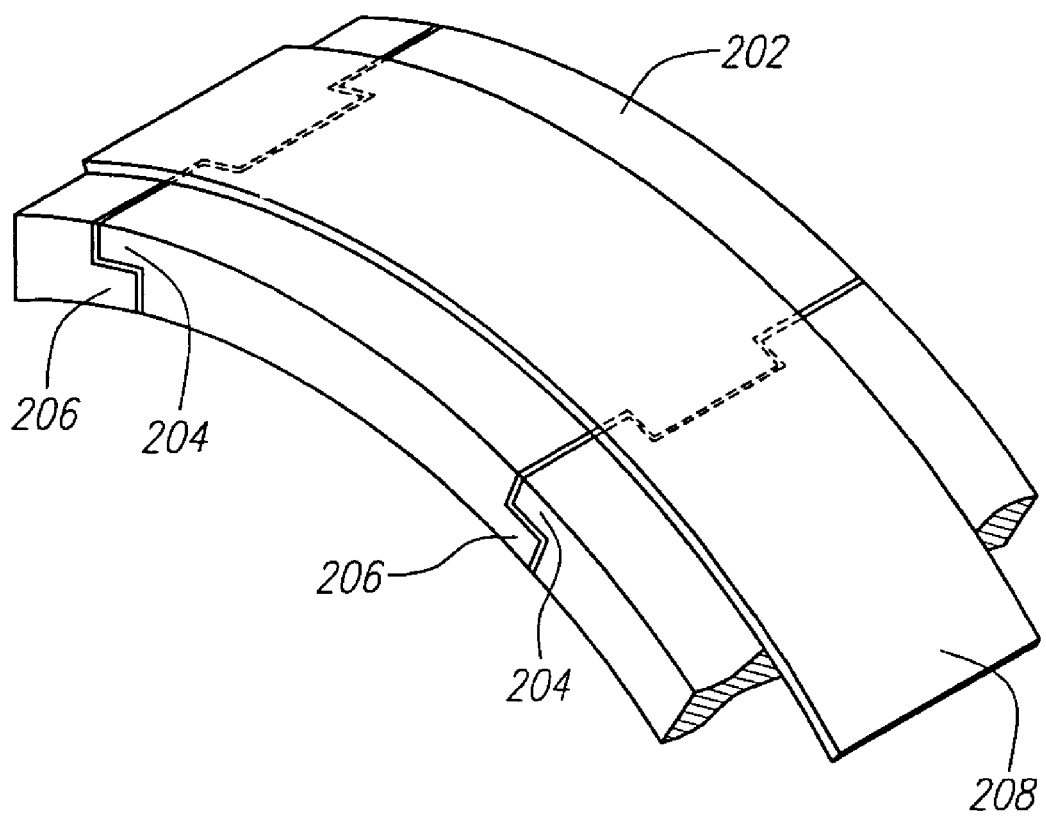
FIG. 11C is a close-up view of a portion of the collapsing hinged support member shown in FIG. 11A.
Figure 12A:
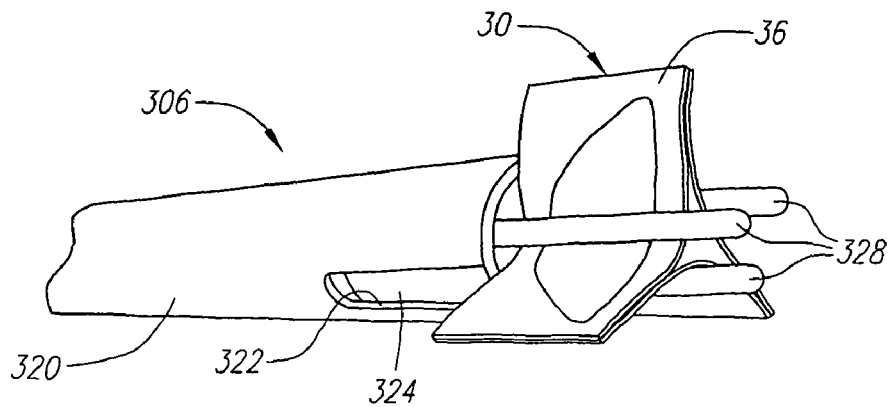
FIG. 12A is a perspective view of a prosthetic valve retained on a delivery device.
Figure 12B:
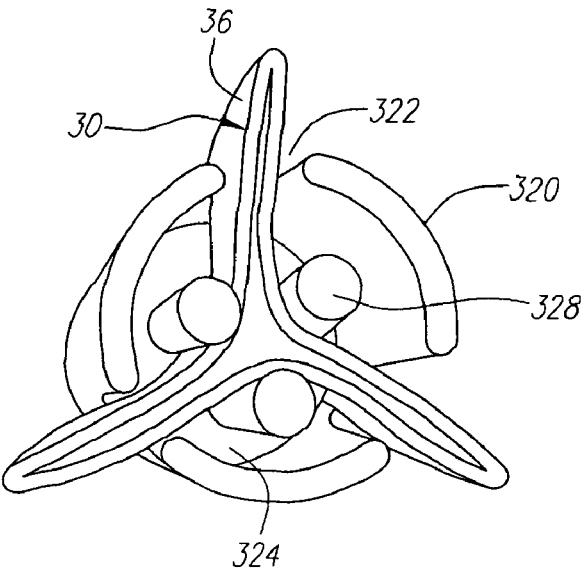
FIG. 12B is a top view of the prosthetic valve and delivery device shown in FIG. 12A.
Figure 12C:
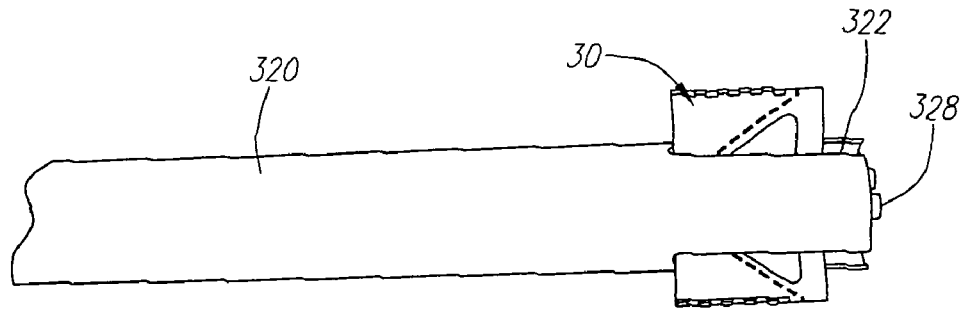
FIG. 12C is a side view of the prosthetic valve and delivery device shown in FIG. 12A.
Figure 12D:
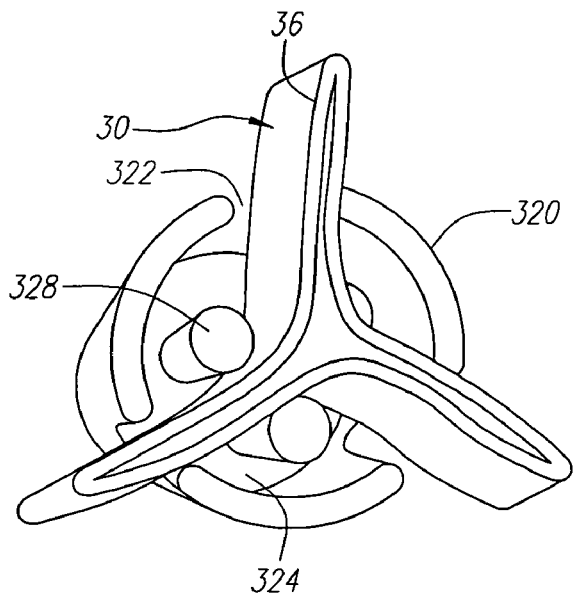
FIG. 12D is another top view of the prosthetic valve and delivery device shown in FIG. 12A.
Figure 12E:
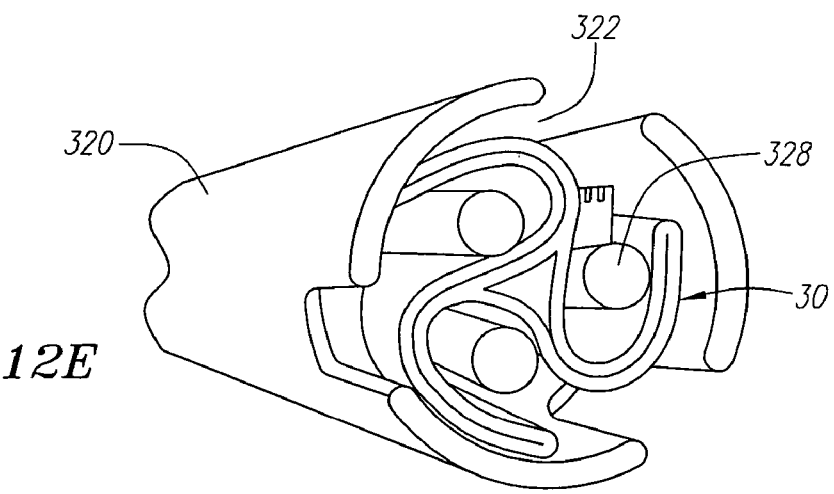
FIG. 12E is another top view the prosthetic valve and delivery device shown in FIG. 12A.
Figure 12F:
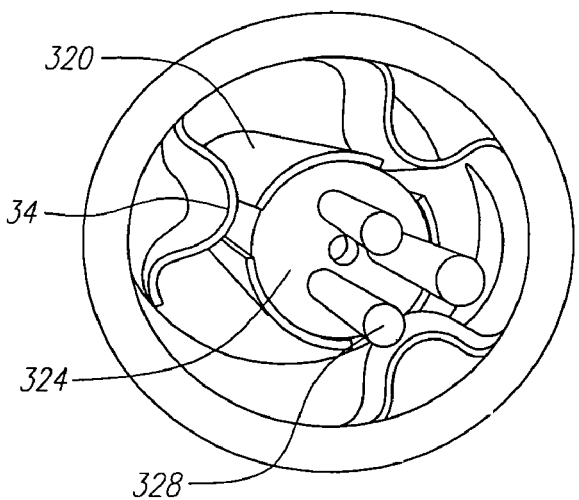
FIG. 12F is another top view of the prosthetic valve and delivery device shown in FIG. 12A.

In still another alternative embodiment, as shown in FIGS. 11A-C, the support member comprises a collapsing hinged structure 200. The collapsing hinged structure shown in the Figures includes twenty-four panels 202 arranged peripherally around the generally tubular structure, each panel having a tab 204 on its edge that overlaps and engages a mating tab 206 on the opposed edge of the adjacent panel, interlocking the adjacent panels. More or fewer panels are possible. An elastic membrane 208 is attached to an external surface of adjacent panels and provides a force biasing the adjacent panels together to assist the tabs in interlocking each adjacent pair of panels. Preferably, the elastic membrane 208 is attached to the main body of each panel 202, but not at the opposed edges. Thus, the tabs 204, 206 may be disengaged and the panels 202 rotated to form a vertex 210 at each shared edge, thereby defining a multi-vertex "star" shape that corresponds with the contracted state of the support member. The support member 200 is transformed to its expanded state by applying an outward radial force that stretches the elastic membrane 208 and allows the tabs 204, 206 to re-engage. A valvular body, as described elsewhere herein, is attached to the internal or external surface of the support member.

All of the foregoing support members may be incorporated in a prosthetic valve, as described above, by attaching a valvular body to the external or internal surface of the support member. In the alternative, all of the foregoing support members may be utilized without a valvular body to provide a support or scaffolding function within a body lumen, such as a blood vessel or other organ. For example, the multi-segment, multi-hinged support member may be used as a scaffolding member for the treatment of abdominal aortic aneurisms, either alone, or in combination with another support member, graft, or other therapeutic device. Other similar uses are also contemplated, as will be understood by those skilled in the art.

Figure 13A:
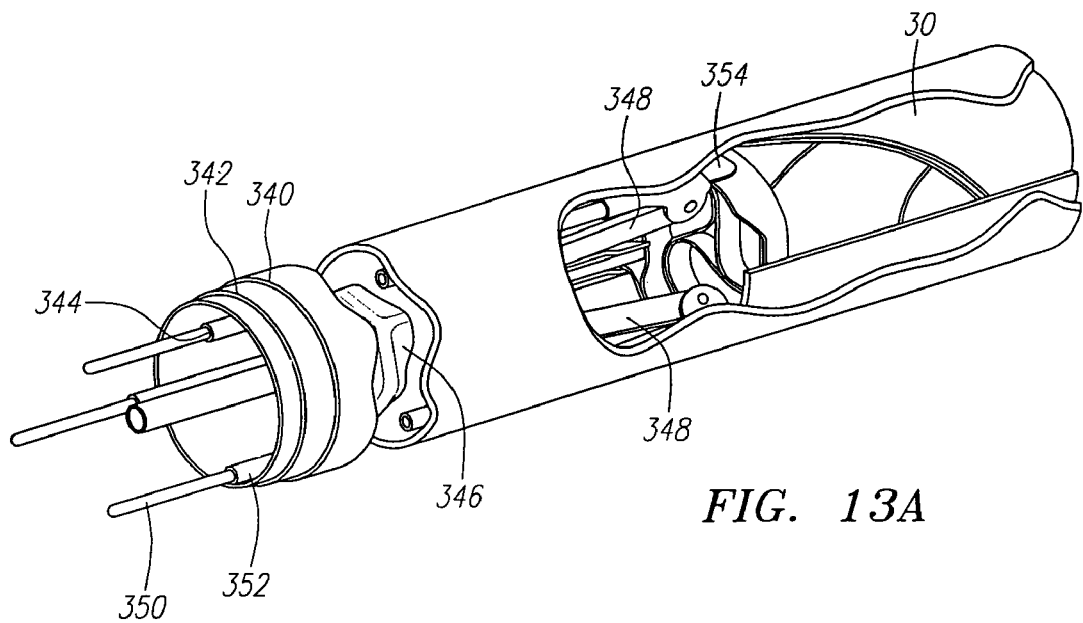
FIG. 13A is a perspective view, shown in partial cross-section, of a prosthetic valve delivery device.
Figure 13B:
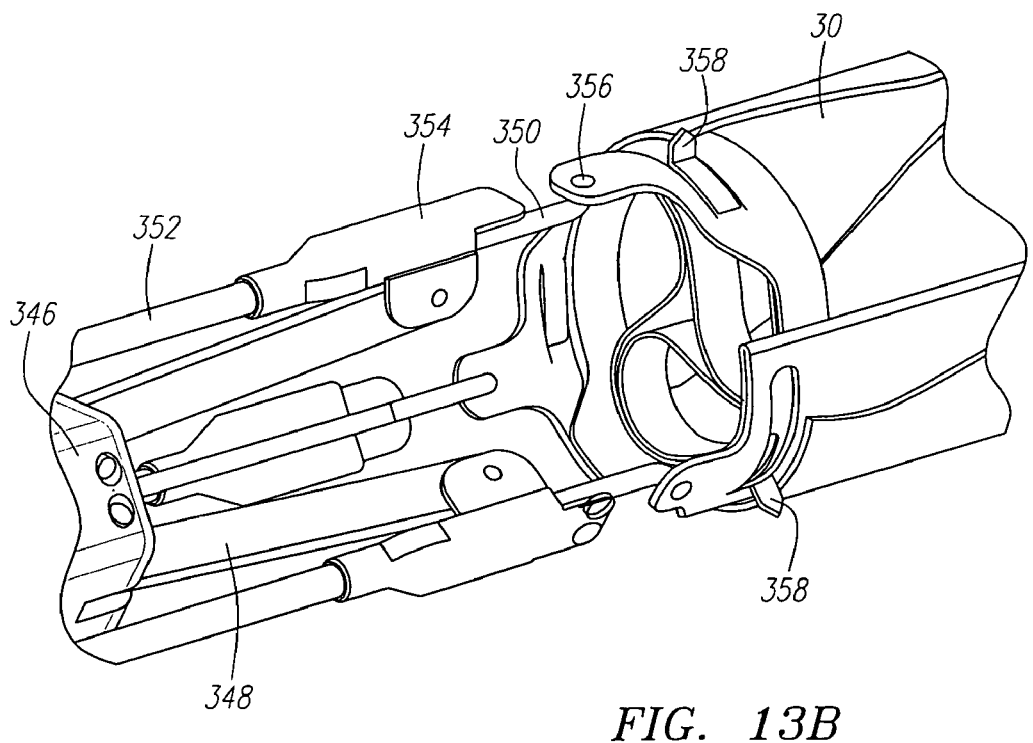
FIG. 13B is a close-up view of a portion of the prosthetic valve delivery device shown in FIG. 13A.
Figure 13C:
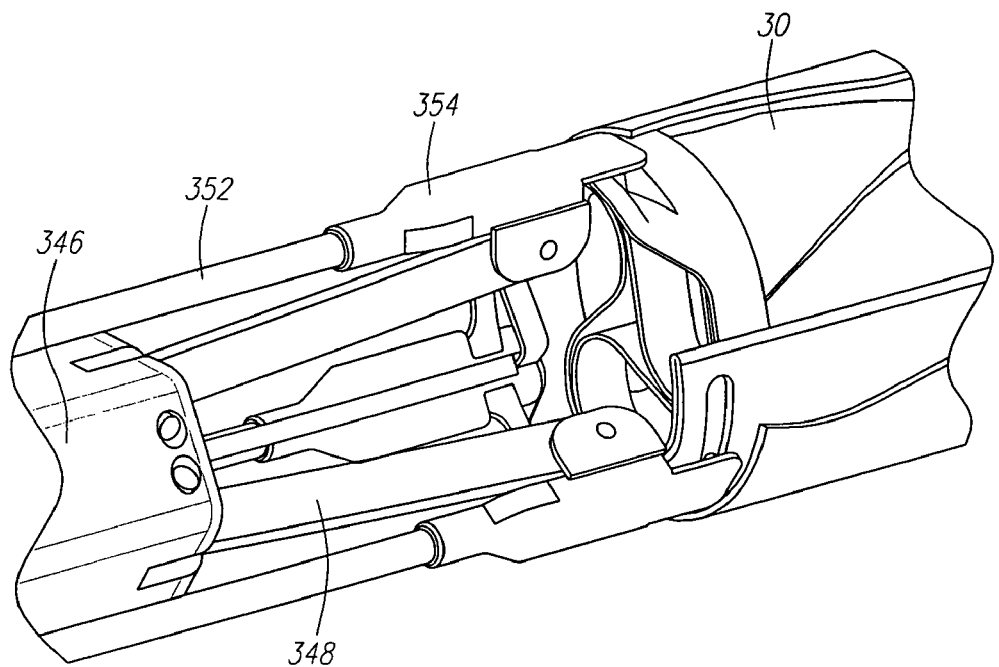
FIG. 13C is another close-up view of a portion of the prosthetic valve delivery device shown in FIG. 13A
Figure 13D:
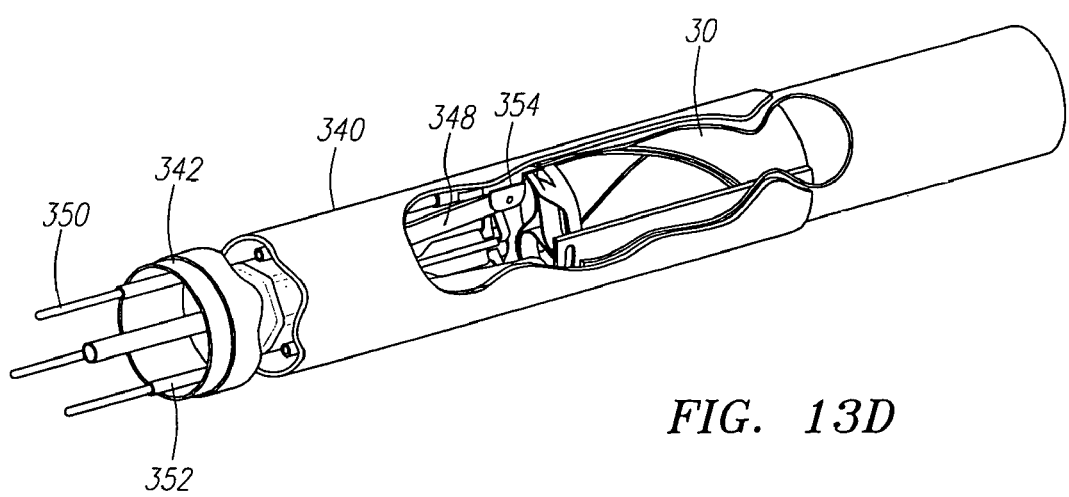
FIG. 13D is another perspective view, shown in partial cross-section, of the prosthetic valve delivery device shown in FIG. 13A.
Figure 13E:
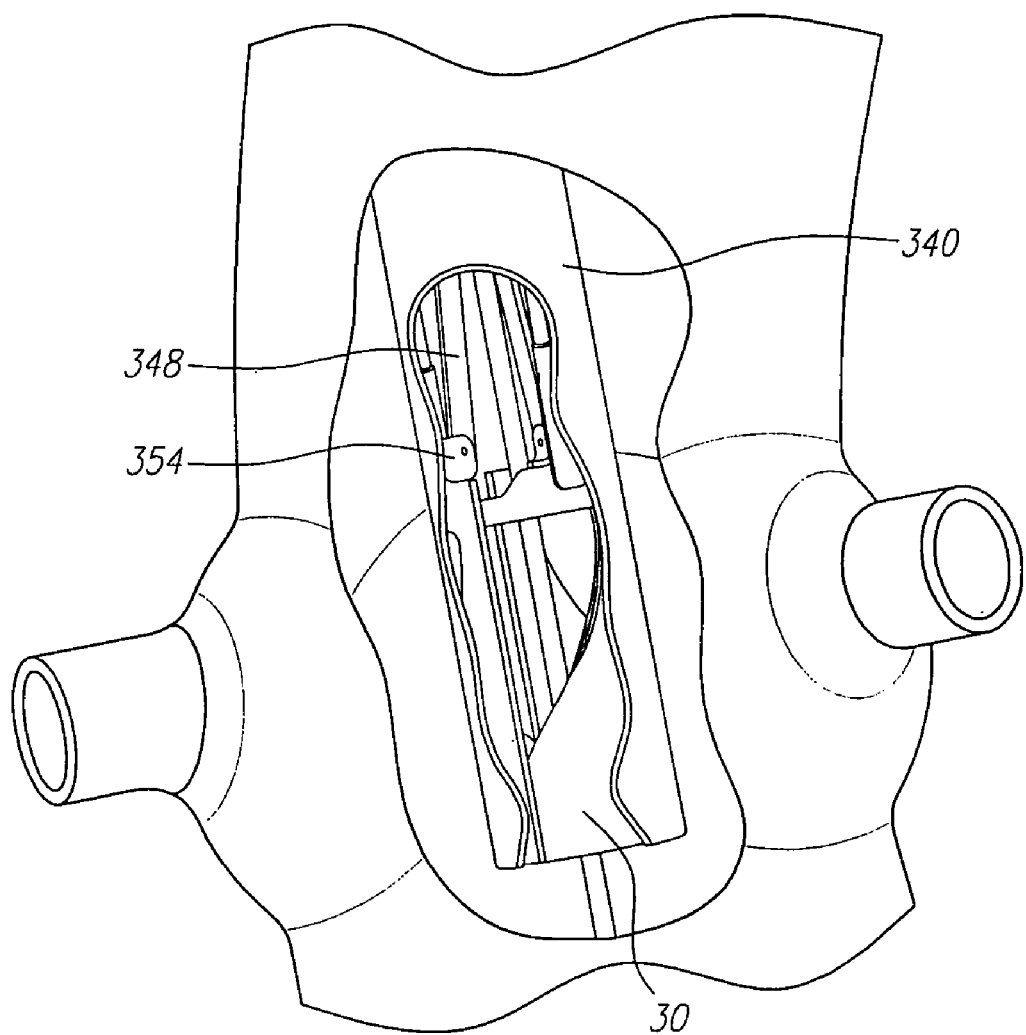
FIG. 13E is an illustration showing the delivery device of FIG. 13A delivering a prosthetic valve to a treatment location.

Moreover, several additional features and functions may be incorporated on or in the prosthetic valve or its components, including the support member and the valvular body. For example, one or more anchoring members may be formed on or attached to any of the above-described support member embodiments. Each anchoring member may comprise a barb, a tooth, a hook, or any other member that protrudes from the external surface of the support structure to physically engage the internal wall of the body lumen. An anchoring member may be selectively engageable, such as by an actuator, or it may be oriented so as to be permanently in its engaged state. Alternatively, the anchoring member may comprise an aperture formed in the support structure that allows tissue to invaginate therethrough. One example of an anchoring member is illustrated in FIGS. 13B and 13C, where a barb 358 is shown extending from the surface of a contracted prosthetic valve 30. The barb 358 may be deflected inward while the prosthetic valve is retained in the delivery device. See FIG. 13C. Then, upon deployment, the barb 358 is released and extends radially outward to engage the surface of the body lumen or other tissue. As noted above, other anchoring members and mechanisms are also contemplated for use with the devices described herein.

The prosthetic heart valves and support members described herein provide a number of advantages over prior devices in the art. For example, the prosthetic heart valves are able to be transformed to a contracted state and back to an expanded state without causing folding, tearing, crimping, or otherwise deforming the valve leaflets. In addition, unlike prior devices, the expanded state of the current device has a fixed cross-sectional size (e.g., diameter) that is not subject to recoil after expansion. This allows the structure to fit better at its treatment location and to better prevent migration. It also allows the valvular body to perform optimally because the size, shape and orientation of the valve leaflets may be designed to a known deployment size, rather than a range. Still further, because the expanded state of the support structure is of a known shape (again, unlike the prior devices), the valve leaflets may be designed in a manner to provide optimal performance.

B. Delivery Devices and Methods of Use

Figure 14A:
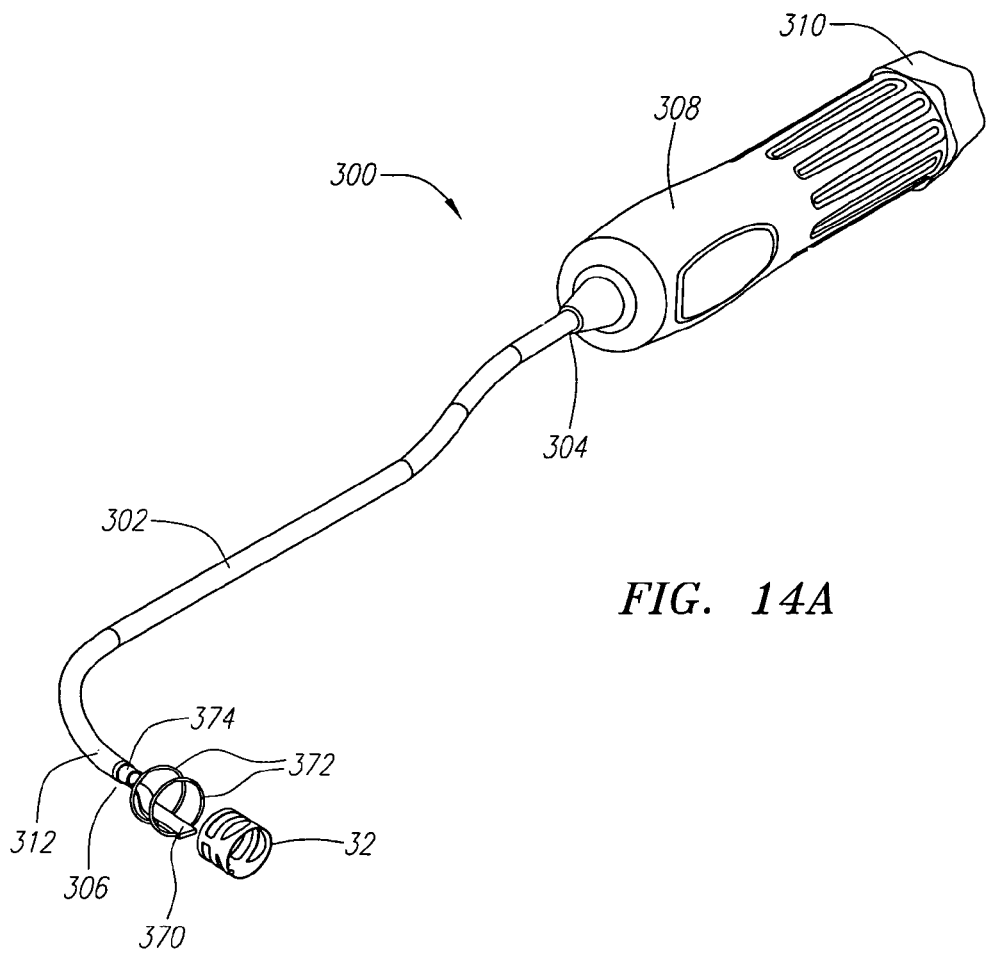
FIG. 14A is a perspective view of another prosthetic valve delivery device.
Figure 14B:
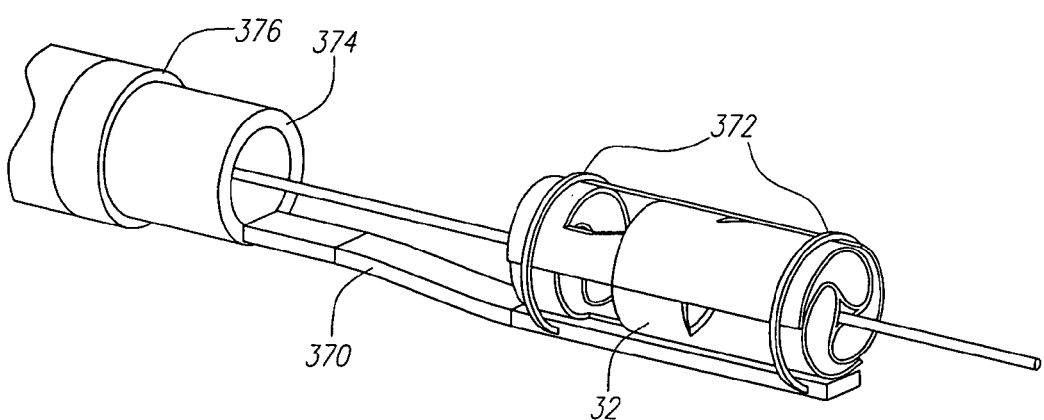
FIG. 14B is a close-up view of a distal portion of the prosthetic valve delivery device shown in FIG. 14A.
Figure 14C:
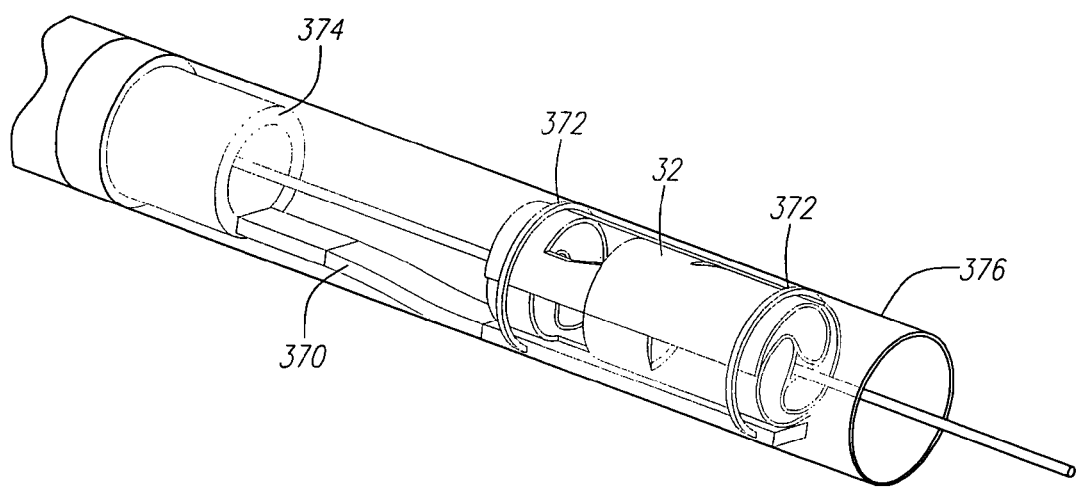
FIG. 14C is another close-up view of the distal portion of the prosthetic valve delivery device shown in FIG. 14A.
Figure 14D:
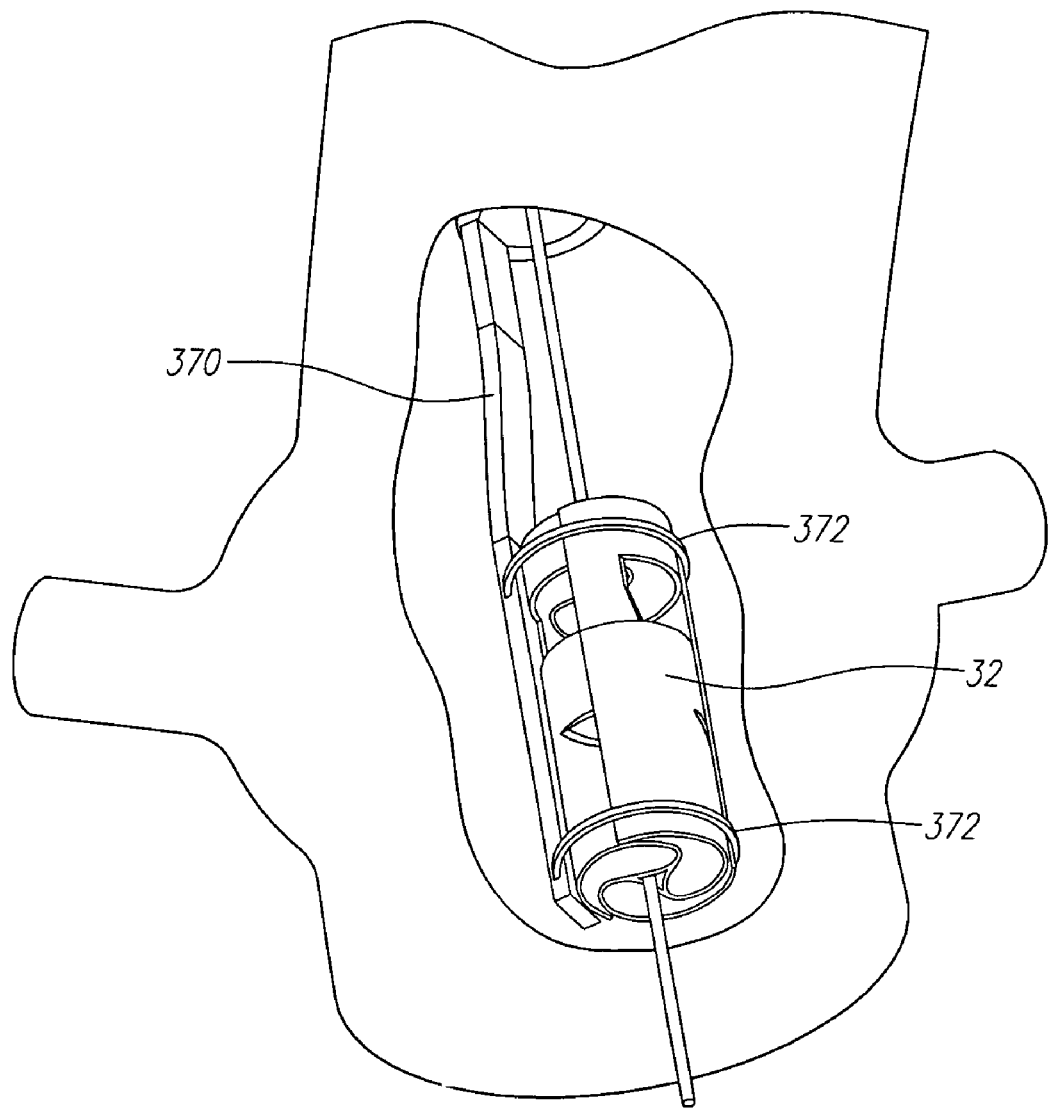
FIG. 14D is an illustration showing the delivery device of FIG. 14A delivering a prosthetic valve to a treatment location.
Figure 14E:
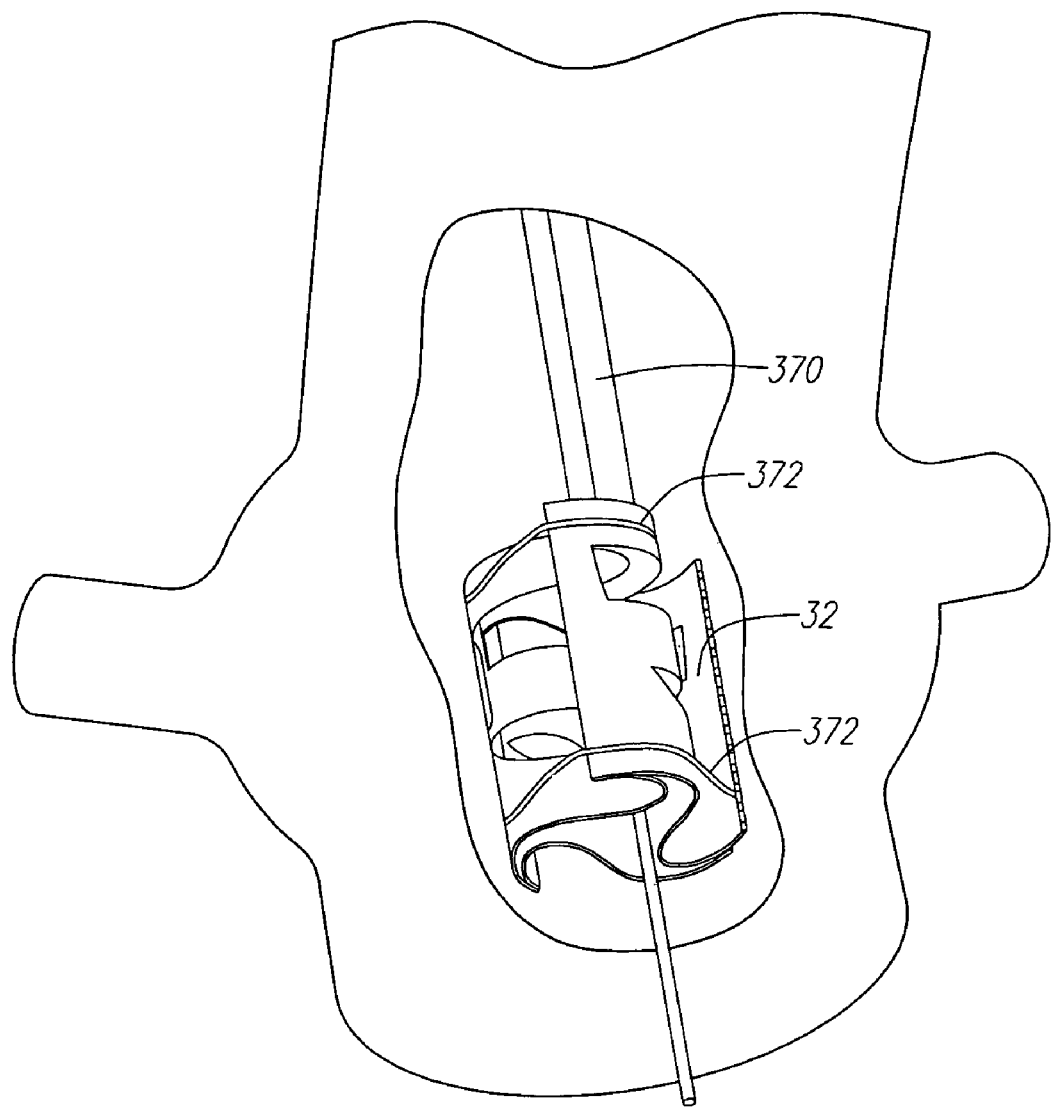
FIG. 14E is another illustration showing the delivery device of FIG. 14A delivering a prosthetic valve to a treatment location.
Figure 15A:
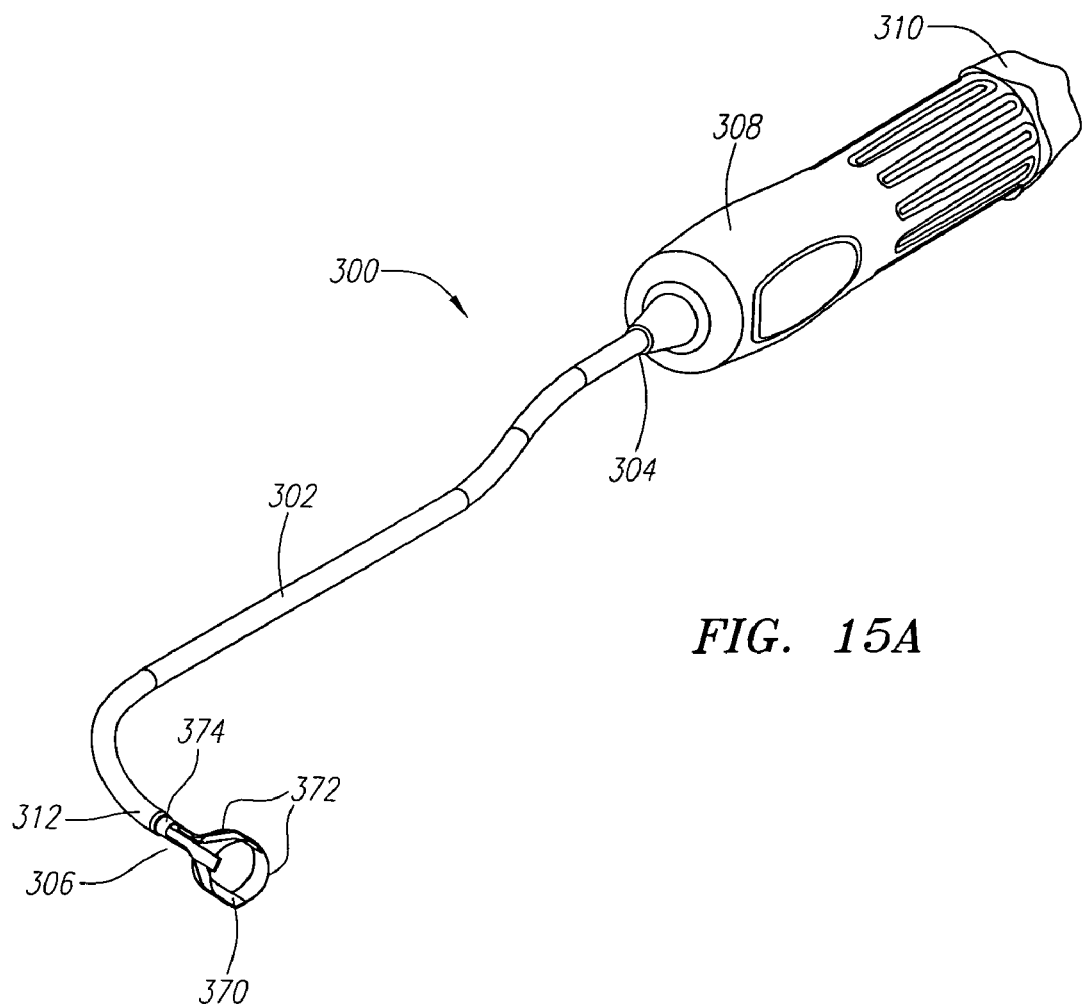
FIG. 15A is a perspective view of another prosthetic valve delivery device.
Figure 15B:
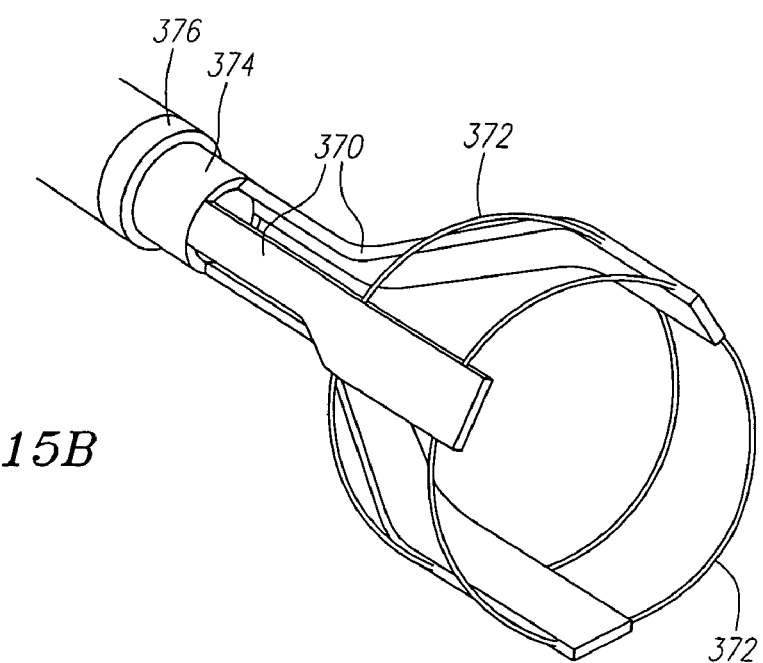
FIG. 15B is a close-up view of a distal portion of the prosthetic valve delivery device shown in FIG. 15A.

Devices for delivering a prosthetic valve to a treatment location in a body lumen are described below, as are methods for their use. The delivery devices are particularly adapted for use in minimally invasive interventional procedures, such as percutaneous aortic valve replacements. FIGS. 14A and 15A illustrate two embodiments of the devices. The delivery devices 300 include an elongated delivery catheter 302 having proximal 304 and distal ends 306. A handle 308 is provided at the proximal end of the delivery catheter. The handle 308 may be provided with a knob 310, an actuator, a slider, other control members, or combinations thereof for controlling and manipulating the catheter to perform the prosthetic valve delivery procedure. A retractable outer sheath 312 may extend over at least a portion of the length of the catheter. Preferably, a guidewire lumen extends proximally from the distal end of the catheter. The guidewire lumen may extend through the entire length of the catheter for over-the-wire applications, or the guidewire lumen may have a proximal exit port closer to the distal end of the catheter than the proximal end for use with rapid-exchange applications. The distal portion 306 of the catheter includes a carrier adapted to receive and retain a prosthetic valve in a contracted state, and to deploy the prosthetic valve at a treatment location within a body lumen.

Turning first to FIGS. 12A-F, a first embodiment of a distal portion 306 of a prosthetic valve delivery device is shown. The device 300 includes a delivery tube 320 having three longitudinal slots 322 at its distal end, and a gripper 324 having a longitudinal shaft 326 and three fingers 328 that extend longitudinally from the distal end of the gripper. More or fewer longitudinal slots may be included on the delivery tube, and more or fewer fingers may be provided on the gripper. Preferably, the delivery tube 320 has the same number of longitudinal slots, and the gripper 324 includes the same number of fingers, as there are segments on the prosthetic valve to be delivered. The longitudinal slots 322 on the distal end of the delivery tube are equally spaced around the periphery of the tube. Similarly, as viewed from the distal end of the gripper 324, the fingers 328 are arranged in an equispaced circular pattern. For example, in the case of three fingers, all three are equally spaced apart on an imaginary circle and are separated from each other by 120°. In the case of four fingers, the fingers would be separated from each other by 90°, and so on.

The gripper 324 is slidably and rotatably received within the delivery tube 320, and the delivery tube is internal of the outer sheath (not shown in FIGS. 12A-F). The outer sheath is retractable to expose at least the longitudinal slots 322 on the distal portion of the delivery tube. The gripper 324 is able to be advanced at least far enough to extend the fingers 328 distally outside the distal end of the delivery tube.

In alternative embodiments of the above delivery device, the gripper fingers 328 may comprise wires, fibers, hooks, or other structural members extending distally from the distal end of the gripper. As described below, a primary function of the fingers is to retain a prosthetic valve on the distal end of the gripper, and to restrain segments of the support member of the valve in an inverted state. Accordingly, any of the above (or other) structural members able to perform the above function may be substituted for the fingers described above.

The delivery device 300 is particularly adapted for use in a minimally invasive surgical procedure to deliver a multi-segment prosthetic valve 30, such as those described above, to a body lumen. To do so, the prosthetic valve 30 is first loaded into the delivery device 300. FIGS. 12A-F illustrate the case of a prosthetic valve having a three segment support member. The prosthetic valve 30 is loaded into the delivery device 300 by first inverting the three panels 36 to produce a three vertex structure. Inverting of the prosthetic valve panels may be performed manually, or by using an inverting tool. The prosthetic valve 30 is then placed onto the distal end of the gripper 324, which has been previously extended outside the distal end of the delivery tube 320, with each of the three fingers 328 retaining one of the inverted panels 36 in its inverted position. (See FIG. 12A). The gripper 324 and fingers 328, with the prosthetic valve 30 installed thereon, are then retracted back into the delivery tube 320. During the retraction the gripper 324 and fingers 328 are rotationally aligned with the delivery tube 320 such that the three vertices of the prosthetic valve align with the three longitudinal slots on the distal end of the delivery tube. (See FIG. 12B). When the gripper 324 and fingers 328 are fully retracted, each of the three vertices of the prosthetic valve extends radially outside the delivery tube through the longitudinal slots 322. (See FIG. 12C). The gripper 324 is then rotated relative to the delivery tube 320, which action causes each of the folded segments of the prosthetic valve 30 to engage an edge of its respective delivery tube slot. (See FIG. 12D). Further rotation of the gripper 324 relative to the delivery tube 320 causes the folded segments to curl back toward the longitudinal axis of the prosthetic valve internally of the delivery tube, creating three lobes located fully within the delivery tube 320. (See FIG. 12E). The prosthetic valve 30 is thereby loaded into the delivery device 300. The outer sheath is then advanced over the distal portion of the catheter, including the delivery tube, to prepare the delivery device for use.

The prosthetic valve 30 is delivered by first introducing a guidewire into the vascular system and to the treatment location of the patient by any conventional method, preferably by way of the femoral artery. Optionally, a suitable introducer sheath may be advanced to facilitate introduction of the delivery device. The delivery catheter 302 is then advanced over the guidewire to the treatment location. The outer sheath 312 is then retracted to expose the delivery tube 320. The gripper 324 is then rotated relative to the delivery tube 320 (or the delivery tube rotated relative to the gripper), thereby causing the folded panels of the prosthetic valve 30 to uncurl and to extend radially outward through the longitudinal slots 322 of the delivery tube 320. The delivery tube 320 is then retracted (or the gripper advanced) to cause the prosthetic valve 30 (restrained by the fingers 328) to advance distally out of the delivery tube. The gripper 324 is then retracted relative to the prosthetic valve 30, releasing the prosthetic valve 30 into the treatment location. (See FIG. 12F). Preferably, the inverted panels 36 then revert to the expanded state, causing the valve to lodge against the internal surface of the body lumen (e.g., the aortic valve root or another biologically acceptable aortic position). Additional expansion of the prosthetic valve may be provided, if needed, by a suitable expansion member, such as the expansion balloon or the expanding mesh member described elsewhere herein, carried on the delivery catheter 302 or other carrier.

Turning to FIGS. 13A-E, another embodiment of a distal portion of a prosthetic valve delivery device is shown. The distal portion of the catheter 302 includes a restraining sheath 340, an orientation sheath 342, a plurality of grippers 344, an expander 346, and a plurality of struts 348. Each of the grippers 344 includes a wire 350 riding within a tube 352, and a tip 354 at the distal end of the tube. The wire 350 of each gripper 344 has an end portion 356 formed to engage the vertex of a prosthetic valve support member 32 having multiple segments, and to selectively restrain the prosthetic valve 30 in a contracted state. (See FIG. 13B). The expander 346 is adapted to selectively cause the grippers 344 to expand radially outwardly when it is actuated by the user by way of an actuator 310 located on the handle 308.

The prosthetic valve 30 may be loaded into the delivery device 300 by contracting the prosthetic valve (either manually or with an inverting tool) by inverting each panel 36 and then attaching each vertex to a respective end portion 356 of the wire contained on each gripper 344 on the delivery device. The gripper wires 350 receive, retain, and restrain the prosthetic valve 30 in its contracted state. The gripper 344 assembly having the prosthetic valve 30 installed is then retracted into each of the orientation sheath 342 and the restraining sheath 340 to prepare the device for insertion into the patient's vasculature. The device is then advanced over a guidewire to a treatment location, such as the base annulus of the native aortic valve. (See FIG. 13E). The restraining sheath 340 is then retracted to allow the prosthetic valve 30 to partially expand (e.g., to about 85% of its full transverse dimension), where it is constrained by the orientation sheath 342. The prosthetic valve 30 is then finally positioned by manipulation of the grippers 344, after which the orientation sheath 342 is retracted and the grippers 344 released. The prosthetic valve 30 then lodges itself in the treatment location.

Other embodiments of the delivery device are illustrated in FIGS. 14A-E and 15A-B. As shown in those Figures, the distal portion 306 of the catheter includes one or more restraining tubes 370 having at least one (and preferably two) adjustable restraining loops 372. In the embodiment shown in FIGS. 14A-E, the device is provided with one restraining tube 370 and two restraining loops 372. In the embodiment shown in FIGS. 15A-B, the device is provided with three restraining tubes 370 and two restraining loops 372. The restraining tube(s) 370 extend distally from a catheter shaft 374 out of the distal end of the delivery device, and each restraining loop 372 is a wire or fiber loop that extends transversely of the restraining tube 370. Each restraining loop 372 is a flexible loop capable of selectively restraining a contracted prosthetic valve. The restraining loops 372 may be selectively constricted or released by a control member, such as a knob 310, located on the handle 308 of the device. A retractable outer sheath 376 covers the distal portion of the catheter.

The prosthetic valve 30 may be loaded onto the delivery device by contracting the prosthetic valve (either manually or with an inverting tool) into its contracted state, for example, by inverting each panel 36 and curling each inverted panel into a lobe. The contracted prosthetic valve is then placed onto the restraining tube(s) 370 and through the one or more restraining loops 372. (See, e.g., FIG. 14B). The loops 372 are constricted around the contracted prosthetic valve 30, thereby restraining the prosthetic valve in its contracted state. The outer sheath 376 is then advanced over the prosthetic valve and the restraining tube(s) to prepare the delivery device for use. (See FIG. 14C). The device is then advanced over a guidewire to a treatment location, such as the base annulus of the native aortic valve. (See FIG. 14D). The restraining sheath 376 is then retracted to expose the contracted prosthetic valve 30. The restraining loops 372 are released, such as by rotating the control knob 310, thereby releasing the prosthetic valve 30 and allowing it to self-expand. (See FIG. 14E). The prosthetic valve 30 then lodges itself in the treatment location. An expansion member may be advanced to the interior of the prosthetic valve and expanded to provide additional expansion force, if needed or desired.

Figure 16A:
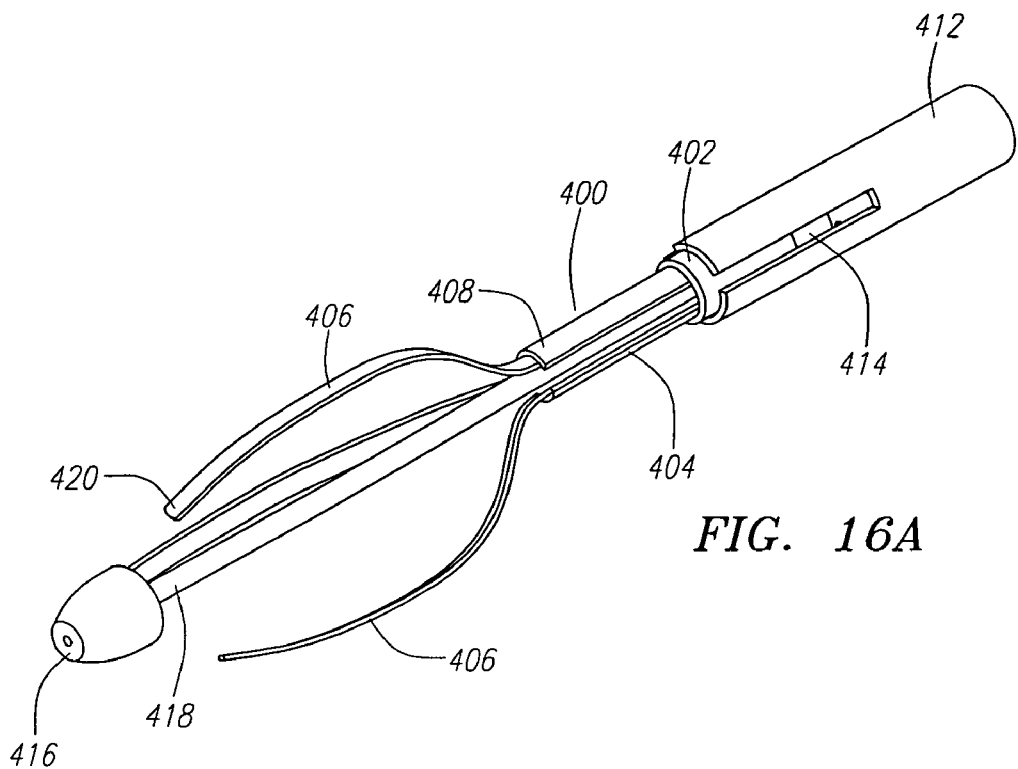
FIG. 16A is a perspective view of another prosthetic valve delivery device.
Figure 16B:
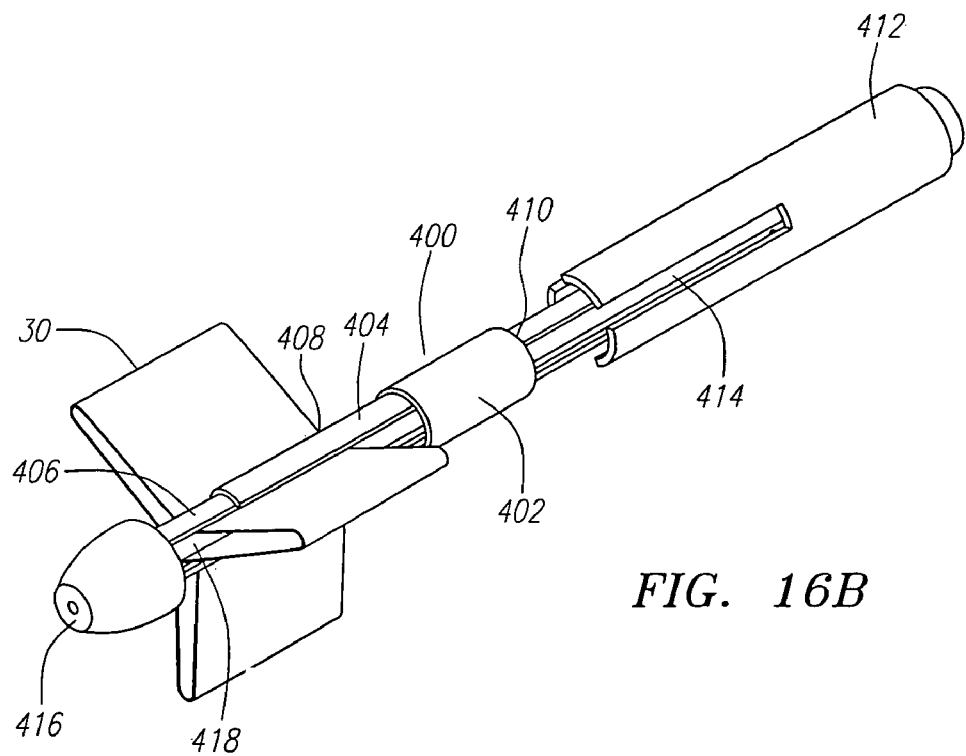
FIG. 16B is another perspective view of the prosthetic valve delivery device shown in FIG. 16A.

Another embodiment of the delivery device is shown in FIGS. 16A-B. As shown there, the distal portion of the catheter includes a gripper 400 that includes a base portion 402 having three restraining members 404 extending distally from the gripper base. In the embodiment shown, each of the restraining members 404 includes a wire loop 406 extending through a sleeve 408, with both the sleeve and the wire loop extending distally from the gripper base 402. The wire loops 406 also extend proximally of the gripper base 402, which is provided with a lumen 410 corresponding with each of the wire loops 406, thereby allowing the gripper base 402 and the sleeves 404 to slide relative to the wire loops 406. A delivery tube 412 may also be provided. As shown in the Figures, the gripper 400 is slidably received within the delivery tube 412, and the tube has three longitudinal slots 414 corresponding with the three restraining members 404 on the gripper assembly. An atraumatic tip 416 or nosecone is attached to a central shaft 418 that extends through the center of the catheter 302 internally of the gripper 400 and the delivery tube 412. The central shaft 418 includes a guidewire lumen to accommodate a guidewire used to assist deployment of the delivery device.

Although the device shown in the Figures includes three restraining members 404, fewer or additional restraining members may be used. One function of the restraining members is to retain a prosthetic valve on the distal end of the delivery device, and to selectively maintain the valve in a contracted state. In the preferred embodiment, the number of restraining members will coincide with the number of segments (e.g., panels) included on the prosthetic valve.

Turning to FIG. 16A, the delivery device 300 is shown with the delivery tube 412 and gripper 400 retracted relative to the wire loops 406, thereby allowing the distal ends 420 of the wire loops to extend freely away from the central shaft 418. The delivery device in this condition is adapted to have a prosthetic valve installed onto the device. To do so, the prosthetic valve 30 is first placed over the distal end of the device and the panels 36 of the valve are inverted. Alternatively, the valve panels 36 may be inverted prior to or simultaneously with placing the valve over the distal end of the delivery device. The wire loops 406 are then placed over the inverted panels 36, and the gripper 400 is advanced to cause the sleeves 408 to physically engage the inverted panels 36. See FIG. 16B. The sleeves 408 have sufficient strength to maintain the prosthetic valve panels in their inverted state. The delivery tube 412 may then be advanced over the distal end of the device, with the valve panel vertices extending out of the longitudinal slots 414 formed on the delivery tube 412. The gripper 400 may then be rotated relative to the delivery tube (or vice versa) to contract the panel vertices within the interior of the delivery tube and to thereby prepare the device for delivery of the prosthetic valve. The valve is delivered in the same manner described above in relation to the device shown in FIGS. 12A-E.

As noted, each of the foregoing delivery devices is suitable for use in delivering a prosthetic heart valve or a support member, such as those described herein. In the case of a prosthetic heart valve, the delivery methods may be combined with other treatment devices, methods, and procedures, particularly procedures intended to open or treat a stenotic heart valve. For example, a valvuloplasty procedure may be performed prior to the prosthetic heart valve deployment. The valvuloplasty procedure may be performed using a conventional balloon or a cutting balloon adapted to cut scarred leaflets so that they open more easily. Other treatments, such as chemical treatments to soften calcifications or other disorders may also be performed.

Each of the foregoing delivery devices may be provided with a tether connecting the delivery device to the prosthetic valve or support member. The tether is preferably formed of a material and has a size sufficient to control the prosthetic valve or support member in the event that it is needed to withdraw the device during or after deployment. Preferably, the tether may be selectably disengaged by the user after deployment of the device.

Turning to FIGS. 17A-B and 18A-D, two types of expansion members are provided for performing dilation functions in minimally invasive surgical procedures. The expansion members may be used, for example, in procedures such as angioplasty, valvuloplasty, stent or other device placement or expansion, and other similar procedures. In relation to the devices and methods described above and elsewhere herein, the expansion members may be used to provide additional expansion force to the support members used on the prosthetic valves described herein.

Figure 17A:
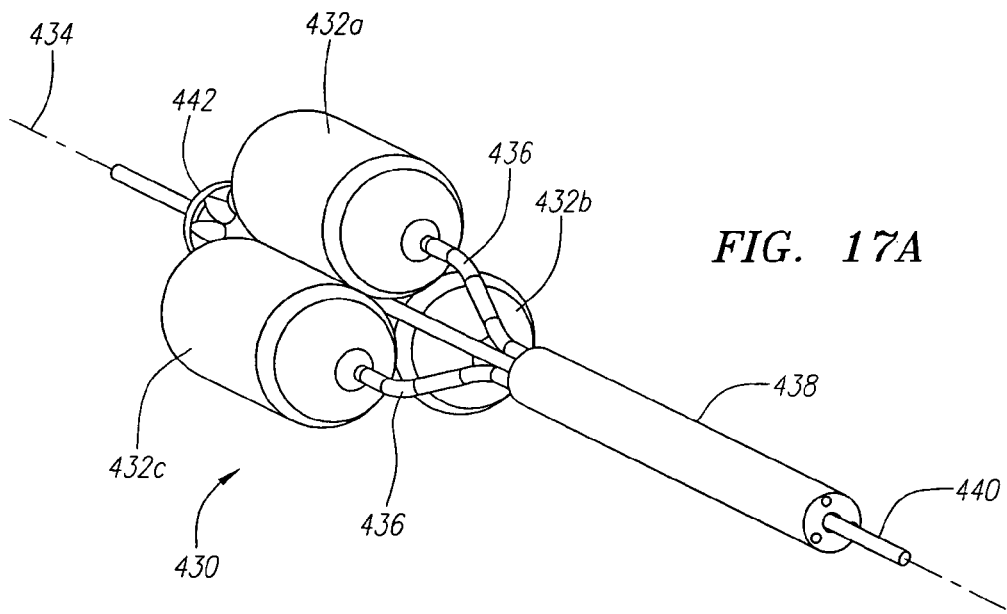
FIG. 17A is a perspective view of a multi-balloon expansion device.
Figure 17B:
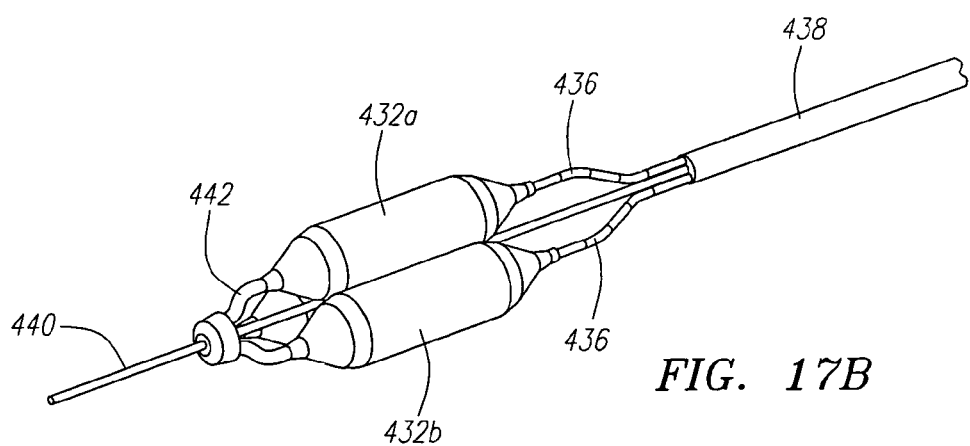
FIG. 17B is another perspective view of the multi-balloon expansion device shown in FIG. 17A.
Figure 18A:
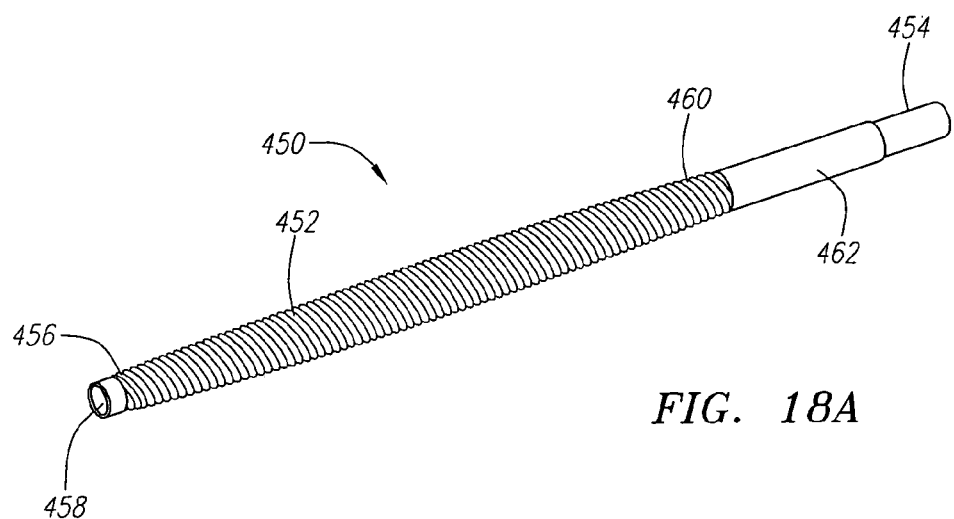
FIG. 18A is a perspective view of an expandable mesh member, shown in its contracted state.
Figure 18B:
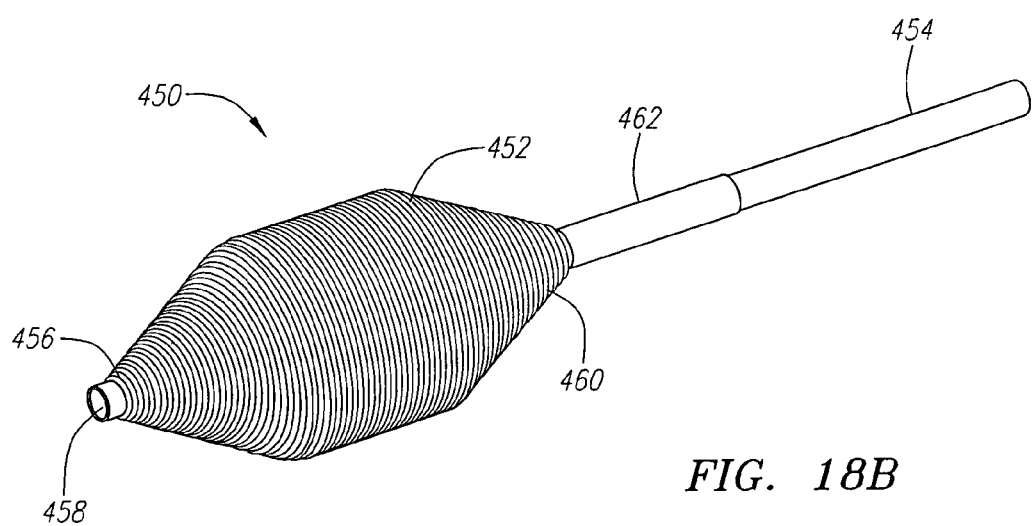
FIG. 18B is another perspective view of the expandable mesh member of FIG. 18A, shown in its expanded state.
Figure 18C:
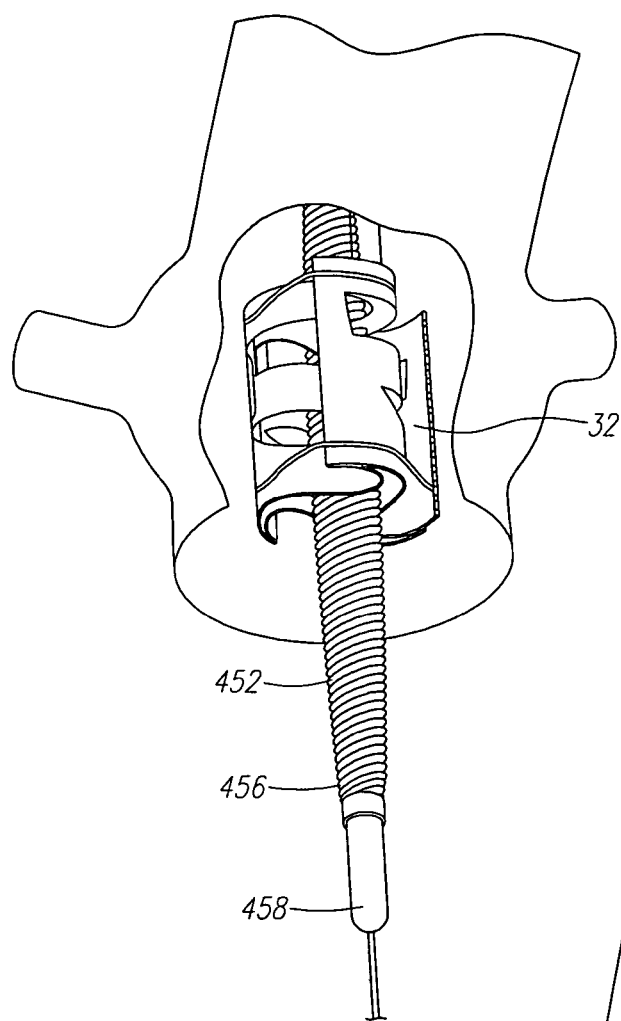
FIG. 18C is an illustration showing the expandable mesh member being advanced into the interior space of a prosthetic valve.
Figure 18D:
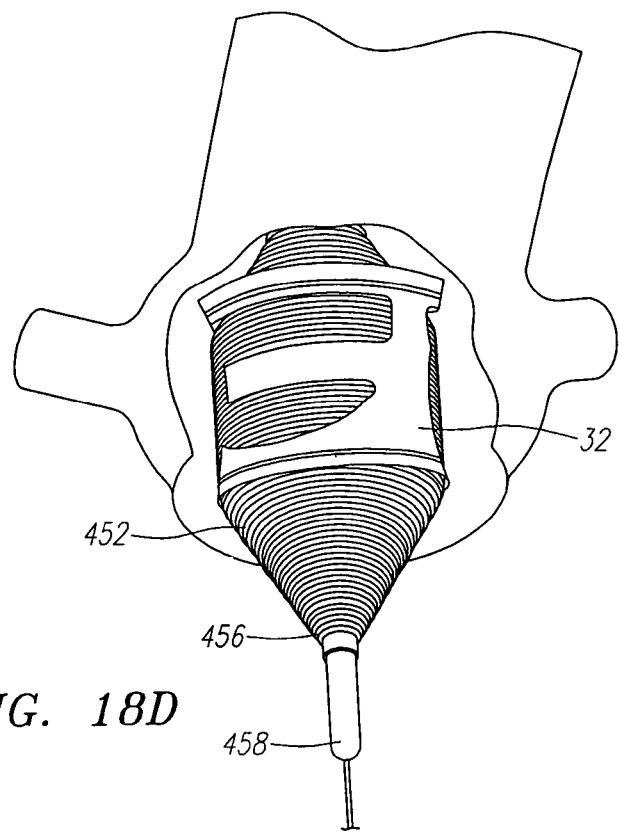
FIG. 18D is another illustration showing the expandable mesh member being advanced into the interior space of a prosthetic valve.

In one embodiment, illustrated in FIGS. 17A-B, the expansion member 430 includes three elongated inflation balloons 432a-c oriented about a longitudinal axis 434. Each inflation balloon 432 is connected at its proximal end by a feeder lumen 436 to a central lumen 438 that provides fluid communication between the inflation balloons 432a-c and a source of inflation media associated with a handle portion 308 of a catheter. The central lumen itself is provided with a guidewire lumen 440 to allow passage of a guidewire through the expansion member 430. A flexible member 442 is attached to the distal end of each of the inflation balloons 432a-c, and also includes a guidewire lumen. Although the expansion member shown in the Figures includes three inflation balloons, fewer or more balloons are possible. Moreover, each of the individual balloons may be inflated separately, all inflated together, or any combination thereof to obtain a desired force profile. The multiple inflation balloon structure provides a number of advantages, including the ability to provide greater radial forces than a single balloon, and the ability to avoid occluding a vessel undergoing treatment and to allow blood or other fluid to flow through the device.

In an alternative embodiment, shown in FIGS. 18A-D, the expansion member 450 comprises a flexible, expandable mesh member 452. The expandable mesh member 452 includes a shaft 454 and a cylindrical woven mesh member 452 disposed longitudinally over the shaft. A distal end 456 of the cylindrical mesh member is attached to the distal end 458 of the shaft. The proximal end 460 of the cylindrical mesh member is slidably engaged to the shaft by a collar 462 proximally of the distal end 456. As the collar 462 is advanced distally along the shaft 454, the body of the cylindrical mesh member 452 is caused to expand radially, thereby providing a radially expandable member.

The preferred embodiments of the inventions that are the subject of this application are described above in detail for the purpose of setting forth a complete disclosure and for the sake of explanation and clarity. Those skilled in the art will envision other modifications within the scope and spirit of the present disclosure. Such alternatives, additions, modifications, and improvements may be made without departing from the scope of the present inventions, which is defined by the claims.

What is claimed is:

1. A method for implanting a prosthetic heart valve, comprising:
    inserting a prosthetic heart valve in a contracted state into the body of a patient, said prosthetic heart valve having a plurality of valve leaflets and a support structure, the support structure comprising a plurality of self-expandable metallic panels being different from and configured to support the plurality of valve leaflets and said contracted state including at least one of said panels of the prosthetic heart valve being in an inverted state,
    introducing the prosthetic heart valve to a treatment site of a body lumen having a tissue wall, and
    expanding the cross-sectional profile of the prosthetic heart valve into direct contact with the tissue wall of the body lumen, wherein expanding the cross-sectional profile comprises transitioning the at least one panel out of the inverted state.

2. The method of claim 1, wherein all of said plurality of panels are formed into a generally tubular shape when the prosthetic heart valve is in its contracted state.

3. The method of claim 1, wherein said prosthetic heart valve further comprises at least one foldable junction member connecting two adjacent panels, and wherein at least one of said plurality of panels is inverted when the prosthetic heart valve is in its contracted state, whereby at least one foldable junction member forms an elongated vertex.

4. The method of claim 3, wherein each pair of adjacent panels forms a lobe when the prosthetic heart valve is in its contracted state.

5. The method of claim 1, further comprising the step of installing the prosthetic heart valve in a delivery device having a tubular valve restraining member.

6. The method of claim 5, wherein said installing step includes causing relative rotation between the tubular valve restraining member and the entire prosthetic heart valve to cause said prosthetic heart valve to assume the contracted state.

7. The method of claim 1, wherein said expanding step includes releasing the prosthetic heart valve from a delivery device.

8. The method of claim 1, wherein said expanding step includes expanding an expandable member located within at least a portion of the prosthetic heart valve.

9. The method of claim 1, further comprising:
repositioning said prosthetic heart valve.

10. The method of claim 9, wherein said repositioning step comprises:
at least partially contracting the prosthetic heart valve,
moving the contracted prosthetic heart valve to another location, and
expanding the prosthetic heart valve.

11. The method of claim 1, wherein said treatment site is in or around a patient's heart.

12. The method of claim 11, wherein said treatment site is in or around a patient's aortic valve root.

13. The method of claim 11, wherein said treatment site is in or around a patient's ascending aorta.

14. The method of claim 11, wherein said treatment site is in or around a patient's descending aorta.

15. The method of claim 1, wherein each inverted panel has a concave shape.

16. The method of claim 15, wherein expanding the cross-sectional profile of the prosthetic heart valve comprises transitioning the inverted panels from the concave shape into a convex shape.

17. The method of claim 1, wherein each of the panels is inverted in the contracted state.

18. The method of claim 1, wherein each of the panels comprises nitinol.

19. The method of claim 1, wherein expanding the cross-sectional profile comprises expanding the cross-sectional profile into a generally tubular shape having a fixed diameter.

20. The method of claim 1, wherein the prosthetic heart valve has only three invertible panels.

21. The method of claim 20, wherein the prosthetic heart valve comprises only three valve leaflets, each valve leaflet being coupled to only one of the invertible panels.

22. The method of claim 1, wherein the support member consists essentially of the plurality of panels and a foldable junction member between each adjacent panel, wherein each panel is invertible.

23. The method of claim 1, wherein each panel is configured to self-expand immediately upon removal of a restraining member, and wherein expanding the cross-sectional profile of the prosthetic heart valve comprises removing the restraining member from restraining contact with the inverted panel.

24. The method of claim 1, wherein the prosthetic heart valve has a longitudinal axis and the at least one inverted panel of the prosthetic heart valve is curled towards the longitudinal axis when in the contracted state.

25. The method of claim 24, wherein expanding the cross-sectional profile of the prosthetic heart valve comprises uncurling the at least one inverted panel prior to transitioning the at least one panel out of the inverted state.

26. A method for implanting a prosthetic heart valve, comprising:
inserting a prosthetic heart valve in a contracted state into the body of a patient, said prosthetic heart valve having a plurality of valve leaflets and a support structure, the support structure comprising only three self-expandable metallic panels different from and configured to support the plurality of valve leaflets, wherein, in the contracted state, the prosthetic heart valve has a longitudinal axis and each panel of the prosthetic heart valve is inverted in a concave shape and curled towards the longitudinal axis,
introducing the prosthetic heart valve to a treatment site in a body lumen having a tissue wall, and
expanding the cross-sectional profile of the prosthetic heart valve into direct contact with the tissue wall of the body lumen, wherein expanding the cross-sectional profile comprises uncurling each of the panels away from the longitudinal axis and then transitioning each of the panels from the concave shape into a convex shape.

27. The method of claim 26, wherein said prosthetic heart valve further comprises at least one foldable junction member connecting two adjacent panels, and wherein the at least one foldable junction member forms an elongated vertex when the prosthetic heart valve is in the contracted state.

28. The method of claim 27, wherein each pair of adjacent panels forms a lobe when the prosthetic heart valve is in the contracted state.

29. The method of claim 26, further comprising causing relative rotation between a tubular valve restraining member and the entire prosthetic heart valve, prior to inserting the prosthetic heart valve, to cause said prosthetic heart valve to assume the contracted state.

30. The method of claim 26, wherein expanding the cross-sectional profile of the prosthetic heart valve comprises releasing the prosthetic heart valve from a delivery device.

31. The method of claim 26, wherein expanding the cross-sectional profile of the prosthetic heart valve comprises expanding an expandable member located within at least a portion of the prosthetic heart valve.

32. The method of claim 26, further comprising:
at least partially contracting the prosthetic heart valve,
moving the contracted prosthetic heart valve to another location, and
expanding the prosthetic heart valve.

33. The method of claim 26, wherein said treatment site is in or around a patient's heart.

34. The method of claim 26, wherein said treatment site is in or around a patient's aortic valve root.

35. The method of claim 26, wherein said treatment site is in or around a patient's ascending aorta.

36. The method of claim 26, wherein said treatment site is in or around a patient's descending aorta.

37. The method of claim 26, wherein each panel is configured to self-expand immediately upon removal of a restraining member, and wherein expanding the cross-sectional profile of the prosthetic heart valve comprises removing restraining members from restraining contact with the inverted panels after uncurling each of the panels.

38. The method of claim 26, wherein each of the panels comprises nitinol.

39. The method of claim 26, wherein expanding the cross-sectional profile comprises expanding the cross-sectional profile into a generally tubular shape having a fixed diameter.

40. The method of claim 26, wherein the prosthetic heart valve comprises only three valve leaflets, each valve leaflet being coupled to only one of the invertible panels.

\* \* \* \* \*